(12) United States Patent
Metsky et al.

(10) Patent No.: US 11,332,783 B2
(45) Date of Patent: May 17, 2022

(54) SAMPLE ANALYSIS, PRESENCE DETERMINATION OF A TARGET SEQUENCE

(71) Applicants: THE BROAD INSTITUTE, INC., Cambridge, MA (US); MASSACHUSETTS INSTITUTE OF TECHNOLOGY, Cambridge, MA (US); PRESIDENT AND FELLOWS OF HARVARD COLLEGE, Cambridge, MA (US)

(72) Inventors: Hayden Metsky, Cambridge, MA (US); Andreas Gnirke, Cambridge, MA (US); Christian Matranga, Cambridge, MA (US); Daniel Park, Cambridge, MA (US); Pardis Sabeti, Cambridge, MA (US)

(73) Assignees: The Broad Institute, Inc., Cambridge, MA (US); Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 767 days.

(21) Appl. No.: 15/756,546

(22) PCT Filed: Aug. 26, 2016

(86) PCT No.: PCT/US2016/049071
§ 371 (c)(1),
(2) Date: Feb. 28, 2018

(87) PCT Pub. No.: WO2017/040316
PCT Pub. Date: Mar. 9, 2017

(65) Prior Publication Data
US 2018/0340215 A1    Nov. 29, 2018

Related U.S. Application Data

(60) Provisional application No. 62/211,541, filed on Aug. 28, 2015.

(51) Int. Cl.
| | | |
|---|---|---|
| *C12Q 1/686* | (2018.01) | |
| *C12Q 1/70* | (2006.01) | |
| *C12Q 1/6816* | (2018.01) | |
| *C12Q 1/6809* | (2018.01) | |
| *C07H 21/04* | (2006.01) | |
| *C12Q 1/6806* | (2018.01) | |

(52) U.S. Cl.
CPC ............ *C12Q 1/686* (2013.01); *C07H 21/04* (2013.01); *C12Q 1/6806* (2013.01); *C12Q 1/6809* (2013.01); *C12Q 1/6816* (2013.01); *C12Q 1/701* (2013.01); *Y02A 50/30* (2018.01)

(58) Field of Classification Search
None
See application file for complete search history.

(56) References Cited

U.S. PATENT DOCUMENTS

| | | |
|---|---|---|
| 2010/0029498 A1 | 2/2010 | Gnirke et al. |
| 2013/0190196 A1 | 7/2013 | Onderdonk et al. |
| 2013/0230857 A1 | 9/2013 | Gnirke et al. |
| 2014/0200163 A1 | 7/2014 | Mikkelsen et al. |
| 2014/0228223 A1 | 8/2014 | Gnirke et al. |
| 2015/0126377 A1 | 5/2015 | Gnirke et al. |

FOREIGN PATENT DOCUMENTS

| | | |
|---|---|---|
| WO | 2009/099602 A1 | 8/2009 |
| WO | 2017/040316 A1 | 3/2017 |

OTHER PUBLICATIONS

Borneman, James, et al. "Probe selection algorithms with applications in the analysis of microbial communities." Bioinformatics 17. suppl_1 (2001): S39-S48.*
Seven Bridges, blog posting, "Short read alignment: seeding," author: "Nate," downloaded from (https://www.sevenbridges.com/short-read-alignment-seeding/), 4 pages, Jun. 4 (Year: 2013).*
Wikipedia, "Set cover problem," downloaded from (https://en.wikipedia.org/wiki/Set_cover_problem), 1 page (Year: 2022).*
Geniez et al., "Targeted Genome Enrichment for Efficient Purification of Endosymbiont DNA from Host DNA", Symbiosis, vol. 58, No. (1-3), Dec. 2012, 201-207.
Gnirke et al., "Solution Hybrid Selection with Ultra-Long Oligonucleotides for Massively Parallel Targeted Sequencing", Nature Biotechnology, vol. 27, No. 2, Feb. 2009, 182-189.
Hoffmann et al., "Design and Coverage of High Throughput Genotyping Arrays Optimized for Individuals of East Asian, African American, and Latino Race/Ethnicity using Imputation and a Novel Hybrid SNP Selection Algorithm", Genomics, vol. 98, No. 6, Dec. 2011, 23 pages.
Matranga et al., "Enhanced Methods for Unbiased Deep Sequencing of Lassa and Ebola RNA Viruses from Clinical and Biological Samples", Genome Biology, vol. 15, No. 11, Nov. 18, 2014, 12 pages.
Melnikov et al., "Hybrid Selection for Sequencing Pathogen Genomes from Clinical Samples", Genome Biology, vol. 12, No. R73, Aug. 11, 2011, 9 pages.
International Search Report and Written Opinion for PCT International Application No. PCT/US2016/049071, dated Nov. 28, 2016, 11.

(Continued)

*Primary Examiner* — G Steven Vanni
(74) *Attorney, Agent, or Firm* — Johnson, Marcou, Isaacs & Nix, LLC; F. Brent Nix, Esq.; Michael B. Scher, Esq.

(57) ABSTRACT

The present invention provides a combination of genomic and computational technologies to provide rapid, portable sample analysis for sequencing or identifying a target sequence involving generating probes for use in analyzing a sample which may comprise a target sequence.

23 Claims, 20 Drawing Sheets

Specification includes a Sequence Listing.

(56) References Cited

OTHER PUBLICATIONS

Taghipour, et al., "Applying Surface-Based DNA Computing for Solving the Dominating Set Problem", American Journal of Molecular Biology, Jul. 2012, 286-290.
"International Preliminary Report on Patentability for PCT Application No. PCT/US2016/049071", BROD-0690WP, dated Mar. 15, 2018, 1-10.
Duitama, et al., "PrimerHunter: A Primer Design Tool for PCR-Based Virus Subtype Identification", Nucleic Acids Res, vol. 37, No. 8, Mar. 5, 2009, 2483-2492.
Jabado, et al., "Comprehensive Viral Oligonucleotide Probe Design Using Conserved Protein Regions", Nucleic Acids Research, vol. 36, No. 1, Dec. 13, 2007, 10.
Jabado, et al., "Greene SCPrimer: A Rapid Comprehensive Tool for Designating Degenerate Primers from Multiple Sequence Alignments", Nucleic Acids Reseach, vol. 34, No. 22, Nov. 28, 2006, 6605-6611.
Pearson, et al., "On the Primer Selection Problem in Polymerase Chain Reaction Experiments", Discrete Applied Mathematics, vol. 71, 1996, 231-246.
Phillippy, et al., "Efficient Oligonucleotide Probe Selection for Pan-Genomic Tiling Arrays", BMC Bioinformatics, vol. 10, No. 293, Sep. 16, 2009, 14.
Nate, "Short read alignmentseeding", Science, Seven Bridges, Back to Blog, Jun. 4, 2013, 4 pages.

\* cited by examiner

SAMPLE ANALYSIS, PRESENCE DETERMINATION OF A TARGET SEQUENCE

REFERENCE TO RELATED APPLICATIONS

This application is a national stage application of International Application No. PCT/US2016/049071 filed Aug. 26, 2016, which claims priority to U.S. Provisional Application No. 62/211,541 filed Aug. 28, 2015, the complete disclosures of which are hereby fully incorporated herein by reference.

STATEMENT OF GOVERNMENT SUPPORT

This invention was made with government support under grant numbers U19AI110818 and HHSN272200900049C awarded by the National Institutes of Health. The government has certain rights in the invention.

INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention provides a combination of genomic and computational technologies to provide rapid, portable sample analysis for sequencing or identifying a target sequence.

BACKGROUND OF THE INVENTION

Infectious diseases cause tremendous morbidity and mortality in tropical developing countries, and the need for a holistic approach to their detection and diagnosis is increasingly clear. The full range and prevalence of pathogens in such settings is not well understood, and the capacity to detect new or infrequent threats, like Ebola, is often lacking. The ability to diagnose a broad spectrum of pathogens is vital, since infection with multiple pathogens and resulting misdiagnoses are common.

Within this aim, sequencing is a powerful tool for analyzing a clinical sample. Clinical samples are biological mixtures that comprise little target sequences. The target sequences usually amount to less than 1% of the biological mixtures.

One method for overcoming the scarcity of target sequences is hybrid selection that makes it possible to capture target sequences out of the biological mixtures. Hybrid selection necessitates a set of probes selected from candidate probes that capture target sequences or fragments thereof when brought into contact therewith. The candidate probes are constructed so as to cover collectively the target sequences entirely or partially depending on the application of the analysis. However, occurrence of redundancies across candidate probes is usually high: a high number of candidate probes hybridize with a portion of one same target sequence. Utilizing a high number of candidate probes for hybrid selection is resource and time-consuming so that designing solutions for rapid and portable analysis can only be contemplated for the most common viruses. Therefore, efforts have been made to reduce the number of probes used for hybrid selection.

Reducing the number of probes currently consists in comparing the different candidate probes to one another in an iterative manner, i.e. within a list of probes, for one given probe, remove all other probes from the list of probes that is redundant to the given probe and continue with the next probe remaining in the list of probes. Two probes are considered redundant if they are shifted with respect to one another by a distance of less than a threshold shift and present a number of mismatches up to a mismatch threshold (see, e.g., FIG. 1).

Unfortunately, the output of this method, i.e. the selected probes, depends greatly on how the candidate probes are ordered. Further, considering n number of candidate probes, the number of selected probes can be a factor n away from optimal so that the total of selected probes used for analyzing a sample is high.

Citation or identification of any document in this application is not an admission that such document is available as prior art to the present invention.

SUMMARY OF THE INVENTION

Applicants' goal is to develop a comprehensive system, for detecting, diagnosing and monitoring infectious disease. Applicants' proposed system is intended to address multiple unmet needs in current health care delivery using three approaches: developing more rapid and cost-efficient sequencing to understand the history and mechanism of pathogen outbreaks; more rapid and cost-efficient identification of pathogens within a sample; the precise and more sensitive diagnostics that capture and discriminate between various pathogens; and providing far greater access to powerful diagnostic tools at the local level.

First, there is a need in patient care for more comprehensive diagnostic tests. Many pathogens produce non-specific symptoms like fever, headache, and nausea, making them difficult to distinguish clinically (Formenty et al., Journal of Infectious Diseases 179, S48 (1999); J. B. McCormick et al., J Infect Dis 155, 445 (1987)). For example, 30%-90% of hospitalized patients with acute fever in tropical Africa are diagnosed with malaria and treated accordingly, while only 7%-45% of them actually have laboratory-confirmed malaria. Better tests for individual diseases will be useful, but will not fully solve the problem: e.g., many patients with detectable malaria are actually sick because of other infections (M. Amexo, R. Tolhurst, G. Barnish, I. Bates, Malaria misdiagnosis: effects on the poor and vulnerable. Lancet 364, 1896 (2004); H. Reyburn et al., BMJ 329, 1212 (2004); D. Sur et al., Trans R Soc Trop Med Hyg 100, 725 (2006)). Such misdiagnoses can be fatal, as in a 1989 outbreak of Lassa fever in two Nigerian hospitals, where 22 people died (S. P. Fisher-Hoch et al., BMJ 311, 857 (Sep. 30, 1995)). Thus, Applicants develop a low-cost PCR-based panel for a range of infectious diseases as a routine diagnostic procedure for febrile patients.

Second, there is a need to better understand the array of existing pathogens and to detect emerging threats. Lassa virus, once thought to be a novel cause of sporadic disease outbreaks, has turned out to be endemic in much of West Africa, and there is even evidence that Ebola circulates undetected more widely than is supposed (R. J. Schoepp et al., Emerg Infect Dis 20, 1176 (2014); S. K. Gire et al., Science 338, 750 (2012).). Any samples that fail Applicants' diagnostic panel, therefore, are sent for deep metagenomic sequencing to detect other pathogens. A random selection of other samples are treated the same way, to provide a broad picture of the range of pathogens in the region, which in turn will make early detection of new or increasing pathogens possible.

Technological advances in sequencing and analyzing the genomes of a wide variety of microbes, including the costs of implementing genomic approaches at scale, make it possible to address these needs. But to fulfill that promise, the tools must be delivered to researchers and clinicians on the ground. Empowering local health care clinics and their communities, in turn, will help motivate patients to seek care at the clinic. In addition to saving lives, this enables us to continually monitor patients with unexplained fever, capturing diseases that previously went undiagnosed or misdiagnosed. After local diagnosis, samples can then be sent to advanced laboratories in the US—and hopefully soon Africa too—for in-depth analysis using high-throughput metagenomic sequencing. Discoveries of new pathogens are then be converted into affordable, field-deployable diagnostics to inform health care workers and the populations they serve, reducing the burden of disease and improving local capacity to detect and treat at the earliest possible stages. Robust data systems are needed to connect sample collections, the process of pathogen identification, and candidates for developing diagnostics and treatments. By comprehensively identifying pathogens circulating in the population this new infrastructure serves as an early warning for emerging and persistent diseases. With their own diagnostic capacity for a wide range of infectious agents, sites throughout Africa are able to support their communities and help to detect, monitor and characterize emerging diseases before they become global threats.

According to one aspect of the invention, a method for generating probes for use in analyzing a sample is provided and comprises a target sequence, which may comprise:

a. constructing candidate probes capable of hybridizing a reference sequence, said candidate probes collectively having a hybridization pattern along the length of the reference sequence;

b. determining an individual hybridization pattern for each candidate probe to provide a collection of individual hybridization patterns;

c. subjecting the individual hybridization patterns to a set cover solving process to reduce the number of candidate probes to provide selected probes; and d. synthesizing the selected probes.

In certain example embodiments, the candidate probes may collectively have a hybridization pattern along the entire length of the reference sequence.

According to another aspect of the invention, the set cover solving process may be a weighted set cover solving process, a partial set cover solving process or a partial weighted set cover solving process.

According to another aspect, a method of analyzing a sample which may comprise a target sequence is provided, which may comprise:

a. contacting the selected probes to the target sequence or a fragment thereof; and b. sequencing the target sequence or fragment thereof that hybridizes to one or more of the selected probes.

According to another aspect of the invention, the set cover solving process may be a greedy method. Alternate methods may also be used to solve set cover process.

According to another aspect of the invention, subjecting the individual hybridization patterns to a set cover solving process may comprise:

a. allocating a lower weight to those individual hybridization patterns that correspond to candidate probes that are specific to the target sequence; and b. allocating a higher weight to those individual hybridization patterns that correspond to candidate probes that are not specific to the target sequence.

According to another aspect of the invention, the method may further comprise minimizing a loss function depending on overhang parameters and mismatch parameters such that the total number of selected probes is no higher than a threshold number to provide input parameters to the set cover solving process.

According to another aspect, a method for generating probes for use in analyzing a sample which may comprise a target sequence is provided, which may comprise:

a. constructing candidate probes capable of hybridizing a reference sequence, said candidate probes collectively having a hybridization pattern along the length of the reference sequence;

b. assessing redundancy between candidate probes; and c. subjecting the candidate probes to a dominating set solving process to reduce the number of candidate probes to provide a selected probes, wherein any candidate probe is either a selected probe or redundant to a selected probe.

According to another aspect, the present invention also encompasses a composition which may comprise selected probes produced by any of the methods disclosed herein.

According to another aspect, a kit is provided, which may comprise a composition which may comprise selected probes produced by any of the methods disclosed herein and a solid phase operatively linked to the selected probes. In the case where biotin is employed as a labeling substance, preferably, after addition of a biotin-labeled antibody, streptavidin bound to an enzyme (e.g., peroxidase) is further added. In another embodiment, the hybridization may be in solution.

According to another aspect, a system for enrichment of genomic DNA of a target organism in a sample that may comprise both DNA of the target organism and non-specific DNA is provided which may comprise:

a. selected probes produced by any of the herein disclosed methods;

b. a sample containing DNA of said target organism and the non-specific DNA; and c. a solid phase operatively connected to the selected probes.

According to another aspect of the invention involving kits or systems, the solid phase may be a bead or a chip. In another embodiment, the hybridization may be in solution.

According to another aspect of the invention involving kits or systems, the selected probes may further comprise an adapter, such as a label.

According to another aspect of the invention, analysis of the target sequence or a fragment thereof hybridized to a selected probe may be by in solution hybrid selection. In this aspect, each of the selected probes may further comprise an adapter. In this aspect, each of the selected probes may comprise two adapters. In this aspect, a first adapter may be alternated with a second adapter. In this aspect, two of the selected probes may overlap.

According to another aspect of the invention, the candidate probe or the selected probe may be a nucleic acid sequence. In this aspect, the nucleic acid may be DNA, RNA, peptide nucleic acid ("PNA") or other non-naturally occurring nucleic acid.

According to another aspect of the invention, the sample may be obtained from a human. In this aspect, the sample may be a biological sample. In this aspect, the biological sample may be a blood, buccal, cell, cerebrospinal fluid, mucus, saliva, semen, tissue, tumor, feces, urine or vaginal sample.

According to another aspect of the invention, the target sequence may be a nucleotide sequence. In this aspect, the nucleotide sequence may be a DNA sequence or a RNA sequence. In this aspect, wherein the nucleotide sequence may be a pathogenic or viral sequence. In this aspect, the viral sequence may be an Ebola, measles, SARS, Chikungunya, hepatitis, Marburg, yellow fever, MERS, Dengue, Lassa, influenza, rhabdovirus or HIV viral sequence. In this aspect, viral sequence may be a Ebola Zaire Bundibugyo, Sudan, Reston and Taï Forest sequence. In this aspect, the hepatitis viral sequence may be a hepatitis A, hepatitis B or hepatitis C viral sequence. In this aspect, the influenza viral sequence may be an influenza A or influenza B viral sequence. In this aspect, the HIV viral sequence may be a HIV 1 or HIV 2 viral sequence.

The methods of the present invention may be applied to any organism with a nucleotide sequence—anything with sequence data. The organism is not limited to a viral or pathogenic organism. For example, methods of the present invention may apply to gut flora or gut microbiota, in particular the gut microbiome. The present invention is also contemplated for diagnostics, in particular in mixed samples. For example, the present invention may be utilized for determining and sequencing bacteria, pathogens and/or viruses present in an organism, water, soil, surface, or a population as well as in agricultural processes.

In certain example embodiments, probe oligos may be amplified, for example using PCR. Because probes may overlap and complements arise during PCR, overlapping probes may hybridize and effectively chain together. This problem can be prevented by assigning adapters to probes in a way that ensures that probes that might overlap are assigned different adapters and PCR'd separately. In certain example embodiments, this problem is solved with a heuristic that treats the problem as an "interval scheduling problem" in which hybridization patterns of each probe are examined and the hybridizations treated as intervals. The interval scheduling problem is then solved to find the maximum number of non-overlapping probes which can all be assigned the same adapter because they do not chain together. This process can continue, at each stage using a different adapter. The various adapters on both the 5' and 3' ends are given as input.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIGS. 12 and 13 graphically show the number of selected probes generated as output of Example 2.1, Example 2.2 and Comparative example 2.

FIG. 27 shows sequencing without hybrid selection and FIG. 28 shows sequencing with hybrid selection.

DETAILED DESCRIPTION OF THE INVENTION

Figure 1:
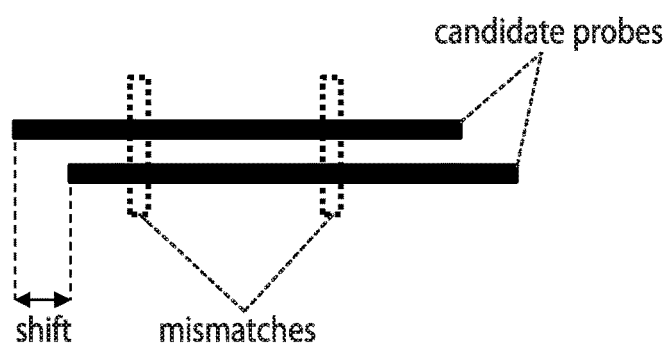
FIG. 1 shows that two probes are considered redundant if they are shifted with respect to one another by a distance of less than a threshold shift and present a number of mismatches up to a mismatch threshold.

Future pandemics threaten human progress and must be detected early. Applicants' goal is to achieve a sustainable, rapid-response surveillance system to detect infectious disease outbreaks as soon as they appear. To do so, Applicants must vastly improve both diagnostic tools and the human resources to deploy them. The present invention relates to developing rapid pathogen sequencing for comprehensive microbial detection.

Rapid advances in DNA sequencing technology provide an unprecedented capability to identify and characterize pathogens, and will soon enable comprehensive and unbiased pathogen surveillance for early detection and prevention of future epidemics. However, realizing its full potential for infectious disease surveillance and clinical diagnosis present additional challenges, which require further investment and focused effort. Applicants are developing scalable, rapid and field-deployable laboratory and computational methods to: (i) catalog and classify the microbes in patients' blood, (ii) determine the causal agent, and (iii) characterize the pathogen's properties.

The present invention relates to a method for generating probes for use in analyzing a sample which may comprise a target sequence, such as (a) constructing candidate probes capable of hybridizing a reference sequence, said candidate probes collectively having a hybridization pattern along the length of the reference sequence; (b1) determining an individual hybridization pattern for each candidate probe to provide a collection of individual hybridization patterns; (c1) subjecting the individual hybridization patterns to a set cover solving process to reduce the number of candidate probes to provide selected probes; and (d) synthesizing the selected probes.

In certain example embodiments, the methods for generating probes may comprise a set cover solution. The set cover solution may identify the minimal number of probes needed to cover an entire target sequence or set of target sequences, e.g. a set of genomic sequences. Set cover approaches have been used previously to identify primers and/or microarray probes, typically in the 20 to 50 base pair range. See, e.g. Pearson et al., www.cs.virginia.edu/~robins/papers/primers_dam11_final.pdf., Jabado et al. Nucleic Acids Res. 2006 34(22):6605-11, Jabado et al. Nucleic Acids Res. 2008, 36(1):e3 doi10.1093/nar/gkm1106, Duitama et al. Nucleic Acids Res. 2009, 37(8):2483-2492, Phillippy et al. BMC Bioinformatics. 2009, 10:293 doi: 10.1186/1471-2105-10-293. However, such approaches generally involved treating each primer/probe as k-mers and searching for exact matches or allowing for inexact matches using suffix arrays. In addition, the methods generally take a binary approach to detecting hybridization by selecting primers or probes such that each input sequence only needs to be bound by one primer or probe and the position of this binding along the sequence is irrelevant. Alternative methods may divide a target genome into pre-defined windows and effectively treat each window as a separate input sequence under the binary approach—i.e. they determine whether a given primer or probe binds within each window and require that all of the windows be bound by the state of some primer or probe. Effectively, these approaches treat each element of the "universe" in the set cover problem as being either an entire input sequence or a pre-defined window of an input sequence, and each element is considered "covered" if the start of a probe binds within the element. These approaches limit the fluidity to which different primer or probe designs are allowed to cover a given target sequence.

In contrast, the embodiments disclosed herein are directed to detecting longer probe lengths, for example, in the range of 70 bp to 200 bp that are suitable for hybrid selection sequencing. In addition, the methods disclosed herein take a pan-target sequence approach capable of defining a probe set that can identify and facilitate the sequencing of all sequences in a large and/or variable target sequence set. For example, the methods disclosed herein may be used to identify all variants of a given virus, or multiple different viruses in a single assay. Further, the method disclosed herein treat each element of the "universe" in the set cover problem as being a nucleotide of a target sequence, and each element is considered "covered" as long as a probe binds to some segment of a target genome that includes the element. Instead of the binary approach of previous methods, the methods disclosed herein better model how a probe, and in particular larger probes, may hybridize to a target sequence. Rather than only asking if a given sequence does or does not bind to a given window, embodiments disclosed herein first determine a hybridization pattern—i.e. where a given probe binds to a target sequence or target sequences—and then determines from those hybridization patterns the minimum number of probes needed to cover the set of target sequences to a degree sufficient to enable both enrichment from a sample and sequencing of any and all target sequences. These hybridization patterns may be determined by defining certain parameters that minimize a loss function, thereby enabling identification of minimal probes sets in a way that allows parameter to vary for each species, e.g. to reflect the diversity of each species, as well as in a computationally efficient manner that cannot be achieved using a straightforward application of a set cover solution, such as those previously applied in the primer and microarray probe design context.

A probe, a candidate probe or a selected probe may be a nucleic acid sequence, the nucleic acid being for example deoxyribonucleic acid (DNA), ribonucleic acid (RNA), peptide nucleic acid (PNA) or other non-naturally occurring nucleic acid.

The sample may be a biological sample, for example a blood, buccal, cell, cerebrospinal fluid, mucus, saliva, semen, tissue, tumor, feces, urine, and vaginal sample. It may be obtained from an animal, a plant or a fungus. The animal may be a mammal. The mammal may be a primate. The primate may be a human. In other embodiments, the sample may be an environmental sample, such as water, soil, or a surface such as industrial or medical surface.

"Target sequence" is intended to designate either one target sequence or more than one target sequence, i.e. any sequence of interest at which the analysis is aimed. Thus, the sample may comprise more than one target sequence and preferably a plurality of target sequences, the number of which may be 2, 3, 4, 5, 6, 7, 8, 9, 10, 11, 12, 13, 14, 15, 16, 17, 18, 19, 20 and above.

The target sequence may be a nucleotide sequence. The nucleotide sequence may be a DNA sequence, a RNA sequence or a mixture thereof. The nucleotide sequence may be a pathogenic or non-pathogenic sequence. The nucleotide sequence may be a bacterial sequence, a eukaryotic sequence, a viral sequence or a mixture thereof.

In certain example embodiments, the viral sequence may be a human respiratory syncytial virus, Sudan ebola virus, Bundibugyo virus, Tai Forest ebola virus, Reston ebola virus, Achimota, *Aedes* flavivirus, Aguacate virus, Akabane virus, Alethinophid reptarenavirus, Allpahuayo mammarenavirus, Amapari mammarenavirus, Andes virus, Apoi virus, Aravan virus, Aroa virus, Arumowot virus, Atlantic salmon paramyxovirus, Australian bat lyssavirus, Avian bornavirus, Avian metapneumovirus, Avian paramyxovirus, penguin or Falkland Islandsvirus, BK polyomavirus, Bagaza virus, Banna virus, Bat hepevirus, Bat sapovirus, Bear Canon mammarenavirus, Beilong virus, Betacoronavirus, Betapapillomavirus 1-6, Bhanja virus, Bokeloh bat lyssavirus, Borna disease virus, Bourbon virus, Bovine hepacivirus, Bovine parainfluenza virus 3, Bovine respiratory syncytial virus, Brazoran virus, Bunyamwera virus, California encephalitis virus, Candiru virus, Canine distemper virus, Canine pneumovirus, Cedar virus, Cell fusing agent virus, Cetacean morbillivirus, Chandipura virus, Chaoyang virus, Chapare mammarenavirus, Chikungunya virus, Colobus monkey papillomavirus, Colorado tick fever virus, Cowpox virus, Crimean-Congo hemorrhagic fever virus, *Culex* flavivirus, Cupixi mammarenavirus, Dengue virus, Dobrava-Belgrade virus, Donggang virus, Dugbe virus, Duvenhage virus, Eastern equine encephalitis virus, Entebbe bat virus, Enterovirus A-D, European bat lyssavirus 1-2, Eyach virus, Feline morbillivirus, Fer-de-Lance paramyxovirus, Fitzroy River virus, Flexal mammarenavirus, GB virus C, Gairo virus, Gemycircularvirus, Goose paramyxovirus SF02, Great Island virus, Guanarito mammarenavirus, Hantaan virus, Hantavirus Z10, Heartland virus, Hendra virus, Hepatitis A/B/C/E, Hepatitis delta virus, Human bocavirus, Human coronavirus, Human endogenous retrovirus K, Human enteric coronavirus, Human genital-associated circular DNA virus-1, Human herpesvirus 1-8, Human immunodeficiency virus 1/2, Huan mastadenovirus A-G, Human papillomavirus, Human parainfluenza virus 1-4, Human parechovirus, Human picobirnavirus, Human smacovirus, Ikoma lyssavirus, Ilheus virus, Influenza A-C, Ippy mammarenavirus, Irkut virus, J-virus, JC polyomavirus, Japanese encephalitis virus, Junin mammarenavirus, KI polyomavirus, Kadipiro virus, Kamiti River virus, Kedougou virus, Khuj and virus, Kokobera virus, Kyasanur forest disease virus, Lagos bat virus, Langat virus, Lassa mammarenavirus, Latino mammarenavirus, Leopards Hill virus, Liao ning virus, Ljungan virus, Lloviu virus, Louping ill virus, Lujo mammarenavirus, Luna mammarenavirus, Lunk virus, Lymphocytic choriomeningitis mammarenavirus, Lyssavirus Ozernoe, MSSI2.225 virus, Machupo mammarenavirus, Mamastrovirus 1, Manzanilla virus, Mapuera virus, Marburg virus, Mayaro virus, Measles virus, Menangle virus, Mercadeo virus, Merkel cell polyomavirus, Middle East respiratory syndrome coronavirus, Mobala mammarenavirus, Modoc virus, Mojiang virus, Mokola virus, Monkeypox virus, Montana myotis leukoencephalitis virus, Mopeia lassa virus reassortant 29, Mopeia mammarenavirus, Morogoro virus, Mossman virus, Mumps virus, Murine pneumonia virus, Murray Valley encephalitis virus, Nariva virus, Newcastle disease virus, Nipah virus, Norwalk virus, Norway rat hepacivirus, Ntaya virus, O'nyong-nyong virus, Oliveros mammarenavirus, Omsk hemorrhagic fever virus, Oropouche virus, Parainfluenza virus 5, Parana mammarenavirus, Parramatta River virus, Peste-des-petits-ruminants virus, Pichinde mammarenavirus, Pirital mammarenavirus, Piscihepevirus A, Porcine parainfluenza virus 1, porcine rubulavirus, Powassan virus, Primate T-lymphotropic virus 1-2, Primate erythroparvovirus 1, Punta Toro virus, Puumala virus, Quang Binh virus, Rabies virus, Razdan virus, Reptile bornavirus 1, Rhinovirus A-B, Rift Valley fever virus, Rinderpest virus, Rio Bravo virus, Rodent Torque Teno virus, Rodent hepacivirus, Ross River virus, Rotavirus A-I, Royal Farm virus, Rubella virus, Sabia mammarenavirus, Salem virus, Sandfly fever Naples virus, Sandfly fever Sicilian virus, Sapporo virus, Sathuperi virus, Seal anellovirus, Semliki Forest virus, Sendai virus, Seoul virus, Sepik virus, Severe acute respiratory syndrome-related coronavirus, Severe fever with thrombocytopenia syndrome virus, Shamonda virus, Shimoni bat virus, Shuni virus, Simbu virus, Simian torque teno virus, Simian virus 40-41, Sin Nombre virus, Sindbis virus, Small anellovirus, Sosuga virus, Spanish goat encephalitis virus, Spondweni virus, St. Louis encephalitis virus, Sunshine virus, TTV-like mini virus, Tacaribe mammarenavirus, Taila virus, Tamana bat virus, Tamiami mammarenavirus, Tembusu virus, Thogoto virus, Thottapalayam virus, Tick-borne encephalitis virus, Tioman virus, Torque teno *canis* virus, Torque teno douroucouli virus, Torque teno *felis* virus, Torque teno midi virus, Torque teno sus virus, Torque teno tamarin virus, Torque teno virus, Torque teno *zalophus* virus, Tuhoko virus, Tula virus, Tupaia paramyxovirus, Usutu virus, Uukuniemi virus, Vaccinia virus, Variola virus, Venezuelan equine encephalitis virus, Vesicular stomatitis Indiana virus, WU Polyomavirus, Wesselsbron virus, West Caucasian bat virus, West Nile virus, Western equine encephalitis virus, Whitewater Arroyo mammarenavirus, Yellow fever virus, Yokose virus, Yug Bogdanovac virus, Zaire ebolavirus, Zika virus, or *Zygosaccharomyces bailii* virus Z viral sequence. In certain example embodiments, the probe set comprises probes for hybrid selection that bind all of the viruses listed in this paragraph. In certain example embodiments, the probe set comprises one of more SEQ ID NOs: 12,343-362, 340. In certain other example embodiments, the probe set consists of SEQ ID NOs: 12,343-362,340.

In certain example embodiments, the viral sequence may be an Cjolungua. Crimean-Congo, Dengue, Ebola non-Zaire, Ebola Zaire, GB virus C, Hepatitis A, Hepatitis C, HIV-1, HIV-2, Influenza A, Influenza B, Lassa, Marburg, Measles, MERS, Rhabdovirus, Rift Valley fever, SARS, Yellow fever or a mixture thereof. The Ebola viral sequence may be an Ebola Zaire, Bundibugyo, Sudan, Reston and Tai Forest sequence, or a mixture thereof. The hepatitis viral sequence may be a hepatitis A, hepatitis B or hepatitis C viral sequence, or a mixture thereof. The influenza viral sequence may be an influenza A or influenza B viral sequence, or a mixture thereof. The HIV viral sequence may be a HIV 1 or HIV 2 viral sequence, or mixture thereof. The target sequence may be a genome. In certain example embodiments, the probe set may comprise probes for hybrid selection that bind all probes in this paragraph. In certain example embodiments, the probe set may comprise one or more of SEQ ID NOs: 362,341 to 452,330. In certain other example embodiments, the probe set may consist of SEQ ID NOs: 362,341 to 452,330.

In certain example embodiments, the viral sequence may be Zika and/or Chikungunya. In certain example embodiments, the probe set may comprise probes that detect multiple variants of Zika and/or Chikungunya. In certain example embodiments, the probe set may comprise one or more of SEQ ID NOs: 1 to 12,342. In certain other example embodiments, the probe set may consist of SEQ ID NOs: 1 to 12,342.

Bait design may be performed similarly as previously described (see, e.g., Gnirke, et al., Nature biotechnology 27:182-189, 2009, US patent publications No. US 2010/0029498, US 2013/0230857, US 2014/0200163, US 2014/0228223, and US 2015/0126377 and international patent publication No. WO 2009/099602). As used herein, the terms "bait sequence" and "candidate probe" may be used interchangeably and each may be further appended with adaptor oligonucleotides.

Typically bait sequences are designed from reference sequences, such that the baits are optimal for catching targets of the reference sequences. However, in some embodiments, bait sequences are designed using mixed bases or a universal base such as inosine or 5-nitroindole (i.e., degeneracy). For example, the mixed or universal base(s) can be included in the bait sequence at the position(s) of a common SNP or mutation, to optimize the bait sequences to catch both alleles (i.e., SNP and non-SNP; mutant and non-mutant). In other embodiments, all known sequence variations (or a subset thereof) can be targeted with multiple oligonucleotide baits, rather than by using mixed degenerate oligonucleotides.

The bait sequences in some embodiments are synthetic long oligonucleotides or are derived from (e.g., produced using) synthetic long oligonucleotides. In certain embodiments, the set of bait sequences is derived from oligonucleotides synthesized in a microarray and cleaved and eluted from the microarray.

In some embodiments, the bait sequences in the set of bait sequences are RNA molecules. In some embodiments the bait sequences are chemically or enzymatically modified or in vitro transcribed RNA molecules including but not limited to those that are more stable and resistant to RNase.

Bait sequences preferably are oligonucleotides between about 10 nucleotides and 1000 nucleotides in length, more preferably between about 50 nucleotides and 200 nucleotides in length, more preferably still between about 70 nucleotides and 140 nucleotides in length. In another preferred embodiment, oligonucleotides with non-naturally occurring linkages such as locked nucleic acid ("LNA") or peptide nucleotide acids between about 15 and 50 nucleotides are also contemplated. Intermediate lengths in addition to those mentioned above also can be used in the methods of the invention, such as oligonucleotides of about 10, 20, 30, 40, 50, 60, 70, 80, 90, 100, 110, 120, 130, 140, 150, 160, 170, 180, 190, 200, 210, 220, 230, 240, 250, 300, 400, 500, 600, 700, 800, and 900 nucleotides in length, as well as oligonucleotides of lengths between the above-mentioned lengths. For selection of exons and other short targets, preferred bait sequence lengths are oligonucleotides of about 50 to about 200 nucleotides, and more preferably about 70 to about 140 nucleotides. For selection of targets that are long compared to the length of the capture baits, such as genomic regions, preferred bait sequence lengths are typically in the same size range as the baits for short targets mentioned above, except that there is no need to limit the maximum size of bait sequences for the sole purpose of minimizing targeting of adjacent sequences. In certain embodiments of the foregoing methods, the number of bait sequences in the set of bait sequences is less than 1,000. In other embodiments, the number of bait sequences in the set of bait sequences is greater than 1,000, greater than 5,000, greater than 10,000, greater than 20,000, greater than 50,000, greater than 100,000, or greater than 500,000.

The invention also includes methods for producing a set of bait sequences. The methods include providing or obtaining a nucleic acid array (e.g., microarray chip) that contains a set of synthetic long oligonucleotides, and removing the oligonucleotides from the microarray (e.g., by cleavage or elution) to produce a set of bait sequences. Synthesis of oligonucleotides in an array format (e.g., chip) permits synthesis of a large number of sequences simultaneously, thereby providing a set of bait sequences for the methods of selection. The array synthesis also has the advantages of being customizable and capable of producing long oligonucleotides.

The hybridization bait sequences may be prepared from the whole genome of the target organism, for example, where the bait sequences are prepared by a method that includes fragmenting genomic DNA of the target organism (e.g., where the fragmented bait sequences are end-labeled with oligonucleotide sequences suitable for PCR amplification or DNA sequencing or where the bait sequences are prepared by a method including attaching an RNA promoter sequence to the genomic DNA fragments and preparing the bait by transcribing (e.g., using biotinylated ribonucleotides) the DNA fragments into RNA. The bait sequences may be prepared from specific regions of the target organism genome (e.g., are prepared synthetically). In certain embodiments, the bait sequences are labeled with an affinity tag. In certain example embodiments, the affinity tag is biotin, a hapten, or an affinity tag, or the bait sequences are generated using biotinylated primers, e.g., where the bait sequences are generated by nick-translation labeling of purified target organism DNA with biotinylated deoxynucleotides. In cases where the bait sequences are biotinylated, the target DNA can be captured using a streptavidin molecule attached to a solid phase. The bait sequences may be appended by adapter sequences suitable for PCR amplification, sequencing, or RNA transcription. The bait sequences may include an RNA promoter or are RNA molecules prepared from DNA containing an RNA promoter (e.g., a T7 RNA promoter).

In other embodiments, the set of bait sequences is produced using known nucleic acid amplification methods, such as PCR, or other amplification methods described herein or known to the skilled person. For example, a set of bait sequences (e.g., 10,000 bait sequences) can be specifically amplified using human DNA or pooled human DNA samples as the template, according to known methods, whereby spacing of the primers on the template sequence will dictate the length of the resulting oligonucleotide baits.

The invention also provides methods of producing a set of RNA bait sequences in which a set of bait sequences is produced as described above, an RNA polymerase promoter sequence at the end(s) of the bait sequences, and the RNA bait sequences are synthesized using RNA polymerase. In preferred embodiments, the RNA polymerase is a T7 polymerase, a SP6 polymerase, or a T3 polymerase. In other embodiments, the RNA polymerase promoter sequence is added at the ends of the bait sequences by re-amplifying the bait sequences, such as by PCR or other nucleic acid amplification methods.

Figure 2:
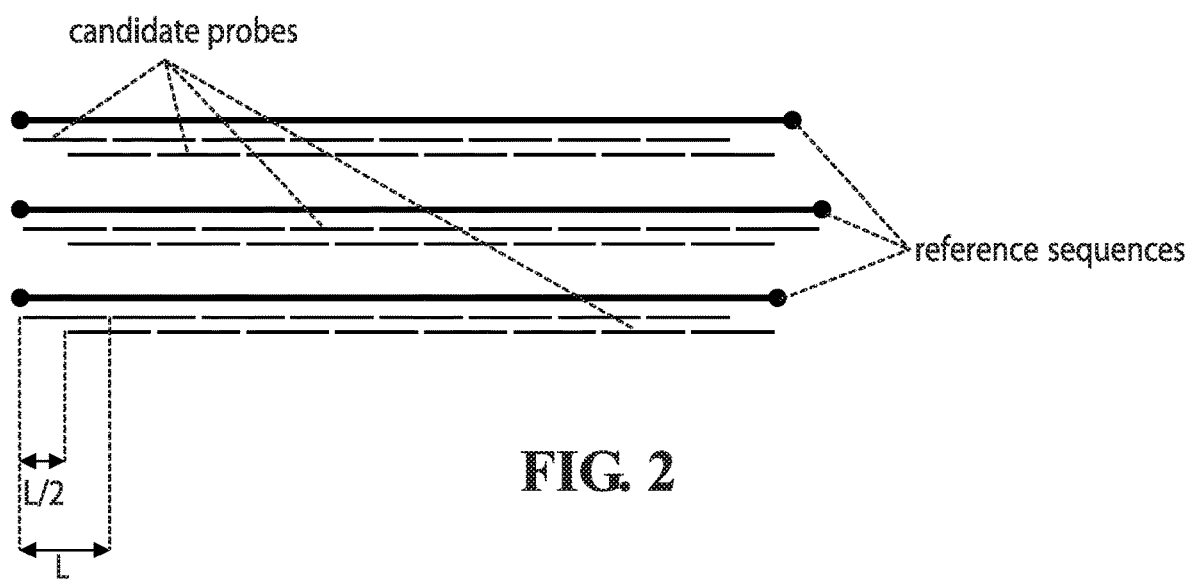
FIG. 2 shows a 2× tiling of candidate probes.

Constructing the candidate probes may comprise fragmenting the reference sequence into fragments of equal size that overlap one another, so that the overlap between two fragments is half the size of the fragment, for example a 2× tiling as illustrated in FIG. 2.

"Capable of hybridizing a reference sequence" is intended to mean capable of hybridizing the entire reference sequence or a fragment thereof.

"Individual hybridization pattern" is intended to designate the coverage capacity of one probe, i.e. the collection of subsequences of the reference sequence which the probe is capable of hybridizing or to which the probe is redundant. "Hybridization pattern along the length of the reference sequence" is intended to mean that the entire target sequence is covered. More generally, when used with respect to a plurality of probes, "hybridization pattern" is intended to designate the collective coverage capacity of the plurality of probes, i.e. the collection of subsequences of the reference sequence which at least one of the probes of the plurality of probes is capable of hybridizing or to which at least one of the probes is redundant.

Hybridization between the test sample and the bait sequence may be conducted under any conditions in which the bait sequences hybridize to the target organism's DNA (e.g., pathogen, commensal organism, or symbiont DNAs), but do not substantially hybridize to the contaminating DNA. This can involve selection under high stringency conditions. Following hybridization, the labeled baits can be separated based on the presence of the detectable label, and the unbound sequences are removed under appropriate wash conditions that remove the nonspecifically bound DNA, but do not substantially remove the DNA that hybridizes specifically.

In one embodiment, hybrid selection using either synthetic bait or whole genome baits (WGB) may be carried out as described previously (see, e.g., Gnirke, et al., Nature biotechnology 27:182-189, 2009, US patent publications No. US 2010/0029498, US 2013/0230857, US 2014/0200163, US 2014/0228223, and US 2015/0126377 and international patent publication No. WO 2009/099602).

In another embodiment, methods of US patent publication No. 2013/0190196 may be applied to detecting nucleic acid signatures, specifically RNA levels, directly from crude cellular samples with a high degree of sensitivity and specificity. Oligonucleotide probes to identify each pathogen of interest are selected by comparing the coding sequences from the pathogen of interest to all gene sequences in other organisms by BLAST software. Only probes of about 50 nucleotides, e.g., 80 nucleotides, 70 nucleotides, 60 nucleotides, 40 nucleotides, 30 nucleotides, and 20 nucleotides, with a perfect match to the pathogen of interest, but no match of >50% to any other organism are selected. Two probes corresponding to each mRNA of interest and within 100 base pairs of each other are selected.

As described in US patent publication No. 2013/0190196, two molecular probes are added to a crude sample lysate containing mRNA molecules. A capture probe comprises 50 nucleotides complementary to a given mRNA molecule, and can be conjugated to biotin. A reporter probe comprises a different 50 nucleotides complementary to a different part of the same mRNA molecule, and can be conjugated to a reporter molecule, e.g., a fluorescent tag or quantum dot. Each reporter molecule uniquely identifies a given mRNA molecule. The capture and reporter probes hybridize to their corresponding mRNA molecules within the lysate. Excess reporter is removed by bead purification that hybridizes to a handle on each oligomer, leaving only the hybridized mRNA complexes. The mRNA complexes can be captured and immobilized on a surface, e.g., a streptavidin-coated surface. An electric field can be applied to align the complexes all in the same direction on the surface before the surface is microscopically imaged. Such methods may also be applied to the present invention.

As described in US patent publication No. 2013/0190196, in an example involving tuberculosis (TB), wherein unique expression signatures for the detection of TB over other mycobacteria species have been defined. In general, the optimal genes for inclusion in a signature will fulfill the criteria of 1. having high expression levels (high mRNA copy number) to increase sensitivity, 2. being highly conserved across all TB strains as well as having highly conserved sequence, and 3. being highly specific for TB genome over all other mycobacteria species. Such genes were identified using a bioinformatic analysis of conserved genes in the available TB genomes that are not present in all other sequenced mycobacteria species (i.e., *M. marinum, M. avium-intracellulare, M. kansasii, M. fortuitum*, M. *abscessus*). Over 40 TB genomes from clinically isolated strains that have been sequenced at the Broad Institute are available for analysis. A second criterion for selection of molecular probes for the detection of TB bacilli in sputum is that they hybridize to highly abundant, stable mRNAs to allow maximum sensitivity. Such mRNAs are anticipated to correspond to essential housekeeping genes. Genes have been selected using a combination of bioinformatic analysis of existing, publicly available expression data in a database created at the Broad Institute and Stanford University (tbdb.org) and experimental expression profiles on TB strain H37Rv using expression profiling to confirm a high level of expression of candidate genes under conditions permissive for replication (logarithmic growth) and non-replication induced by carbon starvation, stationary phase, and hypoxia. Expression profiling experiments on H37Rv are performed using a carbon starvation model of TB that has been established (starvation for 5 weeks in 7H9/tyloxapol), stationary phase growth, and the Wayne model for anaerobic growth (slowly agitated cultures in sealed tubes). Solexa/Illumina sequencing is used to determine expression profiles by converting mRNA to cDNA and using sequencing to count cDNA molecules. This quantitative method for identifying expression levels is more likely to reflect levels obtained using digital gene expression than microarray data and is a method that has been established with the Broad Institute Sequencing Platform. It is possible to multiplex 12 samples per sequencing lane given 75 bp reads and 10 million reads per lane. Because the digital gene expression technology is based on the hybridization of two 50 nucleotide probes to the mRNA of interest, two 50 base pair regions in the genes are identified from (Ai) and (Aii) that are unique within the genome to minimize non-specific hybridization and that contain minimal polymorphisms as evidenced from sequenced TB genomes. The probes are selected bioinformatically to fit within a 5 degree melting temperature window and with minimal mRNA secondary structure. The probes are tested against mRNA isolated from replicating and non-replicating TB (including multiple strains i.e., H37Rv, CDC1551, F11, Erdman), *M. marinum, M. avium-intracellulare, M. kansasii*, and *M. fortuitum* to confirm the specificity of the entire probe set using available technology. Probes may be selected for these other mycobacterial species, which will allow for identification of these pathogens from sputum as well. The ability to identify intracellular bacilli is tested in a macrophage model of infection, to demonstrate the ability to detect TB mRNA in the presence of host mRNA. Finally, the sensitivity of the assay was determined by titrating down the number of TB bacilli (and thus mRNA present in cell lysates) in the sample tested. All experiments using digital gene expression is confirmed using quantitative RT-PCR against the same gene set. Improvement and refinement of the set occurs in an iterative manner. Such methods may also be applied to the present invention.

Figure 3:
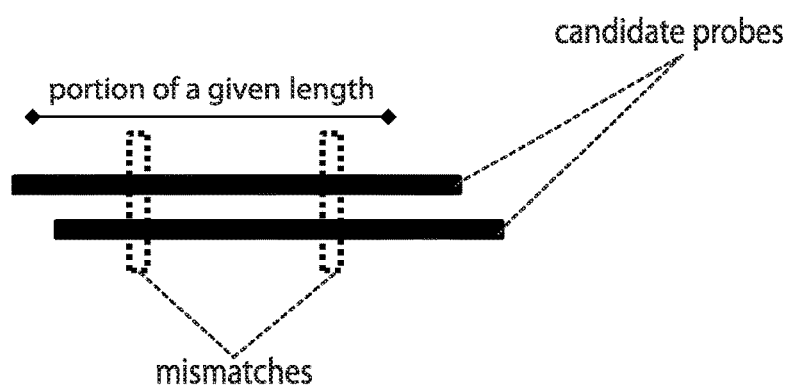
FIG. 3 shows that two probes may be said to be redundant if each of them presents a portion of a given length that is the same as the portion of a given length of the other probe, wherein the portions are considered the same even if there are up to a threshold number of mismatch.
Figure 4:
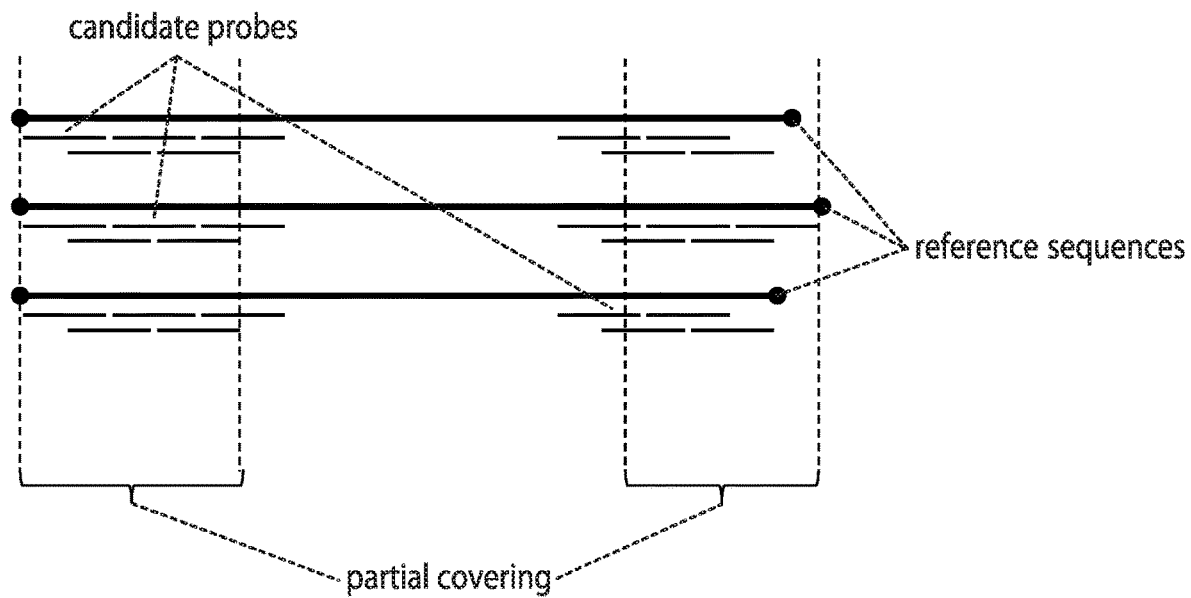
FIG. 4 shows an example in the case of tiling where the target sequence is only tiled on desired portions.

Two probes may be said to be redundant if each of them presents a portion of a given length that is the same as the portion of a given length of the other probe, wherein the portions are considered the same even if there are up to a threshold number of mismatch (see FIG. 3). Therefore, in comparison with the prior art, no criterion on the shift is taken into consideration, what is a result of the set cover solving process. The number of allowed mismatches may be 0, 1, 2, 3, 4, 5, 6, 7, 8, 9 or up to given length of the probe.

The present invention also encompasses tiling methods to obtain desirable probes for mixed samples and measurements that advantageously may not involving sequencing. For example, the nanoString® nCounter® lncRNA assays may be contemplated for analyzing and quantifying RNAs of the present invention. A microarray based upon Affymetrix Axiom genotyping technology (see, e.g., Hoffman et al., Genomics. 2011 August; 98(2): 79-89) is also contemplated, in particular, for identifying SNPs and polymorphisms. The invention also encompasses use of a SureSelect Target Enrichment System developed by Agilent Technologies, a SeqCap EZ target capture kit developed by Roche Nimble-Gen, a TruSeq® Enrichment Kit developed by Illumina and other hybridization-based methods and kits for enriching sequencing targets of interest in a sample.

The set cover solving process does not even need a definition of redundancy between two candidate probes but rather the redundancy is between a probe and a region of a target sequence. The number of mismatches is an input to the program as a whole which is more directly used in determining a hybridization pattern rather than directly used in solving an instance of a set cover problem. While misalignments caused by indels (deletions or insertions) occurring within a population of target sequences were not considered in determining whether a candidate probe was redundant, this aspect could be considered.

The set cover solving process is any process that approximates the solution to the set cover problem or a problem equivalent to the set cover problem (see, e.g., Thomas H. Cormen, Charles E. Leiserson, Ronald L. Rivest, and Clifford Stein. 2009. Introduction to Algorithms 3rd ed. The MIT Press.; and Vijay Vazirani. 2001. Approximation Algorithms. Springer-Verlag, Berlin. The set cover problem may be described as follows: given a set of elements {1, 2 . . . i . . . m}, called the universe U, and a collection S of n subsets whose union covers the universe, the set cover problem is to identify the smallest set of subsets whose union equals the universe.

In the present invention, an element may be a nucleotide existing in a location within the reference sequence or sequences, the universe may be the reference sequence, each subset may be the individual hybridization pattern of a candidate probe, the union of the hybridization patterns of the candidate probes equals the reference sequence. Thus, the set cover solving process may approximate the smallest number of candidate probes that collectively have a hybridization pattern along the length of the reference sequence.

"Reference sequence" is intended to encompass the singular and the plural. As such, when referring to a reference sequence, the cases where more than one reference sequence is also contemplated. Preferably, the reference sequence is a plurality of reference sequences, the number of which may be over 30; 50; 70; 100; 200; 300; 500; 1,000 and above. In certain example embodiments, the reference sequence is a genomic sequence. In certain example embodiments, the reference sequence is a plurality of genomic sequences. In certain example embodiments, the reference sequence is a plurality of genomic sequences from the same species or viral strain. In certain other example embodiments, the reference sequence is a plurality of genomic sequences from different species or viral strains.

The set cover solving process makes it possible to reduce substantially, if not dramatically, the number of selected probes that are needed to analyze a sample. Preferably, the number of selected probes is over 700; 900; 1,000; 1,400; 1,600; 2,000; 2,400; 2,700; 3,000; 3,500; 4,000; 4,700; 5,000; 5,300; 7,500; 10,000; 13,000; 15,000; 65,000; preferably lower than 90,000. In certain example embodiments, the number of selected is probes is between 100,000 to 500,000.

In one embodiment, the reference sequence may be a collection of genomes of one type of virus, the genomes collectively form a universe of elements that are the nucleotides (position within the genomes being considered as differentiating nucleotides of the same type). In another embodiment, each genome may make up one universe so that the problem as a whole becomes a multi-universe problem. Multi-universe may be a unique generalization of the set cover problem. In this instance, separate universes may be helpful for thinking about partial set cover, so this way a partial cover yields a desired partial coverage of each genome (i.e., each universe). If the problem is imagined as being composed of a single universe, thinking about partial coverage may be considered as covering a desired fraction of the concatenation of all the genomes, rather than a desired fraction of each genome.

If X designates a genome and y designates a position within the corresponding genome, an element of the universe can be represented by (X, y), which is understood as the nucleotide in position y in genome X. Candidate probes are obtaining by fragmenting the collection of genomes. The individual hybridization patterns are subsets of the universe. The individual hybridization pattern of a candidate probe of length L can be represented as {(A, ai), (A, ai+1) . . . (A, ai+L), (A, aj), (A, aj+1) . . . (A, aj+L), (B, bi), (B, bi+1) . . . (B, bi+L) . . . }, otherwise represented as {A: (ai . . . ai+L), (aj . . . aj+L); B:(b1 . . . b1+L) . . . } (subset covering nucleotides in position ai to ai+L and aj to aj+L in genome A, nucleotides in position bi to bi+L in genome B . . . ).

In certain example embodiments, a set of target sequences are provided. In certain example embodiments the target sequences are variants of a single species. In certain other example embodiments, the target sequences are from multiple different species. In certain example embodiments, the target sequences are viral sequences. The viral sequences may be variants of the same viral strain, different viruses, or a combination thereof. A hybridization pattern is determined for the target sequences. To model a hybridization pattern a number of different parameters may be defined to determining whether a given probe is considered to hybridized to a given portion of a target sequence or sequences. In addition, a percent of coverage parameter may be set to define the percent of the target sequence that should be covered by the probe set. This value may range from a fraction of a percent to 100% of the genome. In certain example embodiments this may range from 0.01% to 10%, 1% to 5%, 1% to 10%, 1% to 15%, 1% to 20%, 1% to 25%, 1% to 30%, 1% to 35%, 1% to 40%, 1% to 45%, 1% to 50%, 1% to 55%, 1% to 60%, 1% to 65%, 1% to 70%, 1% to 75%, 1% to 80%, 1% to 85%, 1% to 90%, 1% to 95%, 1% to 100%. 50% to 100%, 55% to 100%, 60% to 100%, 65% to 100%, 70% to 100%, 75% to 100%, 80% to 100%, 85% to 100%, 90% to 100%, or 95% to 100%.

In certain example embodiments, a number of mismatch parameters is defined. The number of mismatches defines a number of mismatches that may be present between a probe and a given portion of a target sequence. This value may range from 0 to 10 base pairs.

In certain example embodiments, another parameter, called the "island of exact match" 1ubstring" may be used to model hybridization between a probe and nucleic acid fragment. Let its value be x. When determining whether a probe covers a sequence, a value is set that defines a stretch of at least x bp in the probe that exactly matches (i.e., with no mismatches) a stretch of a target sequence. Along with the other parameters, this is applied as a filter to decide whether a probe should be deemed as hybridizing to a portion of a target sequence. The value may vary, but usually set it to be 30 bp. Setting its value to 0 would effectively remove this filter when determining hybridization patterns.

In certain other example embodiments, a longest common substring parameter may be set. This parameter defines that a probe only hybridizes only if the longest common substring up to a certain amount of mismatches is at least that parameter. For example if the parameter is set to 80 base pair with 3 mismatches, then a probe will still be considered to hybridized to a portion of a target sequence if there is string of 80 base pairs that match the target sequence even if within that stretch there are up to 3 mismatches. So a 80 base pair sting that matches except for two mismatches would be considered to hybridized but an 80 base pair string that matches except for 4 mismatches would not be considered to hybridize. This parameter may range from a string of 20 to 175 base pairs with anywhere from 0 to 9 mismatches in that string.

In certain other example embodiments, an overhang or cover extension parameter may be set. This parameter indicates that once a probe is found to hybridize, that probe will be considered to cover, or account for, X additional base pairs upstream and down stream of where the probe has bound. This parameter allows the number of total probes required to be reduced further because it will be understood that a probe, e.g. 100 base pair, will not only account for the 100 base pairs portion it directly binds to but may be reliably considered to capture a fragment that is at least 50 base pairs longer than the 100 base pair string. This parameter may vary between 0 and 200. In certain example embodiments, this parameter is set to 50.

This can be used, for example, in sequencing genomes of a virus for which a collection of genomes is available from previous studies, such as Ebola Zaire virus. The collection of available genomes from previous studies is taken as reference target. One aim may be the study and monitoring of the evolution of the virus, for example throughout an outbreak in order to determine proper actions to be taken for containing the outbreak and stopping it by sequencing regularly, if not systematically, the genome of the virus that infects a patient known to have contracted it.

The set cover solving process may be a weighted set cover solving process, i.e. each of the individual hybridization patterns is allocated a weight.

For example, a lower weight is allocated to those individual hybridization patterns that correspond to candidate probes that are specific to the target sequence and a higher weight is allocated to those individual hybridization patterns that correspond to candidate probes that are not specific to the target sequence. Thus, the method may further comprise determining the specificity of each candidate probe with regard to the target sequence. For example, determining the stringency of hybridization may be indicative of the specificity of the candidate probes. The higher weight is determined based on when a probe hybridizes to some other reference sequence (not a target), e.g., when blacklisting genomes or when doing identification. Another mismatch parameter may be utilized when assigning higher weights, which is usually a looser and more tolerant value. For example, there may be a mismatch parameter with a value of 3 for determining whether a probe hybridizes to a region of a target sequence, but a separate tolerant mismatch parameter with a value of 10 for determining whether a probe hits a blacklisted sequence or more than one virus type in identification. The reason is desired increased sensitivity in determining these kinds of hits and more specificity in determining where probes cover target sequences.

The weighted set cover solving process makes it possible to reduce substantially, if not dramatically, the number of selected probes needed to deplete one or more contaminants contained in the sample. Indeed, as mentioned above, the target sequences usually amount to only a small fraction of the sample. Thus, it might be interesting to generate selected probes that do not hit or hybridize one or more contaminants or fragments thereof. The one or more contaminants may be considered as blacklisted sequence or sequences that are unwanted and the analysis of which is not contemplated. To this aim, a higher weight is allocated to those individual hybridization patterns corresponding to candidate probes that hit at least one blacklisted sequence. "Hit" is intended to mean that the candidate probes linked to the blacklisted sequence, for example by hybridizing it. When an individual hybridization pattern is allocated a higher weight, it does not necessarily mean that the corresponding candidate probe is dismissed from being selected.

In this aim, the method may further comprise determining which candidate probes are specific to the target sequence and which candidate probes are not. For example, determining the stringency of hybridization may be indicative of the specificity of the candidate probes. The higher weight is determined based on when a probe hybridizes to some other reference sequence (not a target), e.g., when blacklisting genomes or when doing identification. Another mismatch parameter may be utilized when assigning higher weights, which is usually a looser and more tolerant value. For example, there may be a mismatch parameter with a value of 3 for determining whether a probe hybridizes to a region of a target sequence, but a separate tolerant mismatch parameter with a value of 10 for determining whether a probe hits a blacklisted sequence or more than one virus type in identification. The reason is desired increased sensitivity in determining these kinds of hits and more specific in determining where probes cover target sequences.

Thus, the reference sequence forms a universe of elements that are the nucleotides (position within the genomes being considered as differentiating nucleotides of the same type). If X designates the reference sequence and y designates a position within the corresponding genome, an element of the universe can be represented by (X, y), which is understood as the nucleotide in position y in the reference sequence X, or simply (y) because all y belongs to the same reference sequence. Candidate probes are obtaining by fragmenting the reference sequence. It is then determined which candidate probes are specific to the target sequence and which are not. The individual hybridization patterns are subsets of the universe. The individual hybridization pattern of a candidate probe of length L and which is specific to the target sequence can be represented as (w, {(ai), (ai+1) ... (ai+L), (aj), (aj+1) ... (aj+L)}), otherwise represented as (w, {(ai ... ai+L), (aj aj+L)}) (subset covering nucleotides in position ai to ai+L ... and aj to aj+L to which a weight w is given). The individual hybridization pattern of a candidate probe of length L and which is not specific to the target sequence would be represented in the same manner but will receive weight W instead, wherein W>w, preferably W>>w, more preferably W is infinity and w is 1.

If the reference sequence is a collection of reference sequences, then the individual hybridization pattern of a candidate probe of length L and which is specific to the target sequence can be represented as (V, {(A, ai), (A, ai+1) ... (A, ai+L), (A, aj), (A, aj+1) ... (A, aj+L), (B, bi), (B, bi+1) ... (B, bi+L)}), otherwise represented as (V, {A:(ai ... ai+L), (aj ... aj+L); B:(bi ... bi+L) ... }) (subset covering nucleotides in position ai to ai+L and aj to aj+L in genome A, nucleotides in position bi to bi+L in genome B ... to which a weight V is given).

Allocating the same weight to all the individual hybridization patterns amounts to an un-weighted set cover solving process, in other words a set cover solving process without allocation of any weight such as described above. Both weighted set cover solving process and un-weighted set cover solving process are contemplated by the invention.

A higher number of allowed mismatches than for the un-weighted set cover solving process may be used, which is considered to be a separate, more tolerant parameter choice—in addition to the regular mismatch parameter that would be used (in the un-weighted problem) for determining hybridizations to target sequences. But, if the higher number does not replace the lower number; it is an additional parameter.

The set cover solving process may be a partial set cover solving process, i.e. a full coverage of the target sequence is not necessary so that a desired percentage of coverage of the target sequence is sufficient. In other words, the selected probes collectively have a hybridization pattern that covers a desired portion of the hybridization pattern. This approach may be useful for such purposes as identifying consensus regions between target sequences or alternatively of identifying highly variant regions between target sequences, for example for the purposes of SNP profiling. The percentage of coverage may be between 0%-100% or any range in between, for example the percentage of coverage may be from 1% to 99%, from 2% to 98%, from 5% to 95%, from 10% to 90%, from 20% to 80%, from 30% to 70%, from 40% to 60%, or about 50%. The percentage of coverage is advantageously about 0% to 10% for identification of shorter highly conserved regions or shorter highly variable regions or about 90% to about 100% over a full genome. The partial coverage may be determined at the step of constructing candidate probes capable of hybridizing a reference sequence. The input genomes may be modified to be just a portion of the original, and the set cover solving process could cover all 100% of that input. This could effectively yield a partial coverage of the original genomes. However, it is desirable to provide the entire (full) genomes, and supply some desired partial coverage as an initial parameter. The candidate probes are typically not affected by this partial coverage parameter (i.e., there are no fewer) as it is the set cover solution that decides which candidate probes to select to achieve the partial cover.

The set cover solving process may be a weighted partial set cover solving process, i.e. each of the individual hybridization patters is allocated a weight and a full coverage of the target sequence is not necessary so that a percentage of coverage of the target sequence is sufficient.

The weighted partial set cover solving process is a powerful tool to reduce substantially, if not dramatically, the number of selected probes that are needed to discover which target sequence is present in a given sample that may comprise a plurality of different sequences, potentially thousands of different sequences; e.g. a biological sample potentially which may comprise viral sequences of different viruses.

A way to do so is to allocate a higher weight to individual hybridization patterns corresponding to candidate probes that hit sequences of more than one species of virus or fragments thereof and to a lower weight to individual hybridization patterns corresponding to candidate probes that hit sequences of only one species of virus or fragment thereof. Preferably, the higher weight is infinite and the lower weight is 1. This results in the selected probes coming from regions of the sequences that is conserved within one species but divergent from other species.

One example of a process that approximates the solution to the set cover problem is the greedy method. The greedy method is an iterative method wherein at each iteration the solution that appears the best is chosen. When applied to the set cover problem, at each iteration the subset with the widest coverage of the yet uncovered universe is selected and the elements covered by the subset with the widest coverage are deleted from the yet uncovered universe. This is repeated until all the selected subsets collectively cover the entire universe, in other words the yet uncovered universe is empty.

Within the scope of the invention, this means that, at each iteration, the candidate probe with the widest individual hybridization pattern within yet uncovered portions of the reference sequence is selected as one of the selected probes. The selection is repeated amongst the remaining candidate probes until the selected probes collectively have a hybridization pattern along the length of the reference sequence, or in other words there are no more uncovered portion of the reference sequence.

Alternatively, in the case of partial set cover solving process or weighted partial set cover solving process, the iteration is repeated until the selected probes collectively have a hybridization pattern of a given percentage P of the reference sequence, i.e. P percent of the reference sequence is covered by the collective hybridization pattern of the selected probes.

Thus, compared to previous methods, where the list of probes is built down by eliminating unwanted candidate probes therefrom, the set cover solving process makes it possible to build up the list of selected probes by adding one selected probe to the list at each iteration.

What has been described for virus sequences also holds true for bacteria sequences or any other pathogenic sequences such as fungal sequences.

The method may further comprise minimizing a loss function depending on overhang parameters and mismatch parameters (or any parameters that alters the number of output probes) such that the total number of selected probes is no higher than a threshold number to provide input parameters to the set cover solving process. An overhang parameter ("cover extension") determines the number of nucleotides of one or both ends of a target sequence or a fragment thereof that remain unpaired once the target sequence or the fragment thereof hybridizes a selected probe. The higher the overhang parameter is, the lower the number of selected probes output by the set cover solving process. The value of the overhang parameters can range from 0 to 200 bp; and any sub-range therein. A mismatch parameter is the acceptable number of mismatches between a selected probe and the target sequence or the fragment thereof. The higher the mismatch parameter is, the lower the number of selected probes. In certain example embodiments, the mismatch parameter may have a range from 0 to 9.

In case of a plurality of target sequence types, one overhang parameter and one mismatch parameter is assigned to each target sequence or types thereof. The values of the overhang and mismatch parameters may be indicative of the diversity of the target sequence especially when selecting these parameters under the constraint of having a fixed number of probes.

The loss function is constructed so that the higher the value of the overhang parameter, the higher the value of the loss function and the higher the value of the mismatch parameter, the higher the value of the loss function.

The use of a constraint while minimizing the loss function ensures that the number of selected probes remains lower than a reasonable amount depending on the application of the selected probes. The desired coverage is usually fixed, which is indeed a parameter, separately (since there is less flexibility about it).

Step (b1) and (c1) of the method may be respectively replaced by (b2) assessing redundancy between candidate probes and (c2) subjecting the candidate probes to a dominating set solving process to reduce the number of candidate probes to provide a selected probes, any candidate probe being either a selected probe or redundant to a selected probe.

Figure 5:
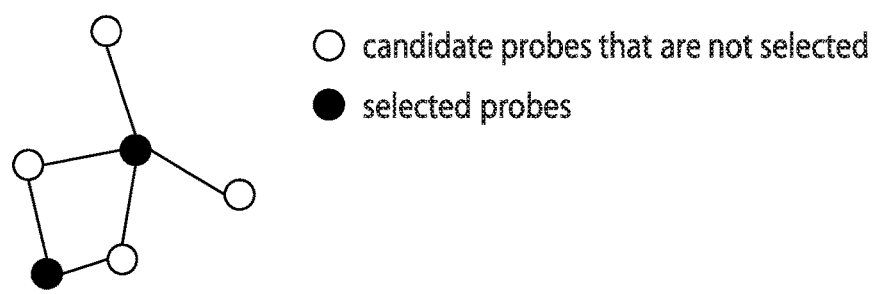
FIG. 5 shows one graph and one solution of the dominating set problem.
Figure 6:
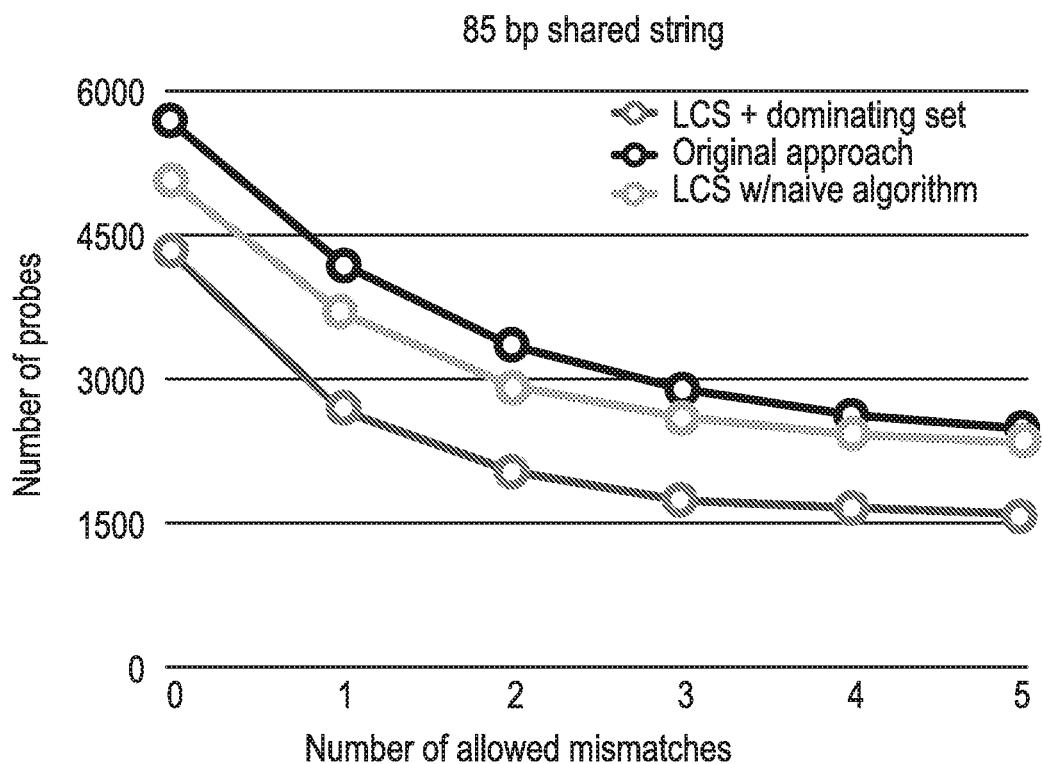
FIGS. 6-11 graphically show the number of selected probes generated as output of Example 1.1, Example 1.2 and Comparative example 1.
Figure 7:
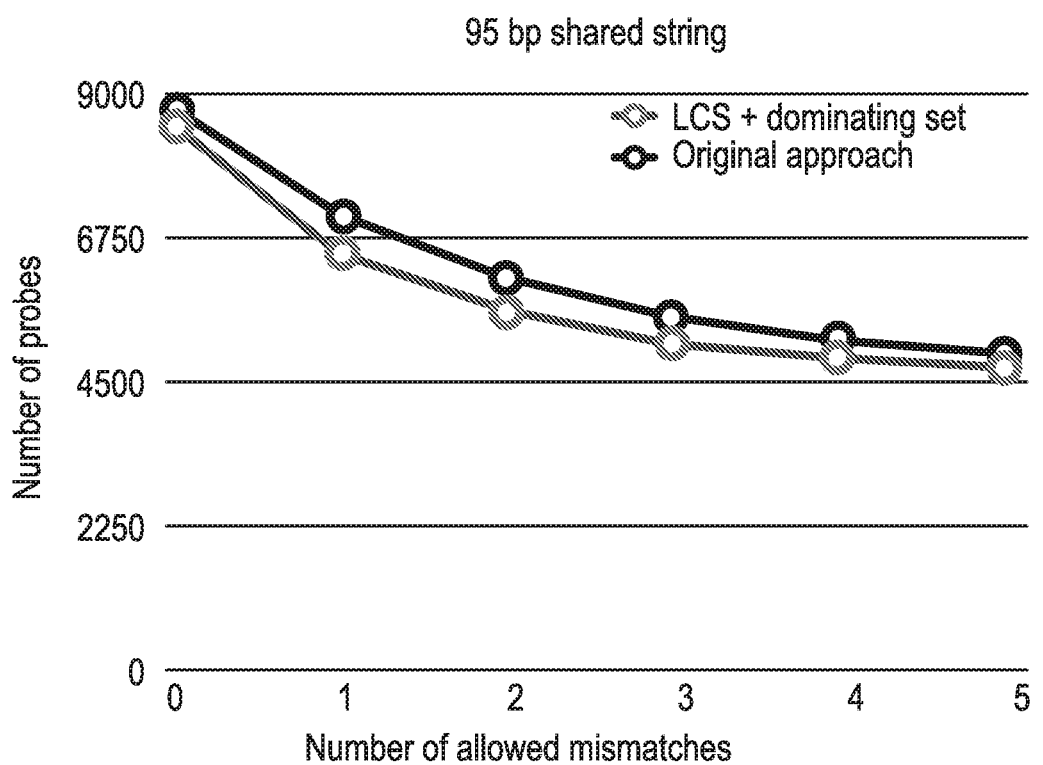
Figure 8:
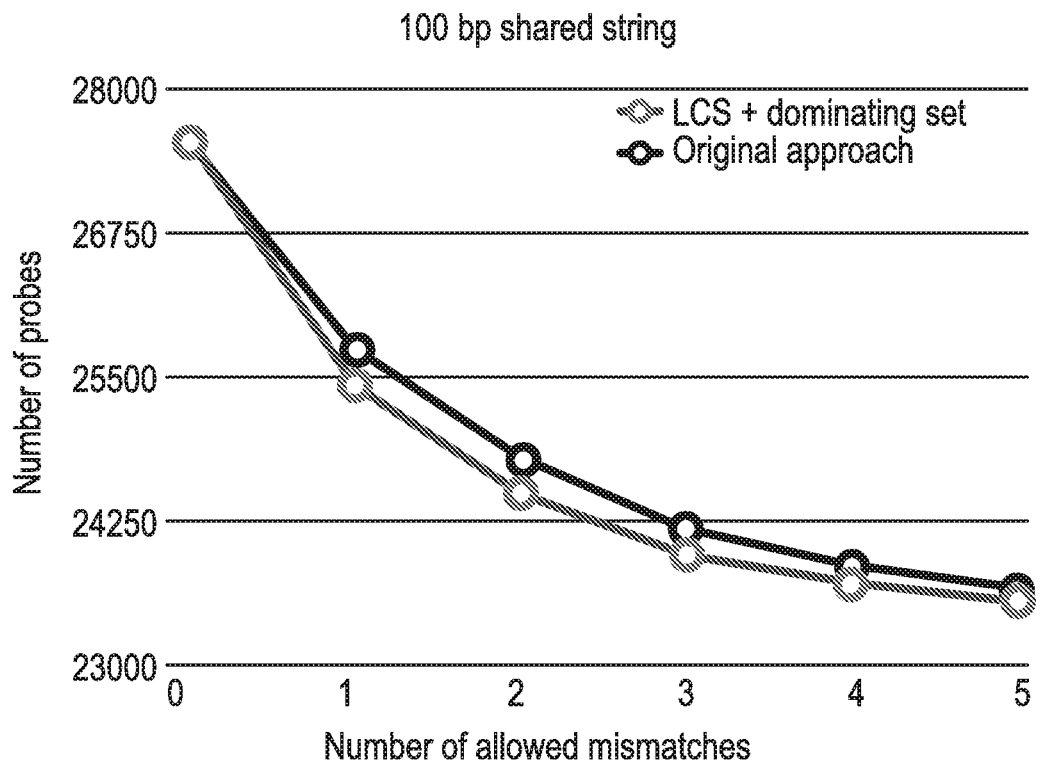
Figure 9:
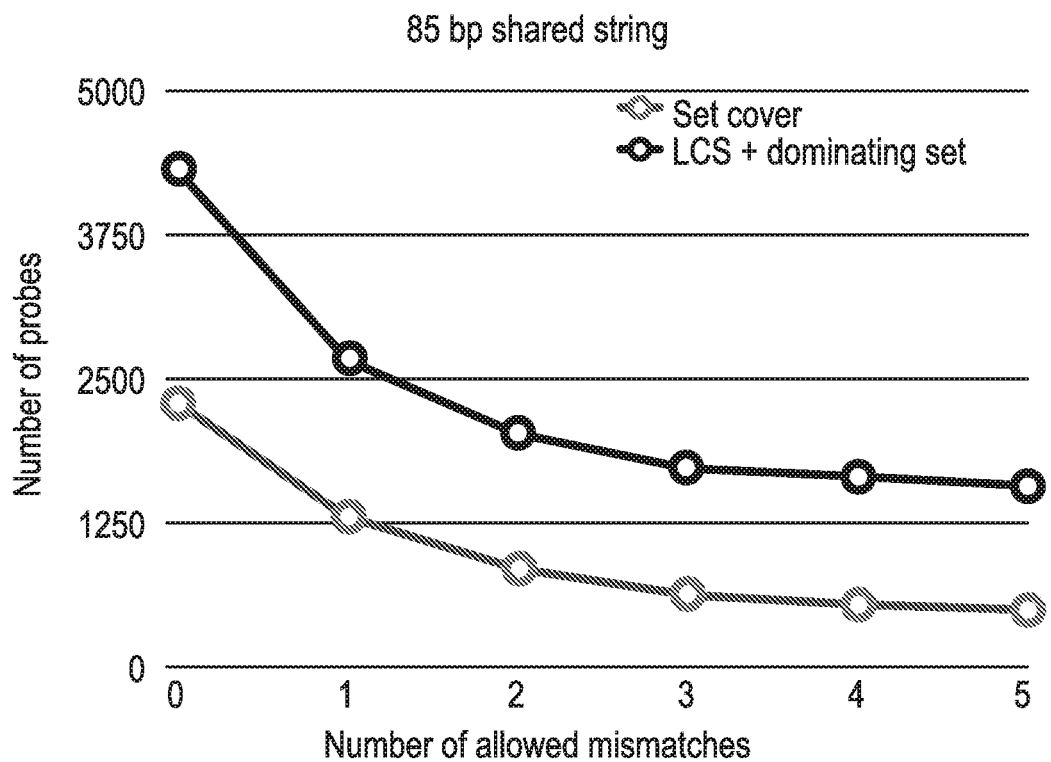
Figure 10:
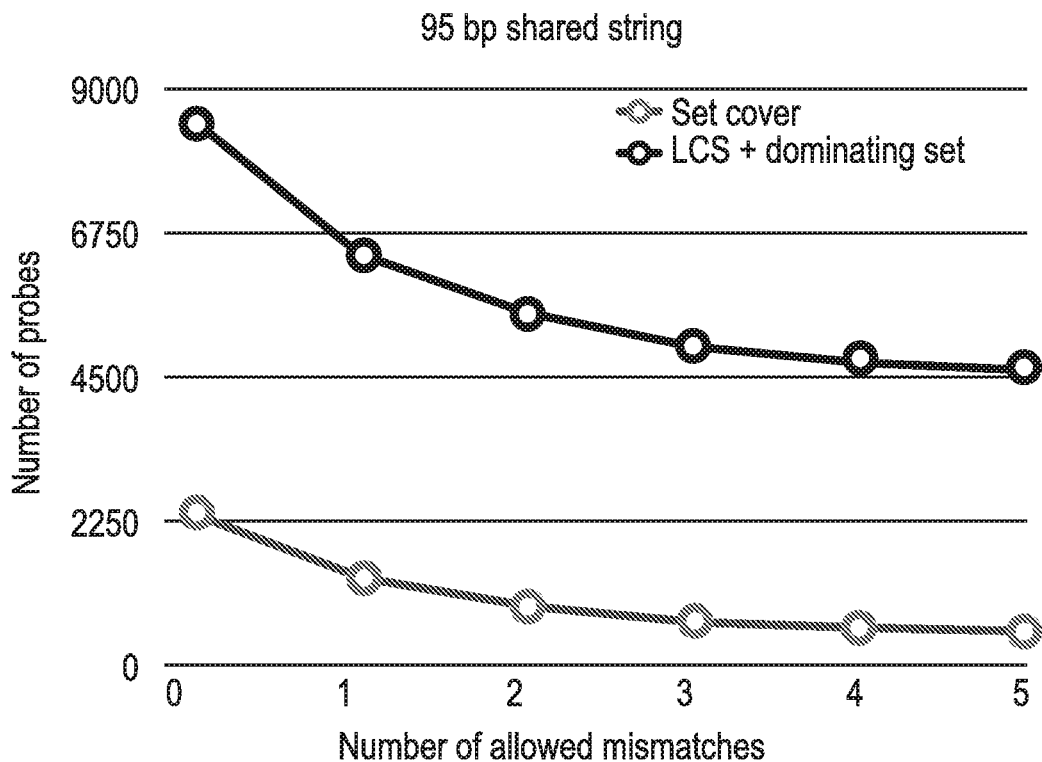
Figure 11:
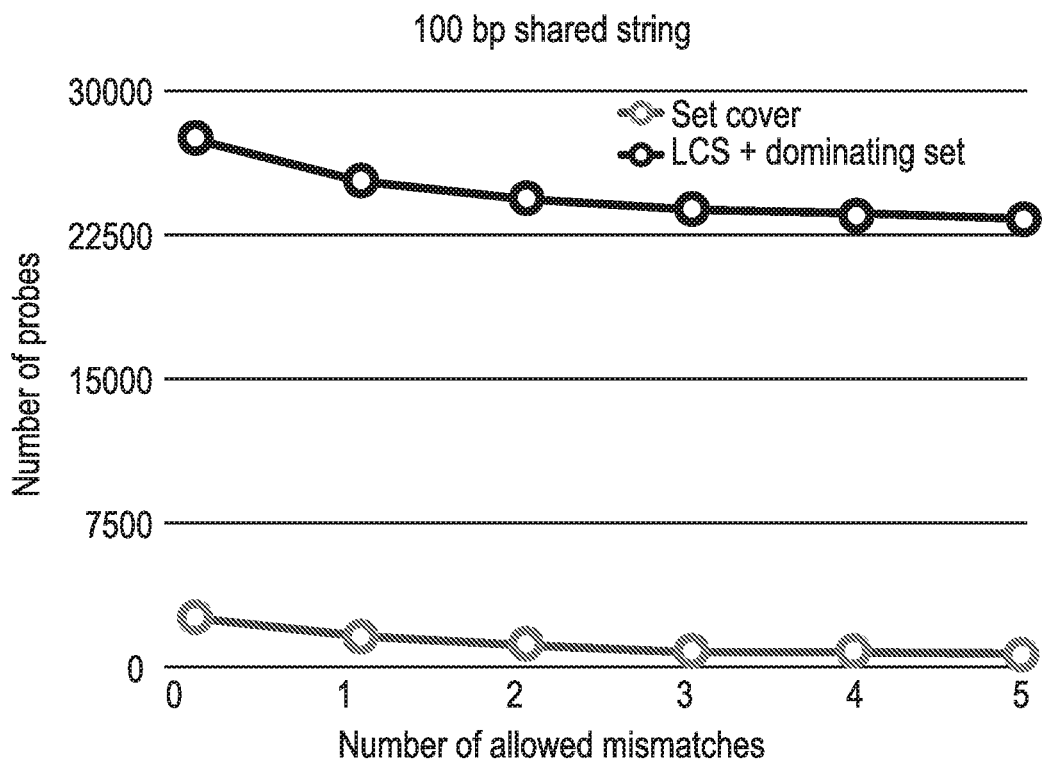

The solving process may further be a dominating set solving process, which solves the dominating set problem. The dominating set problem concerns a graph with a number of nodes linked to each other according to a certain pattern. The graph may comprise vertices and edges connecting two vertices to each other (FIG. 5 showing one graph and one solution of the dominating set problem). The dominating set problem may be described as finding a minimal set of vertices D, call the dominating vertices, such that each vertex in the graph is either in D or is adjacent to a vertex in D. A practical solution to the problem would approximate the smallest number. In the case of the present invention, each candidate probe is a vertex and if two candidate probes are redundant to each other, they are connected together by an edge. The graph does not need to be actually built; it is only mentioned to provide a visual reference to the reader.

The dominating set solving process is a process that solves the dominating set problem or any problem equivalent to the dominating set problem. Other problems include, but not limited to, framing a set cover problem as an "integer linear program" ("ILP"), a type of model in optimization which shows how the solution can be approximated with a technique called "linear programming relaxation" ("LP relaxation"). Specifically, the kind of relaxation used is called "LP-rounding" which is an example of another (non-greedy) way to approximate a solution to the set cover problem. (see, e.g., Chapter 13 and 14 of "Approximation Algorithms" by Vijay Vazirani. The article "On the hardness of approximating minimization problems" by Lund and Yannakakis (Lund, Carsten & Yannakakis, Mihalis. (1994). On the Hardness of Approximating Minimization Problems. J. ACM. 41. 960-981 lists some other problems 'equivalent' to set cover and also includes one of the first 'inapproximability results' for set cover. Unless certain widely believed conjectures in math turn out to be false, no method can give a solution to the problem that is "too much better" than the one given by the greedy algorithm. The result of another method cannot be better than the greedy algorithm by anything more than a constant factor.

The selected probes can be used in a composition form, as part of a kit or a system for enrichment of genomic DNA of a target organism in a sample that may comprise both DNA of the target organism and non-specific DNA. The kit may comprise the selected probes, e.g. in a composition form, and a solid phase operably linked to the selected probes. The system may comprise the selected probes, i.e. in a composition form; a sample containing DNA of said target organism and the non-specific DNA; and a solid phase operably connected to the selected probes.

The solid phase may be a chip or beads. The selected probes may further comprise an adapter, for example a label. Each selected probes may comprise two adapter. Preferably, a first adapter is alternated with a second adapter.

The selected probes that are generated by the method for generating probes for use in analyzing a sample which may comprise a target sequence described above can be used in a method of analyzing a sample which may comprise a target sequence or a fragment thereof. This method may comprise (a) contacting the selected probes to the target sequence or a fragment thereof; and (b) analyzing the target sequence or fragment thereof that hybridizes to one or more of the selected probes.

Analyzing the target sequence or fragment thereof that hybridizes to one or more of the selected probes may be a sequencing analysis further which may comprise sequencing the target sequence or fragment thereof that hybridizes to one or more of the selected probes. Various sequencing processes may be used and are described as follows.

RNA sequencing (RNA-Seq) is a powerful tool for transcriptome profiling, but is hampered by sequence-dependent bias and inaccuracy at low copy numbers intrinsic to exponential PCR amplification. To mitigate these complications to allow truly digital RNA-Seq, a large set of barcode sequences is added in excess, and nearly every cDNA molecule is uniquely labeled by random attachment of barcode sequences to both ends (Shiroguchi K, et al. Proc Natl Acad Sci USA. 2012 Jan. 24;109(4):1347-52). After PCR, paired-end deep sequencing is applied to read the two barcodes and cDNA sequences. Rather than counting the number of reads, RNA abundance is measured based on the number of unique barcode sequences observed for a given cDNA sequence (Shiroguchi K, et al. Proc Natl Acad Sci USA. 2012 Jan. 24;109(4):1347-52). The barcodes may be optimized to be unambiguously identifiable, even in the presence of multiple sequencing errors. This method allows counting with single-copy resolution despite sequence-dependent bias and PCR-amplification noise, and is analogous to digital PCR but amendable to quantifying a whole transcriptome (Shiroguchi K, et al. Proc Natl Acad Sci USA. 2012 Jan. 24;109(4):1347-52).

Fixation of cells or tissue may involve the use of cross-linking agents, such as formaldehyde, and may involve embedding cells or tissue in a paraffin wax or polyacrylamide support matrix (Chung K, et al. Nature. 2013 May 16; 497(7449): 322-7).

Amplification may involve thermocycling or isothermal amplification (such as through the methods RPA or LAMP). Cross-linking may involve overlap-extension PCR or use of ligase to associate multiple amplification products with each other.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. A preferred amplification method is PCR. In particular, the isolated RNA can be subjected to a reverse transcription assay that is coupled with a quantitative polymerase chain reaction (RT-PCR) in order to quantify the expression level of a sequence associated with a signaling biochemical pathway.

Detection of the gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double stranded DNA molecules is typically proportional to the amount of the amplified DNA products, one can conveniently determine the amount of the amplified products by quantifying the fluorescence of the intercalated dye using conventional optical systems in the art. DNA-binding dye suitable for this application include SYBR green, SYBR blue, DAPI, propidium iodine, Hoeste, SYBR gold, ethidium bromide, acridines, proflavine, acridine orange, acriflavine, fluorocoumarin, ellipticine, daunomycin, chloroquine, distamycin D, chromomycin, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence specific detection of a desired amplified product. It utilizes fluorescent, target-specific probes (e.g., TaqMan® probes) resulting in increased specificity and sensitivity. Methods for performing probe-based quantitative amplification are well established in the art and are taught in U.S. Pat. No. 5,210,015.

Sequencing may be performed on any high-throughput platform with read-length (either single- or paired-end) sufficient to cover both template and cross-linking event UID's. Methods of sequencing oligonucleotides and nucleic acids are well known in the art (see, e.g., WO93/23564, WO98/28440 and WO98/13523; U.S. Pat. Nos. 5,525,464; 5,202,231; 5,695,940; 4,971,903; 5,902,723; 5,795,782; 5,547,839 and 5,403,708; Sanger et al., Proc. Natl. Acad. Sci. USA 74:5463 (1977); Drmanac et al., Genomics 4:114 (1989); Koster et al., Nature Biotechnology 14:1123 (1996); Hyman, Anal. Biochem. 174:423 (1988); Rosenthal, International Patent Application Publication 761107 (1989); Metzker et al., Nucl. Acids Res. 22:4259 (1994); Jones, Biotechniques 22:938 (1997); Ronaghi et al., Anal. Biochem. 242:84 (1996); Ronaghi et al., Science 281:363 (1998); Nyren et al., Anal. Biochem. 151:504 (1985); Canard and Arzumanov, Gene 11:1 (1994); Dyatkina and Arzumanov, Nucleic Acids Symp Ser 18:117 (1987); Johnson et al., Anal. Biochem. 136:192 (1984); and Elgen and Rigler, Proc. Natl. Acad. Sci. USA 91(13):5740 (1994), all of which are expressly incorporated by reference).

The present invention may be applied to (1) single-cell transcriptomics: cDNA synthesized from mRNA is barcoded and cross-linked during in situ amplification, (2) single-cell proteomics: cDNA or DNA synthesized from RNA- or DNA-tagged antibodies of one or multiple specificities maps the abundance and distributions of different protein-antigens and (3) whole-tissue transcriptomic/proteomic mapping (molecular microscopy or VIPUR microscopy): using the frequency of cross-contamination between cells to determine their physical proximity, and via applications (1) single-cell transcriptomics and (2) single-cell proteomics, determining the global spatial distribution of mRNA, protein, or other biomolecules in a biological sample. This may be used, for example, to screen for anti-cancer/pathogen immunoglobulins (by analyzing co-localization of B-cells and T-cells within affected tissue) for immunotherapy.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein the term "variant" should be taken to mean the exhibition of qualities that differ, such as, but not limited to, genetic variations including SNPs, insertion deletion events, and the like.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogsteen binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences.

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. % homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p 387). Examples of other software than may perform sequence comparisons include, but are not limited to, the BLAST package (see Ausubel et al., 1999 Short Protocols in Molecular Biology, 4th Ed.—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174(2): 247-50; FEMS Microbiol Lett. 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result.

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridyl-alanine, thienylalanine, naphthylalanine and phenylglycine.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Hybridization can be performed under conditions of various stringency. Suitable hybridization conditions for the practice of the present invention are such that the recognition interaction between the probe and sequences associated with a signaling biochemical pathway is both sufficiently specific and sufficiently stable. Conditions that increase the stringency of a hybridization reaction are widely known and published in the art. See, for example, (Sambrook, et al., (1989); Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445,934.

For a convenient detection of the probe-target complexes formed during the hybridization assay, the nucleotide probes are conjugated to a detectable label. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, β-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., 32P, 14C, 125I, 3H, and 131I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinyl sulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcoumarin (Coumaran 151); cyanine dyes; cyanosine; 4',6-diamidino-2-phenylindole (DAPI); 5'5"-dibromopyrogallol-sulfonphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride);

4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalocyanine; and naphthalocyanine The fluorescent label may be a fluorescent protein, such as blue fluorescent protein, cyan fluorescent protein, green fluorescent protein, red fluorescent protein, yellow fluorescent protein or any photoconvertible protein. Colorimetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terylene. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

In an advantageous embodiment, agents may be uniquely labeled in a dynamic manner (see, e.g., international patent application serial no. PCT/US2013/61182 filed Sep. 23, 2012). The unique labels are, at least in part, nucleic acid in nature, and may be generated by sequentially attaching two or more detectable oligonucleotide tags to each other and each unique label may be associated with a separate agent. A detectable oligonucleotide tag may be an oligonucleotide that may be detected by sequencing of its nucleotide sequence and/or by detecting non-nucleic acid detectable moieties to which it may be attached.

The oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the nonnucleic acid detectable moiety.

In some embodiments, a detectable oligonucleotide tag may comprise one or more nonoligonucleotide detectable moieties. Examples of detectable moieties may include, but are not limited to, fluorophores, microparticles including quantum dots (Empodocles, et al., Nature 399:126-130, 1999), gold nanoparticles (Reichert et al., Anal. Chem. 72:6025-6029, 2000), biotin, DNP (dinitrophenyl), fucose, digoxigenin, haptens, and other detectable moieties known to those skilled in the art. In some embodiments, the detectable moieties may be quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag.

In some embodiments, a detectable oligonucleotide tag may comprise one or more non-oligonucleotide detectable moieties. Examples of detectable moieties include, but are not limited to, fluorophores, microparticles including quantum dots (Empodocles, et al., Nature 399:126-130, 1999), gold nanoparticles (Reichert et al., Anal. Chem. 72:6025-6029, 2000), biotin, DNP (dinitrophenyl), fucose, digoxigenin, haptens, and other detectable moieties known to those skilled in the art. In some embodiments, the detectable moieties are quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique nucleotide sequence may be a nucleotide sequence that is different (and thus distinguishable) from the sequence of each detectable oligonucleotide tag in a plurality of detectable oligonucleotide tags. A unique nucleotide sequence may also be a nucleotide sequence that is different (and thus distinguishable) from the sequence of each detectable oligonucleotide tag in a first plurality of detectable oligonucleotide tags but identical to the sequence of at least one detectable oligonucleotide tag in a second plurality of detectable oligonucleotide tags. A unique sequence may differ from other sequences by multiple bases (or base pairs). The multiple bases may be contiguous or non-contiguous. Methods for obtaining nucleotide sequences (e.g., sequencing methods) are described herein and/or are known in the art.

In some embodiments, detectable oligonucleotide tags comprise one or more of a ligation sequence, a priming sequence, a capture sequence, and a unique sequence (optionally referred to herein as an index sequence). A ligation sequence is a sequence complementary to a second nucleotide sequence which allows for ligation of the detectable oligonucleotide tag to another entity which may comprise the second nucleotide sequence, e.g., another detectable oligonucleotide tag or an oligonucleotide adapter. A priming sequence is a sequence complementary to a primer, e.g., an oligonucleotide primer used for an amplification reaction such as but not limited to PCR. A capture sequence is a sequence capable of being bound by a capture entity. A capture entity may be an oligonucleotide which may comprise a nucleotide sequence complementary to a capture sequence, e.g. a second detectable oligonucleotide tag. A capture entity may also be any other entity capable of binding to the capture sequence, e.g. an antibody, hapten or peptide. An index sequence is a sequence which may comprise a unique nucleotide sequence and/or a detectable moiety as described above.

"Complementary" is a term which is used to indicate a sufficient degree of complementarity between two nucleotide sequences such that stable and specific binding occurs between one and preferably more bases (or nucleotides, as the terms are used interchangeably herein) of the two sequences. For example, if a nucleotide in a first nucleotide sequence is capable of hydrogen bonding with a nucleotide in second nucleotide sequence, then the bases are considered to be complementary to each other. Complete (i.e., 100%) complementarity between a first nucleotide sequence and a second nucleotide is preferable, but not required for ligation, priming, or capture sequences.

The present invention also relates to a computer system involved in carrying out the methods of the invention relating to both computations and sequencing.

A computer system (or digital device) may be used to receive, transmit, display and/or store results, analyze the results, and/or produce a report of the results and analysis. A computer system may be understood as a logical apparatus that can read instructions from media (e.g. software) and/or network port (e.g. from the internet), which can optionally be connected to a server having fixed media. A computer system may comprise one or more of a CPU, disk drives, input devices such as keyboard and/or mouse, and a display (e.g. a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web. It is envisioned that data relating to the present invention can be transmitted over such networks or connections (or any other suitable means for transmitting information, including but not limited to mailing a physical report, such as a print-out) for reception and/or for review by a receiver. The receiver can be but is not limited to an individual, or electronic system (e.g. one or more computers, and/or one or more servers).

In some embodiments, the computer system may comprise one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other suitable storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

A client-server, relational database architecture can be used in embodiments of the invention. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments of the invention, the server computer handles all of the database functionality. The client computer can have software that handles all the front-end data management and can also receive data input from users.

A machine readable medium which may comprise computer-executable code may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The subject computer-executable code can be executed on any suitable device which may comprise a processor, including a server, a PC, or a mobile device such as a smartphone or tablet. Any controller or computer optionally includes a monitor, which can be a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard, mouse, or touch-sensitive screen, optionally provide for input from a user. The computer can include appropriate software for receiving user instructions, either in the form of user input into a set of parameter fields, e.g., in a GUI, or in the form of preprogrammed instructions, e.g., preprogrammed for a variety of different specific operations.

The present invention also contemplates multiplex assays. The present invention is especially well suited for multiplex assays. For example, the invention encompasses use of a SureSelectXT, SureSelectXT2 and SureSelectQXT Target Enrichment System for Illumina Multiplexed Sequencing developed by Agilent Technologies, a SeqCap EZ kit developed by Roche NimbleGen, a TruSeq® Enrichment Kit developed by Illumina and other hybridization-based target enrichment methods and kits that add sample-specific sequence tags either before or after the enrichment step, as well as Illumina HiSeq, Mi Seq and NexSeqLife Technology Ion Torrent. Pacific Biosciences PacBio RSII, Oxford Nanopore MinIon, Promethlon and GridIon and other massively parallel Multiplexed Sequencing Platforms.

Usable methods for hybrid selection are described in Melnikov, et al., Genome Biology 12:R73, 2011; Geniez, et al., Symbiosis 58:201-207, 2012; and Matranga, et al., Genome Biology 15:519, 2014). Bait design and hybrid selection was done similarly to a previously published method (see, e.g., Gnirke, et al., Nature biotechnology 27:182-189, 2009, US patent publications No. US 2010/0029498, US 2013/0230857, US 2014/0200163, US 2014/0228223, and US 2015/0126377 and international patent publication No. WO 2009/099602). Briefly, baits may be designed by first concatenating all consensus sequences (such as LASV) into two single bait sets (such as one for Nigerian clades and another for the Sierra Leone clade). Duplicate probes, defined as a DNA sequence with 0 mismatches, were removed. The baits sequences were tiled across the genome (such as LASV) creating a probe every 50 bases. Two sets of adapters were used for each bait set. Adapters alternated with each 50 base probe to improve the efficiency of PCR amplification of probes. The oligo array was synthesized on a CustomArray B3 Synthesizer, as recommended by the manufacturer. The oligonucleotides were cleaved-off the array and amplified by PCR with primers containing T7 RNA polymerase promoters. Biotinylated baits were then prepared through in vitro transcription (MEGAshortscript, Ambion). RNA baits for each clade were prepared separately and mixed at the equal RNA concentration prior to hybridization. Libraries of the genome (such as LASV) were added to the baits and hybridized over a 72 hrs. After capture and washing, libraries were amplified by PCR using the Illumina adapter sequences. Libraries were then pooled and sequenced on the MiSeq platform.

In one aspect of the invention, a method for analyzing a pathogen sequence, such as a bacterial or viral sequence, is provided. The method may comprise sequencing the pathogen sequence according to the method for analyzing a sample which may comprise a target sequence as described above, wherein the target sequence is the pathogen sequence. Preferably the pathogen sequence is a genome of the pathogen or a fragment thereof. The method further may comprise determining the evolution of the pathogen from the sequenced pathogen sequence. Determining the evolution of the pathogen may comprise identification of pathogen mutations in the sequenced pathogen sequence, e.g. nucleotide deletion, nucleotide insertion, nucleotide substitution. Amongst the latter, there are nonsynonymous, synonymous, and noncoding substitutions. Mutations are more frequently nonsynonymous during an outbreak. The method may further comprise determining the substitution rate between two pathogen sequences analyzed as described above. Whether the mutations are deleterious or even adaptive would require functional analysis, however, the rate of nonsynonymous mutations suggests that continued progression of this epidemic could afford an opportunity for viral adaptation, underscoring the need for rapid containment. Thus, the method may further comprise assessing the risk of viral adaptation, wherein the number nonsynonymous mutations is determined. (Gire, et al., Science 345, 1369, 2014).

Because effectiveness of therapeutic response to an outbreak can greatly depend on the knowledge of the pathogen responsible for the outbreak so that proper diagnostics, vaccines and therapies can be conceived, it is of utmost importance that mutations of the pathogen be monitored because mutations alter protein sequences released by the pathogen and which therapeutic response often target. In the case of the 2013-2015 EBOV outbreak, genomic sequencing further allowed the identification of numerous mutations emerging in the EBOV Makona genome over time (Gire, et al., 2014). As a consequence, the evolutionary rate of the Makona variant over the timespan of the early phase of the outbreak could be estimated, and predictions made about the potential of this new EBOV variant to escape current candidate vaccines, therapeutics, and diagnostics (Kugelman, Sanchez-Lockhart, et al., 2015).

For example, during the 2014 EBOV outbreak, Gire et al. reveal 341 fixed substitutions (35 nonsynonymous, 173 synonymous, and 133 noncoding) between the 2014 EBOV and all previously published EBOV sequences, with an additional 55 single-nucleotide polymorphisms (SNPs; 15 nonsynonymous, 25 synonymous, and 15 noncoding), fixed within individual patients, within the West African outbreak. Mutations are also more frequently nonsynonymous during the outbreak. Whether they are deleterious or even adaptive would require functional analysis, however, the rate of nonsynonymous mutations suggests that continued progression of this epidemic could afford an opportunity for viral adaptation, underscoring the need for rapid containment. (Gire, et al., 2014)

In one aspect of the invention, a method for analyzing the evolution of a pathogen outbreak is provided. The method may comprise sequencing a target sequence contained in a plurality of samples from more than one subject according to the method for analyzing a sample which may comprise a target sequence as described above, wherein the target sequence is a pathogen sequence of the pathogen causing the outbreak, and wherein the sequencing the target sequence is done for each of the plurality of samples. The method further may comprise determining a pattern of pathogen transmission, in other words a mechanism involves in a disease outbreak caused by a pathogen.

The pattern of pathogen transmission may comprise continued new transmissions from the natural reservoir of the pathogen or subject-to-subject transmissions (e.g. human-to-human transmission) following a single transmission from the natural reservoir or a mixture of both. In one embodiment, the pathogen transmission is a bacterial or viral transmission, in such case, the target sequence is preferably a bacterial or a viral genomes or fragments thereof. In one embodiment, the pattern of the pathogen transmission is the early pattern of the pathogen transmission, i.e. at the beginning of the pathogen outbreak. Determining the pattern of the pathogen transmission at the beginning of the outbreak enables to increase the success of stopping the outbreak at the very start thereof and as such dimming the specter of local and international dissemination.

Determining the patterns of pathogen transmission, such as viral transmission, notably during the beginning of the outbreak, is a key step towards stopping the epidemic episode at the very start thereof and as such dimming the specter of local and international dissemination. (Gire, et al., 2014)

Determining the pattern of the pathogen transmission may comprise analyzing a pathogen sequence according to the method described above. Determining the pattern of the pathogen transmission may further comprise detecting shared intra-host variations of the pathogen sequence between the subjects and determining whether the shared intra-host variations show temporal patterns. Patterns in observed intrahost and interhost variation provide important insight about transmission and epidemiology (Gire, et al., 2014).

Detection of shared intra-host variations between the subjects that show temporal patterns is an indication of transmission links between subject (in particular between humans) because it can be explained by subject infection from multiple sources (superinfection), sample contamination recurring mutations (with or without balancing selection to reinforce mutations), or co-transmission of slightly divergent viruses that arose by mutation earlier in the transmission chain (Park, et al., Cell 161(7):1516-1526, 2015). Detection of shared intra-host variations between subjects may comprise detection of intra-host variants located at common single nucleotide polymorphism (SNP) positions. Positive detection of intra-host variants located at common (SNP) positions is indicative of superinfection and contamination as primary explanations for the intra-host variants. Superinfection and contamination can be parted on the basis of SNP frequency appearing as inter-host variants (Park, et al., 2015). Otherwise superinfection and contamination can be ruled out. In this latter case, detection of shared intra-host variations between subjects may further comprise assessing the frequencies of synonymous and nonsynonymous variants and comparing the frequency of synonymous and nonsynonymous variants to one another. Equal frequency of synonymous and nonsynonymous variants is indicative of the intra-host variants evolving neutrally. If frequencies of synonymous and nonsynonymous variants are divergent, the intra-host variants are likely to be maintained by balancing selection. If frequencies of synonymous and nonsynonymous variants are low, this is indicative of recurrent mutation. If frequencies of synonymous and nonsynonymous variants are high, this is indicative of co-transmission (Park, et al., 2015).

Like Ebola virus, Lassa virus (LASV) can cause hemorrhagic fever with high case fatality rates. Andersen et al. generated a genomic catalog of almost 200 LASV sequences from clinical and rodent reservoir samples (Andersen, et al., Cell Volume 162, Issue 4, p 738-750, 13 Aug. 2015). Andersen et al. show that whereas the 2013-2015 EVD epidemic is fueled by human-to-human transmissions, LASV infections mainly result from reservoir-to-human infections. Andersen et al. elucidated the spread of LASV across West Africa and show that this migration was accompanied by changes in LASV genome abundance, fatality rates, codon adaptation, and translational efficiency.

The method may further comprise phylogenetically comparing a first pathogen sequence to a second pathogen sequence, and determining whether there is a phylogenic link between the first and second pathogen sequences. The second pathogen sequence may be an earlier reference sequence. If there is a phylogenic link, the method may further comprise rooting the phylogeny of the first pathogen sequence to the second pathogen sequence. Thus, it is possible to construct the lineage of the first pathogen sequence. (Park, et al., 2015)

The method may further comprise determining whether the mutations are deleterious or adaptive. Deleterious mutations are indicative of transmission-impaired viruses and dead-end infections, thus normally only present in an individual subject. Mutations unique to one individual subject are those that occur on the external branches of the phylogenetic tree, whereas internal branch mutations are those present in multiple samples (i.e. in multiple subjects). Higher rate of nonsynonymous substitution is a characteristic of external branches of the phylogenetic tree. (Park, et al., 2015)

In internal branches of the phylogenetic tree, selection has had more opportunity to filter out deleterious mutants. Internal branches, by definition, have produced multiple descendent lineages and are thus less likely to include mutations with fitness costs. Thus, lower rate of nonsynonymous substitution is indicative of internal branches. (Park, et al., 2015)

Synonymous mutations, which likely have less impact on fitness, occurred at more comparable frequencies on internal and external branches. (Park, et al., 2015)

By analyzing the sequenced target sequence, such as viral genomes, it is possible to discover the mechanisms responsible for the severity of the epidemic episode such as during the 2014 Ebola outbreak. For example, Gire et al. made a phylogenetic comparison of the genomes of the 2014 outbreak to all 20 genomes from earlier outbreaks suggests that the 2014 West African virus likely spread from central Africa within the past decade. Rooting the phylogeny using divergence from other ebolavirus genomes was problematic (6, 13). However, rooting the tree on the oldest outbreak revealed a strong correlation between sample date and root-to-tip distance, with a substitution rate of $8 \times 10^{-4}$ per site per year (13). This suggests that the lineages of the three most recent outbreaks all diverged from a common ancestor at roughly the same time, around 2004, which supports the hypothesis that each outbreak represents an independent zoonotic event from the same genetically diverse viral population in its natural reservoir. They also found out that the 2014 EBOV outbreak might be caused by a single transmission from the natural reservoir, followed by human-to-human transmission during the outbreak. Their results also suggested that the epidemic episode in Sierra Leon might stem from the introduction of two genetically distinct viruses from Guinea around the same time. (Gire, et al., 2014)

It has been also possible to determine how the Lassa virus spread out from its origin point, in particular thanks to human-to-human transmission and even retrace the history of this spread 400 years back (Andersen, et al., Cell 162(4): 738-50, 2015).

In relation to the work needed during the 2013-2015 EBOV outbreak and the difficulties encountered by the medical staff at the site of the outbreak, and more generally, the method of the invention makes it possible to carry out sequencing using fewer selected probes such that sequencing can be accelerated, thus shortening the time needed from sample taking to results procurement. Further, kits and systems can be designed to be usable on the field so that diagnostics of a patient can be readily performed without need to send or ship samples to another part of the country or the world.

In any method described above, sequencing the target sequence or fragment thereof may used any of the sequencing processes described above. Further, sequencing the target sequence or fragment thereof may be a near-real-time sequencing. Sequencing the target sequence or fragment thereof may be carried out according to previously described methods (Experimental Procedures: Matranga et al., 2014; and Gire, et al., 2014). Sequencing the target sequence or fragment thereof may comprise parallel sequencing of a plurality of target sequences. Sequencing the target sequence or fragment thereof may comprise Illumina sequencing.

Analyzing the target sequence or fragment thereof that hybridizes to one or more of the selected probes may be an identifying analysis, wherein hybridization of a selected probe to the target sequence or a fragment thereof indicates the presence of the target sequence within the sample.

Currently, primary diagnostics are based on the symptoms a patient has. However, various diseases may share identical symptoms so that diagnostics rely much on statistics. For example, malaria triggers flu-like symptoms: headache, fever, shivering, joint pain, vomiting, hemolytic anemia, jaundice, hemoglobin in the urine, retinal damage, and convulsions. These symptoms are also common for septicemia, gastroenteritis, and viral diseases. Amongst the latter, Ebola hemorrhagic fever has the following symptoms fever, sore throat, muscular pain, headaches, vomiting, diarrhea, rash, decreased function of the liver and kidneys, internal and external hemorrhage.

When a patient is presented to a medical unit, for example in tropical Africa, basic diagnostics will conclude to malaria because statistically, malaria is the most probable disease within that region of Africa. The patient is consequently treated for malaria although the patient might not actually have contracted the disease and the patient ends up not being correctly treated. This lack of correct treatment can be life-threatening especially when the disease the patient contracted presents a rapid evolution. It might be too late before the medical staff realizes that the treatment given to the patient is ineffective and comes to the correct diagnostics and administers the adequate treatment to the patient.

The method of the invention provides a solution to this situation. Indeed, because the number of selected probes can be dramatically reduced, this makes it possible to provide on a single chip selected probes divided into groups, each group being specific to one disease, such that a plurality of diseases, e.g. viral infection, can be diagnosed at the same time. Thanks to the invention, more than 3 diseases can be diagnosed on a single chip, preferably more than 4, 5, 6, 7, 8, 9, 10, 11, 12, 13, 14, 15, 16, 17, 18, 19, 20 diseases at the same time, preferably the diseases that most commonly occur within the population of a given geographical area. Since each group of selected probes is specific to one of the diagnosed diseases, a more accurate diagnostics can be performed, thus diminishing the risk of administrating a wrong treatment to the patient.

In other cases, a disease such as a viral infection may occur without any symptoms, or had caused symptoms but they faded out before the patient is presented to the medical staff. In such cases, either the patient does not seek any medical assistance or the diagnostics is complicated due to the absence of symptoms on the day of the presentation.

The present invention may also be used in concert with other methods of diagnosing disease, identifying pathogens and optimizing treatment based upon detection of nucleic acids, such as mRNA in crude, non-purified samples (see, e.g., US patent publication No. 2013/0190196).

The method of the invention also provides a powerful tool to address this situation. Indeed, since a plurality of groups of selected probes, each group being specific to one of the most common diseases that occur within the population of the given area, are comprised within a single chip, the medical staff only need to contact a biological sample taken from the patient with the chip. Reading the chip reveals the diseases the patient has contracted.

In some cases, the patient is presented to the medical staff for diagnostics of particular symptoms. The method of the invention makes it possible not only to identify which disease causes these symptoms but at the same time determine whether the patient suffers from another disease he was not aware of.

This information might be of utmost importance when searching for the mechanisms of an outbreak. Indeed, groups of patients with identical viruses also show temporal patterns suggesting a subject-to-subject transmission links.

Analyzing the target sequence or a fragment thereof that hybridizes to a selected probe may be carried out by in solution hybrid selection. Each of the selected probes may further comprise an adapter. Each of the selected probes may comprise two adapters. In this latter case, a first adapter may be alternated with a second adapter. In all described case, two of the selected probes may overlap.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

For Example 1, a collection of 140 publically available genomes (double stranded) of Ebola Zaire virus (EBOV) with an approximate genome length of 19,000 bp was used as the reference sequence. Selection of probes was carried out using the method with the dominating set solving process or the set cover solving process. So far, Applicants have experimented with probes of length 100 bp.

In one embodiment, a parameter may be a cover_length. This is a parameter used alongside the mismatches parameter. In the set cover context, a probe covers a portion of a target sequence (i.e., that portion is included in the probe's hybridization pattern) if it shares a substring with less than or equal to the specified number of mismatches and whose length is greater than or equal to cover_length. In the dominating set context, two probes are redundant if they share a substring with less than or equal to the specified number of mismatches and whose length is greater than or equal to cover_length.

This cover_length parameter does make a big difference with the dominating set problem (i.e., determining whether two probes are redundant). But it turns out not to make as much of a difference with the set cover approach which is why the parameter is fixed at the length of the probe (100 bp) and not varied. When the figures mention 85 bp, 95 bp, and 100 bp that is in reference to the value of the cover_length, not the length of the probe.

Candidate probes were constructed by fragmenting each of the genomes into fragments of desired length (100 bp was used, however other lengths, such as 85 bp, 95 bp, may also be used as well as fragments of about 15 to about 150 bp or fragments of about 70 bp to about 130 bp are also contemplated), the fragments overlapping one another so that the overlap between two fragments was half the length of the fragments (2× tiling). Each candidate probe is one of these fragments. The candidate probes collectively have a hybridization pattern along all genomes.

The number of candidate probes was then reduced according to different processes as described hereafter and to different value of acceptable number of mismatches (0, 1, 2, 3, 4, and 5).

Example 1.1: Dominating Set Solving Process

The redundancy between candidate probes was assessed by comparing each probe to the others. Two candidate probes were considered redundant if one of them presents a portion of a given length that was the same as the portion of a given length of the other probe, wherein the portions were considered the same even if there were up to a considered value of acceptable number of mismatches.

The candidate probes were subjected to a dominating set solving process to reduce the number of candidate probes to provide a set of selected probes.

Example 1.2: Set Cover Solving Process

For each candidate probe, its individual hybridization pattern was determined. The candidate probes were aligned back to the target sequences in a manner similar to how many short-read aligners work. In short, it seeds an alignment (by quickly finding an exact match between a short part of a probe and the target sequence), and then verifies whether this is a true alignment by expanding outward. It is a true alignment if the candidate probe and the portion of the target sequence share a substring of length at least cover length with at most a specified number of mismatches. When cover length is fixed at the length of a probe, 100 bp, this means that the candidate probe and the portion of the target sequence are the same up to the specified number of mismatches. "Short read alignment: seeding" is an introduction to short read alignment with seeding, and is similar to the herein described approach, although spaces/gaps were not allowed. The individual hybridization patterns were subjected to a greedy method for solving a set cover problem. Alternate embodiments might use other methods to solve set cover problem. Other methods include, but are not limited to, framing a set cover problem as an 'integer linear program' ('ILP') and solving via 'LP relaxation'.

In the set cover problem, the genomes collectively form a universe of elements that are the nucleotides (positions within the genomes being considered as differentiating nucleotides of the same type). The individual hybridization patterns were taken as subsets of the universe.

Comparative Example 1

The same collection of 140 genomes of Ebola Zaire virus was used as the reference sequence. Candidate probes of the same length were constructed therefrom.

The number of candidate probes was then reduced according to prior art process: the candidate probes were arbitrarily ordered to build a list. Any probe that is redundant to the first candidate probe is removed from the list. Then, any probe that is redundant to the next remaining candidate probe is removed from the list. This is repeated until the bottom of the list is reached.

Results

The following tables show the number of selected probes generated as output of Example 1.1, Example 1.2 and Comparative example 1 (FIGS. 6 to 11 graphically illustrate the results):

TABLE 1 number of selected probes for candidate probe length of 85 bp

| | Number of mismatches | | | | | |
|---|---|---|---|---|---|---|
| | 0 | 1 | 2 | 3 | 4 | 5 |
| Example 1.1 | 4316 | 2658 | 2014 | 1714 | 1630 | 1560 |
| Example 1.2 | 2268 | 1282 | 828 | 612 | 524 | 480 |
| Comparative example 1 | 5664 | 4180 | 3346 | 2680 | 2592 | 2440 |

TABLE 2 number of selected probes for candidate probe length of 95 bp

| | Number of mismatches | | | | | |
|---|---|---|---|---|---|---|
| | 0 | 1 | 2 | 3 | 4 | 5 |
| Example 1.1 | 8486 | 6442 | 5526 | 4998 | 4788 | 4634 |
| Example 1.2 | 2384 | 1358 | 910 | 664 | 564 | 508 |
| Comparative example 1 | 8730 | 7050 | 6046 | 5414 | 5060 | 4818 |

TABLE 3 number of selected probes for candidate probe length of 100 bp

| | Number of mismatches | | | | | |
|---|---|---|---|---|---|---|
| | 0 | 1 | 2 | 3 | 4 | 5 |
| Example 1.1 | 27612 | 25446 | 24482 | 23934 | 23686 | 23516 |
| Example 1.2 | 2506 | 1442 | 980 | 752 | 650 | 582 |
| Comparative example 1 | 27612 | 25762 | 24786 | 24162 | 23826 | 23606 |

The following tables show the percentage of reduction with regard to the prior art Comparative Example 1

TABLE 4 reduction percentage for candidate probe length of 85 bp

| | Number of mismatches | | | | | |
|---|---|---|---|---|---|---|
| | 0 | 1 | 2 | 3 | 4 | 5 |
| Example 1.1 | 76.2 | 63.6 | 60.2 | 64.0 | 62.9 | 63.9 |
| Example 1.2 | 40.0 | 30.7 | 24.7 | 22.8 | 20.2 | 19.7 |

TABLE 5 reduction percentage for candidate probe length of 95 bp

| | Number of mismatches | | | | | |
|---|---|---|---|---|---|---|
| | 0 | 1 | 2 | 3 | 4 | 5 |
| Example 1.1 | 97.2 | 91.4 | 91.4 | 92.3 | 94.6 | 96.2 |
| Example 1.2 | 27.3 | 19.3 | 15.1 | 12.3 | 11.1 | 10.5 |

TABLE 6 reduction percentage for candidate probe length of 100 bp

| | Number of mismatches | | | | | |
|---|---|---|---|---|---|---|
| | 0 | 1 | 2 | 3 | 4 | 5 |
| Example 1.1 | 100.0 | 98.8 | 98.8 | 99.1 | 99.4 | 99.6 |
| Example 1.2 | 9.1 | 5.6 | 4.0 | 3.1 | 2.7 | 2.5 |

Example 2

For Example 2, a collection of different number of genomes (double stranded) of Ebola Zaire virus (EBOV) with an approximate genome length of 19,000 bp was used as the reference sequence. Selection of probes was carried out using the method with the dominating set solving process or the set cover solving process. The candidate probe length was 100 bp and 0 mismatches were allowed.

Other details of Example 2 are the same as Example 1. Example 2.1 used the dominating set solving problem whereas Example 2.2 used the set cover solving process.

Comparative Example 2

For Example 2, a collection of different number of genomes (double stranded) of Ebola Zaire virus (EBOV) with an approximate genome length of 19,000 bp was used as the reference sequence. Selection of probes was carried out using the method with the dominating set solving process or the set cover solving process. The cover_length parameter was 100 bp (however other lengths, such as 85 bp, 95 bp, may also be used as well as fragments of about 15 to about 150 bp or fragments of about 70 bp to about 130 bp are also contemplated) and 0 mismatches were allowed. Full coverage was considered for the construction of candidate probes.

Other details o Example 1 are the same as Example 1.
Results

Figures 12, 13:
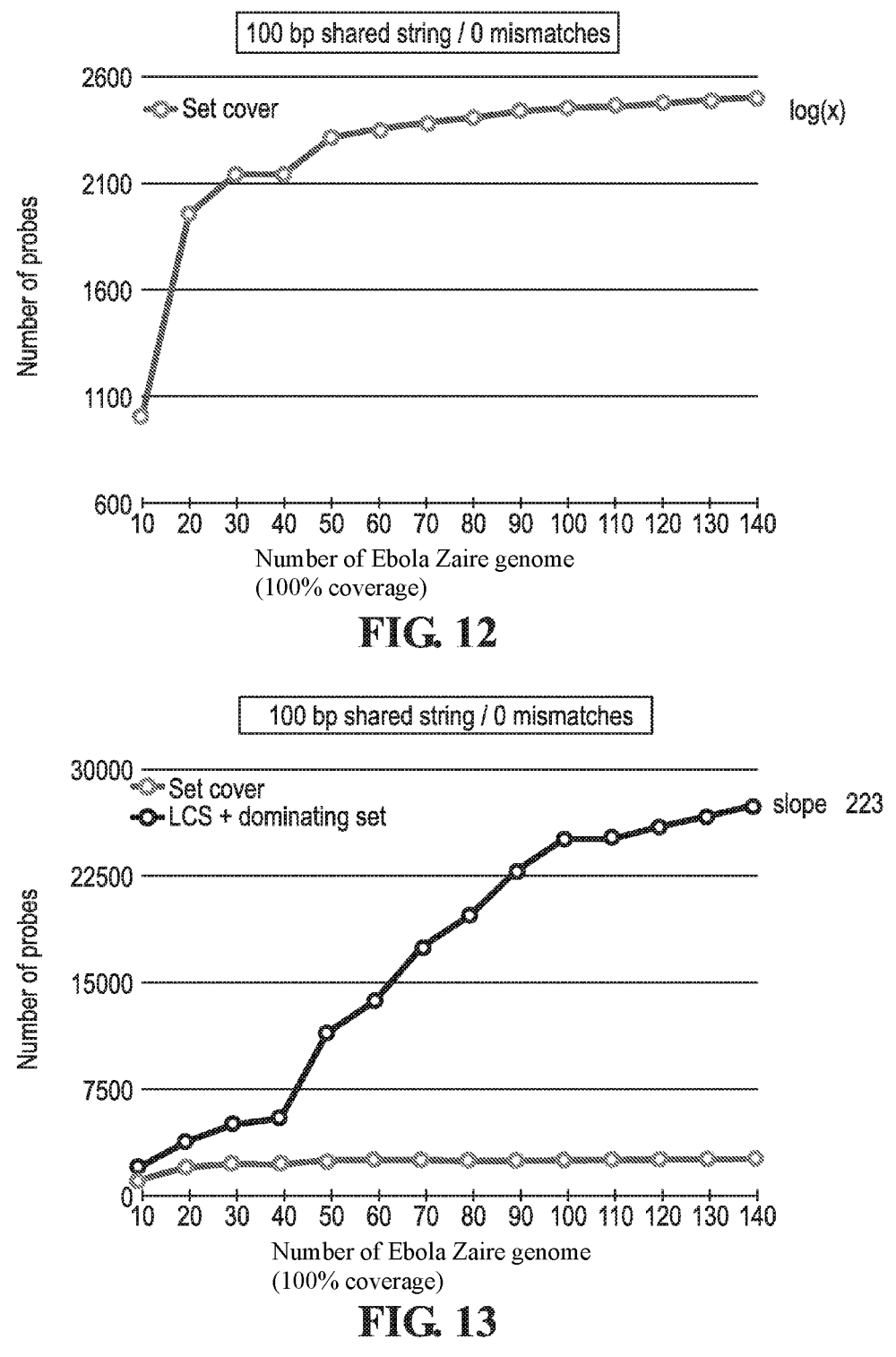

The following tables show the number of selected probes generated as output of Example 2.1, Example 2.2 (FIGS. 12 and 13 graphically illustrate the results):

TABLE 6

| | Number of probes | | |
|---|---|---|---|
| | | Example 2.1 | Example 2.2 |
| Number of Ebola Zaire genomes as reference | 10 | 1922 | 1002 |
| | 20 | 3784 | 1964 |
| | 30 | 4994 | 2146 |
| | 40 | 5358 | 2152 |
| | 50 | 11432 | 2326 |
| | 60 | 13746 | 2356 |
| | 70 | 17506 | 2386 |
| | 80 | 19832 | 2412 |
| | 90 | 22902 | 2446 |
| | 100 | 25156 | 2462 |
| | 110 | 25258 | 2468 |
| | 120 | 26052 | 2484 |
| | 130 | 26838 | 2496 |
| | 140 | 27612 | 2506 |

Like previous approaches, the number of probes using dominating set solving process linearly increases with the number of Ebola Zaire genomes (with a slope of about 223), however, the number of probes using set cover solving process logarithmically increases with the number of Ebola Zaire genomes.

Example 3

Figure 14:
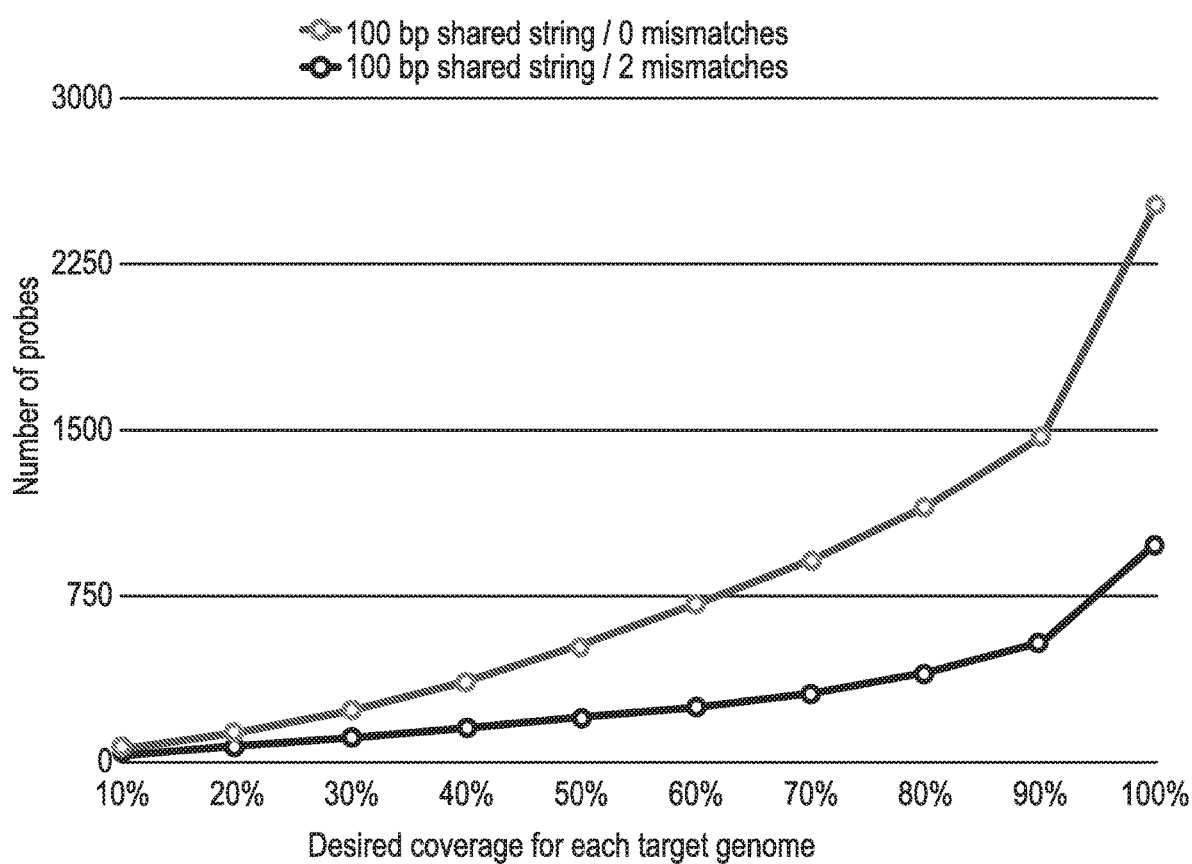
FIG. 14 graphically shows the number of selected probes generated as output of Example 3 with 0 allowed mismatches or 2 allowed mismatches.

For Example 3, a collection of 140 genomes (double stranded) of Ebola Zaire virus (EBOV) with an approximate genome length of 19,000 bp was used as the reference sequence. Candidate probe length was 100 bp. And values of acceptable number of mismatches of 0 and 2 were assessed. Selection of probes was carried out using the partial set cover solving process. Other details of Example 3 are the same as Example 1.2.
Results The following tables show the number of selected probes generated as output of Example 3 with 0 allowed mismatches or 2 allowed mismatches (FIG. 14 graphically illustrates the results):

TABLE 7

| | Number of probes | | |
|---|---|---|---|
| | | Number of allowed mismatches | |
| | | 0 | 2 |
| Percentage of desired coverage of the target sequence | 10% | 56 | 38 |
| | 20% | 126 | 76 |
| | 30% | 228 | 114 |
| | 40% | 358 | 152 |
| | 50% | 518 | 190 |
| | 60% | 704 | 246 |
| | 70% | 910 | 304 |
| | 80% | 1144 | 402 |
| | 90% | 1466 | 538 |
| | 100% | 2506 | 980 |

Example 4

For Example 4, a collection of publically available genomes (double stranded) of 20 different virus types was used as the reference sequence. For each virus type, a different number of genomes were used depending on availability (previously sequenced genomes). Candidate probe length was 100 bp and up to 3 mismatches were allowed.

Selection of probes was carried out using the method with the set cover solving process (full coverage of the reference sequence). A list of viruses that were put into the pan-viral probe set is presented below.

| Virus | Mismatches allowed | Extension allowed | Number probes |
|---|---|---|---|
| Chikungunya | 2 | 0 | 1882 |
| Crimean-Congo | 2 | 30 | 6228 |
| Dengue | 3 | 20 | 4280 |
| Ebola non-Zaire | 1 | 30 | 4918 |
| Ebola Zaire (incl. 2014) | 1 | 10 | 1284 |
| GB virus C | 1 | 0 | 2996 |
| Hepatitis A | 2 | 0 | 2172 |
| Hepatitis C | 5 | 50 | 13120 |
| HIV-1 (w/o LTR) | 6 | 40 | 15428 |
| HIV-2 (w/o LTR) | 1 | 30 | 3314 |
| Influenza A and B | 3 | 30 | 9084 |
| Lassa | 4 | 30 | 6170 |
| Marburg | 2 | 0 | 2422 |
| Measles | 2 | 0 | 1340 |
| MERS | 1 | 0 | 2716 |

-continued

| Virus | Mismatches allowed | Extension allowed | Number probes |
|---|---|---|---|
| Rhabdovirus | 3 | 50 | 7138 |
| Rift valley fever | 2 | 0 | 1528 |
| SARS | 1 | 10 | 1022 |
| Yellow fever | 2 | 0 | 2948 |
| TOTAL | | | 89990 |

That table also includes the optimized parameters (chosen by minimizing a loss function) and the number of selected probes for each virus.

Other details are the same as for Example 1.2.

Results

The following table sums up the results that were obtained.

TABLE 8

Number of selected probes for each of virus type

| Virus type | Approximate genome length (bp) | Number of genomes used as reference sequence | Number of selected probes |
|---|---|---|---|
| Ebola Zaire | 19,000 | 239 | 748 |
| Measles | 16,000 | 53 | 942 |
| SARS | 30,000 | 143 | 984 |
| Chikungunya | 12,000 | 213 | 1,404 |
| Hepatitis A | 7,500 | 34 | 1,632 |
| Marburg | 19,000 | 78 | 2,010 |
| Yellow fever | 11,000 | 55 | 2,454 |
| MERS | 30,000 | 204 | 2,764 |
| Ebola non-Zaire | 19,000 | 53 | 4,740 |
| Dengue | 10,500 | 302 | 5,376 |
| Lassa | 10,500 | 222 | 13,642 |
| Influenza A + B | 13,500 | 1,125 | 13,658 |
| Rhabdovirus | 12,000 | 243 | 15,558 |
| HIV 1 + 2 | 8,000-11,000 | 1,779 | 116,364 |

Thus, if HIV 1+2 virus type is set aside, the total number of selected probes is 65,912, which is lower than the number of spots usually available on commercialized chips (for example about 90,000 spots available on a CustomArray B3 Synthesizer). Thus, this makes it possible to design a portable chip for virus identification at the site of sample taking as a help with diagnosing the virus type or types the patient has contracted. See also the table below for a pan-viral probe set where the parameters are varied across viruses (instead of keeping 3 mismatches for all), which includes HIV 1+2, as well as Hepatitis-C (another very diverse virus), and uses just under 90,000 probes.

Figure 15:
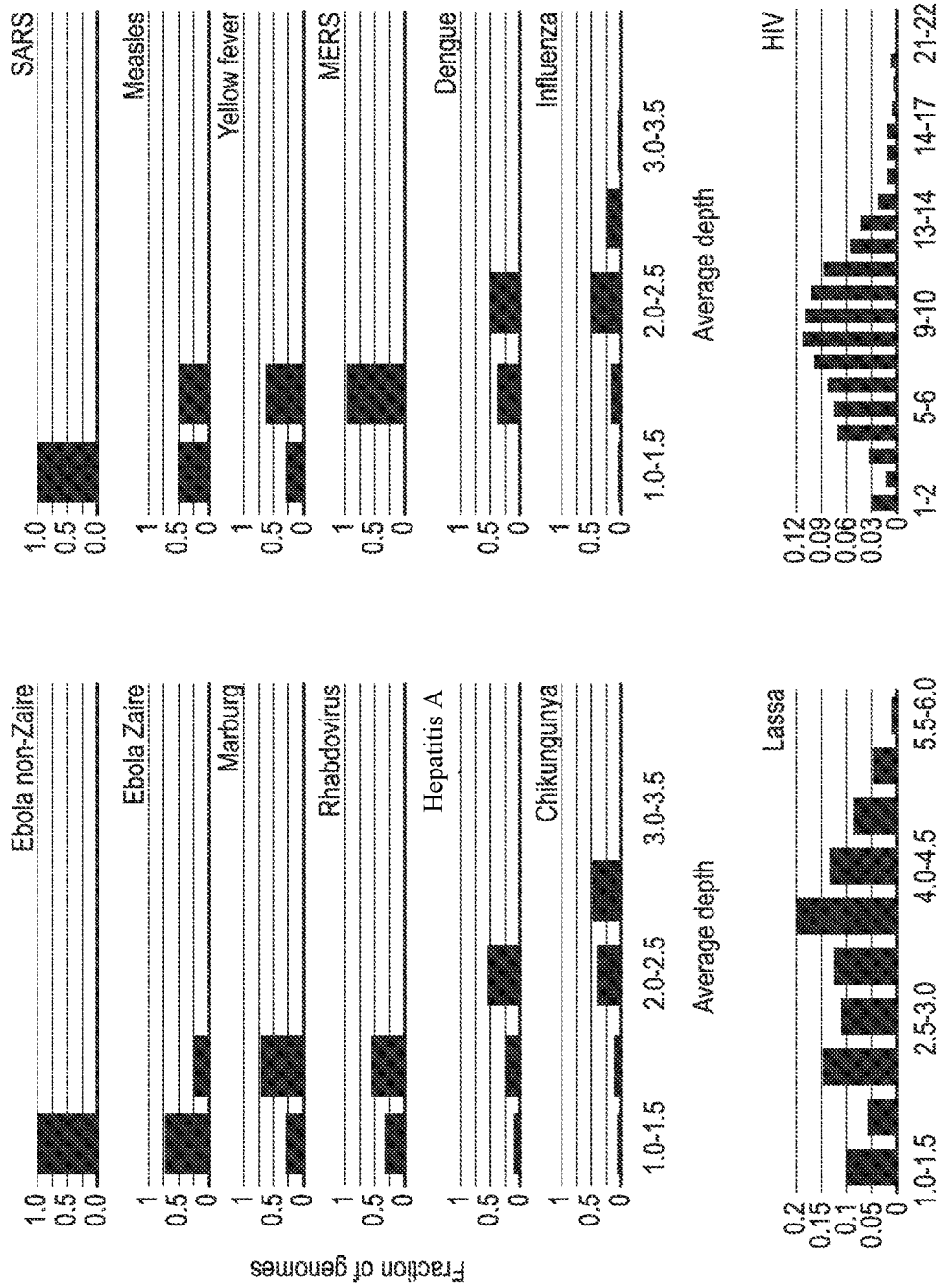
FIG. 15 shows the average depth obtained by the selected probes for each of the virus types.
Figure 16:
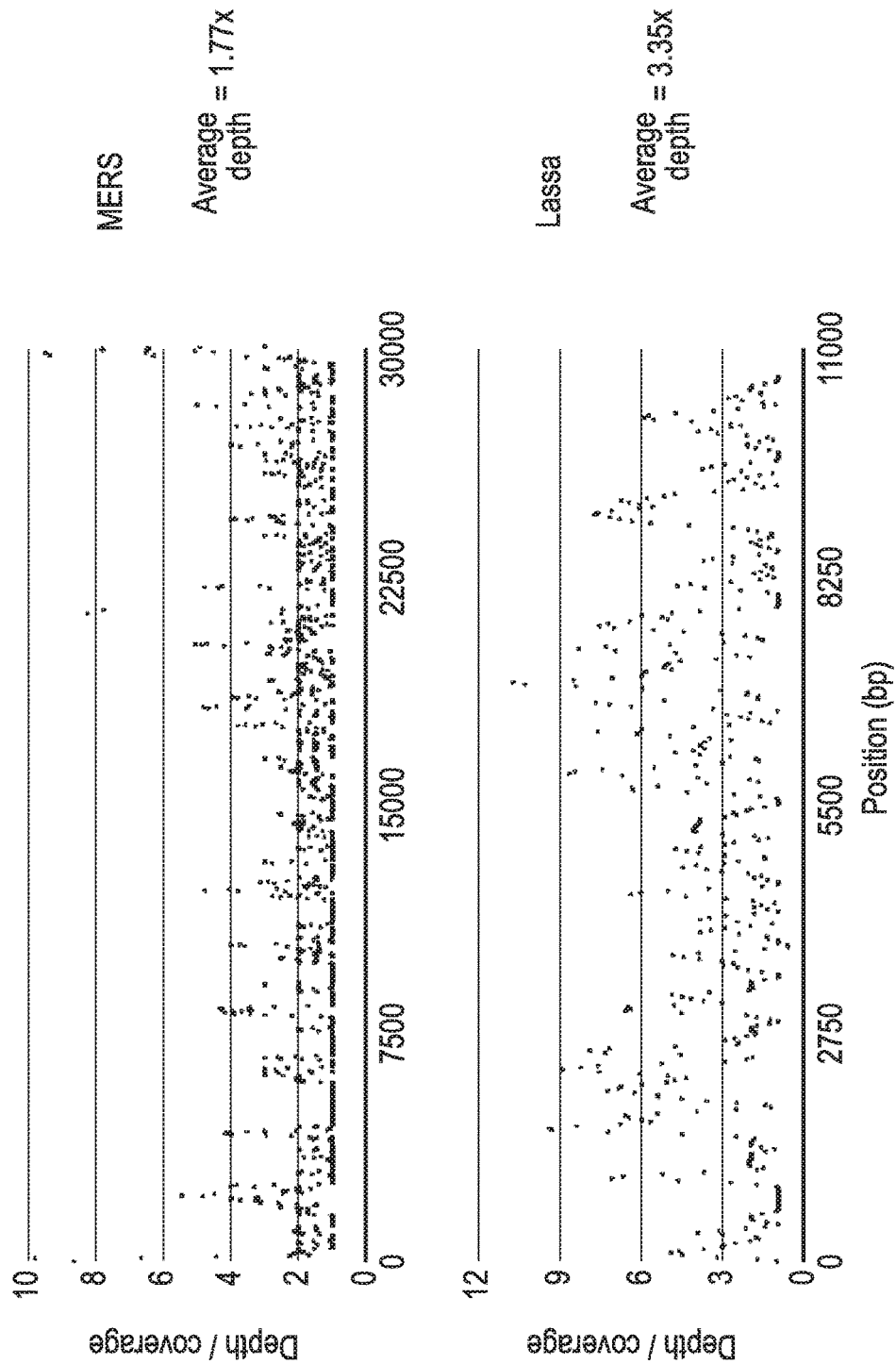
FIG. 16 shows the depth within genomes of two virus types: MERS and Lassa viruses.
Figure 17:
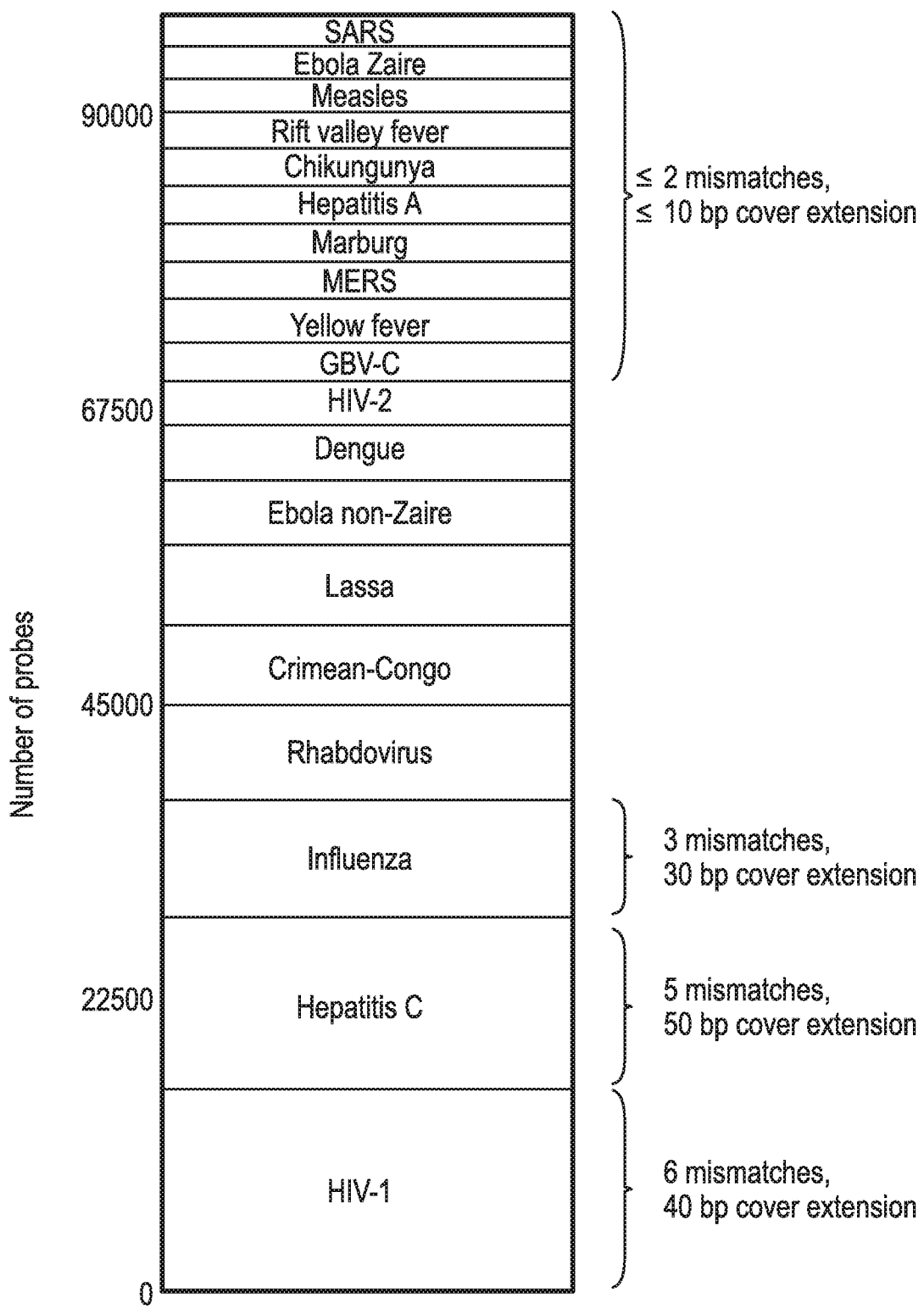
FIG. 17 shows the number of probes in a pan-viral probe set as well as set cover parameters used when generating probes for different viruses, in accordance with certain example embodiments.

As the results of Example 4 show, if only partial coverage is required, the number of selected probes can be further reduced so that the total number of selected probes for all 20 virus types can be reduced below 90,000. This is possible, with weighted partial set cover solving process and by selecting candidate probes that hit only one of the virus types. The natural application of weighted partial set cover is designing probes for identification among the viruses (namely, a very small number of probes). There was identification (targeting 1,000 bp of each target genome) with 3,542 probes for all of the viruses listed below:

FIG. 15 shows the average depth obtained by the selected probes for each of the virus types. FIG. 16 shows the depth within genomes of two virus types: MERS and Lassa viruses. FIG. 17 provides a graphic representation of the number of probes selected for each virus using the set cover solving process as described herein. The cover extension and mismatch parameters used for various viruses are also shown. As indicated in FIG. 17 the more diverse viruses, like HIV-1, included more probes.

FIGS. 18-21 show the results of 4 clinical isolates tested using the above pan-viral probe set. For each, the top bar chart shows the fraction of sequenced reads belonging to the virus, with a higher number of reads indicating a higher level of enrichment. The bottom left chart shows the fraction of the virus' genome from which a de novo assembly could be derived. The bottom-right chart shows the median cover over the de novo assembled genome.

Figure 18:
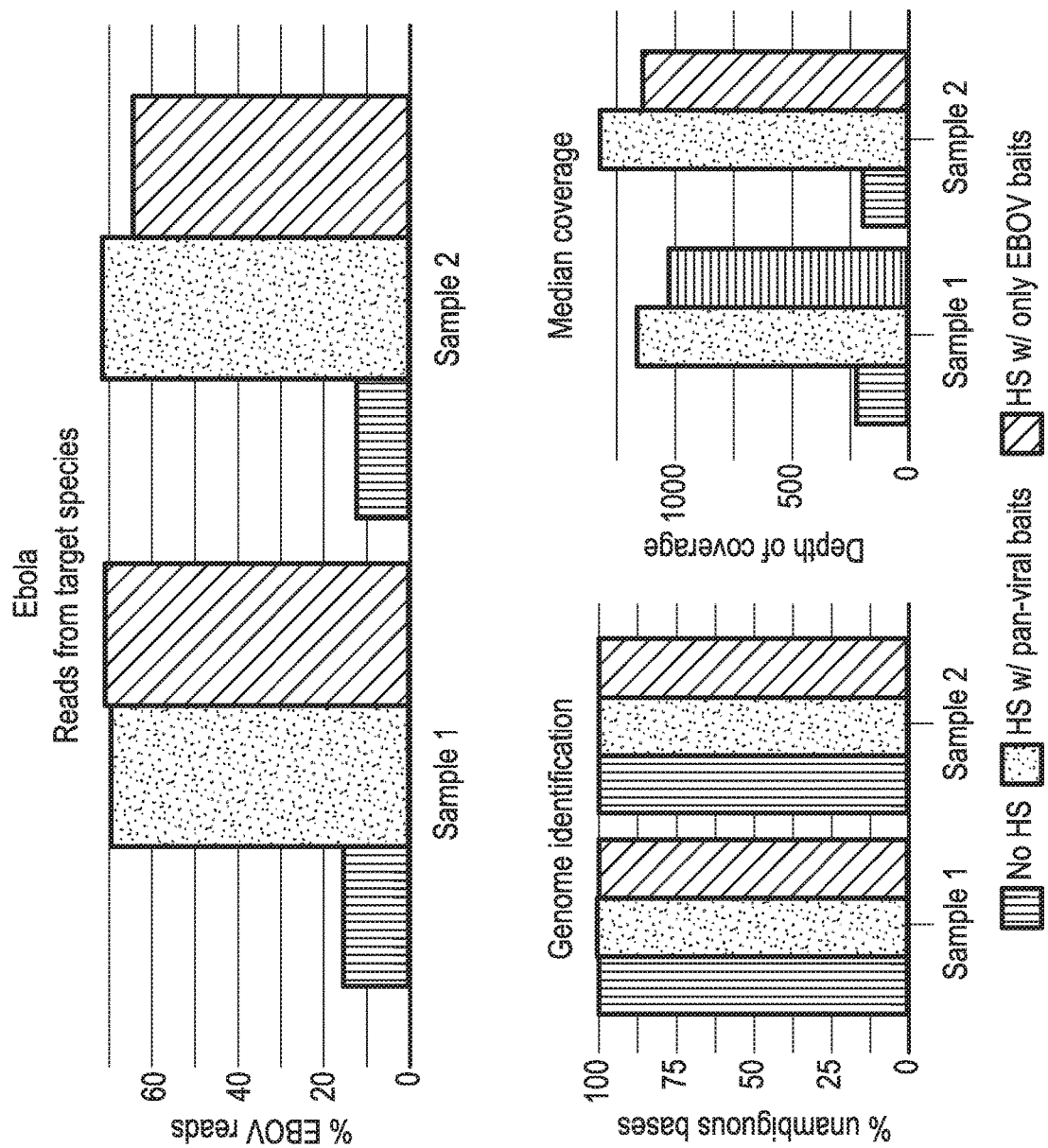
FIGS. 18-21 show the results of using the pan-viral probe to screen four different viruses, in accordance with certain example embodiments. For each figure the top bar chart shows the fraction of sequenced reads belong to the virus (higher reads indicates more enrichment of the virus). The bottom-left bar chart shows the fraction of the virus' genome that was de novo assembled from the sequencing reads obtained from the assay. "No HS" indicates no hybrid selection. "HS w/pan-viral baits" indicates hybrid selection and use of probes designed in accordance with certain example embodiments. "HS w/only EBOV baits" indicates hybrid selection using a naïve tiling approach and that contains a lot of redundant probes.
Figure 19:
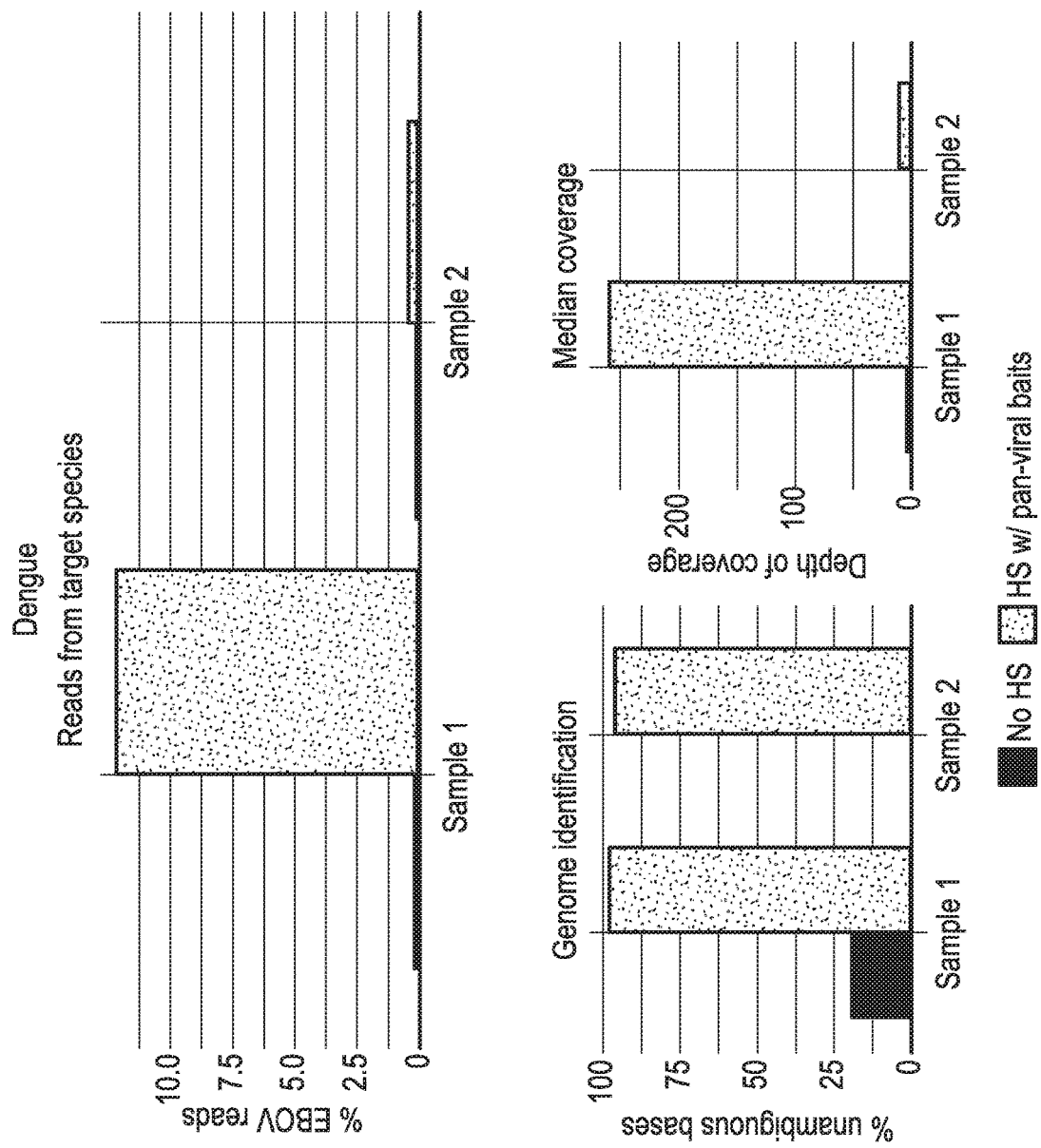
Figure 20:
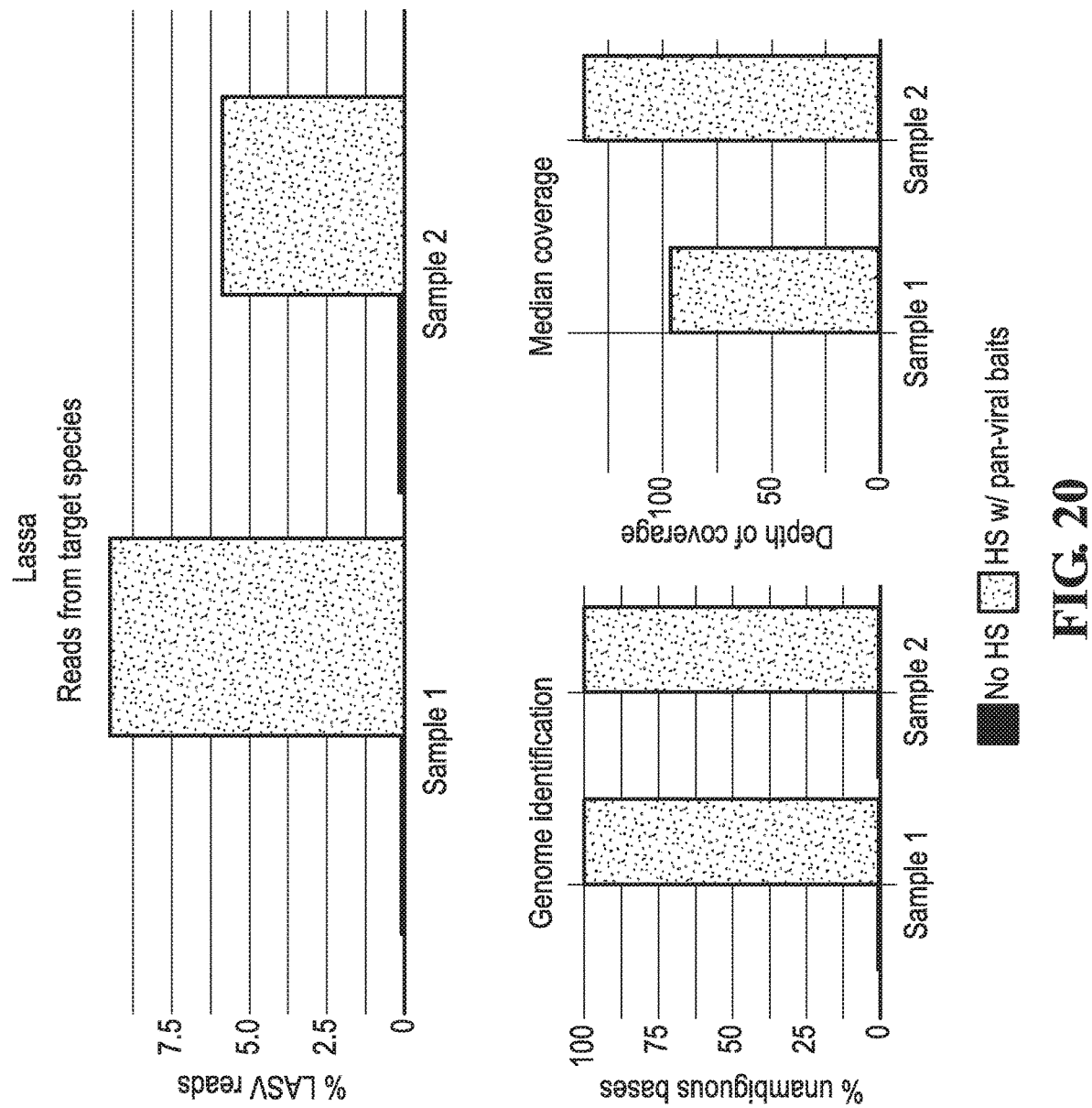
Figure 21:
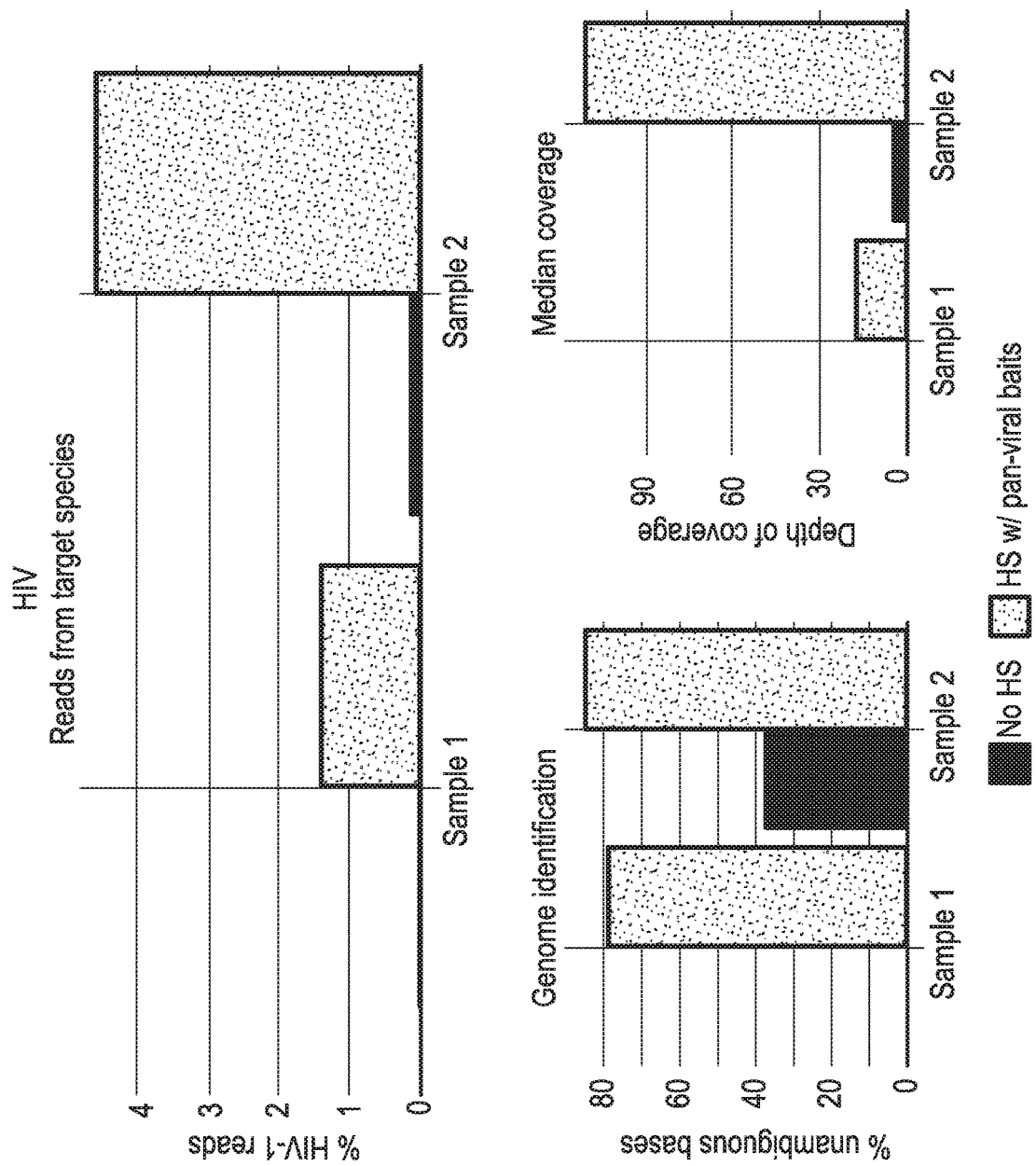

For Ebola Zaire in FIG. 18, results were obtained without hybrid selection ("No HS"), with hybrid selection and pan-viral probe set disclosed above ("HS w/pan-viral baits") and hybrid selection with Ebola Zaire specific probes designed using a naïve tiling approach ("HS w/only EBOV baits"). As shown in FIG. 18, the pan-viral probe set (1,284 probes) is as sensitive in enrichment as the probe set specifically designed only for Ebola Zaire. Further, the pan-viral probe set achieved this level of sensitivity by including only 1,284 probes to Ebola Zaire, whereas the Ebola Zaire specific probe set derived using the naïve tiling method required 27,654 probes.

Clear enrichment can also be seen in Dengue, Lassa, and HIV (FIGS. 19-21, respectively), where use of the pan-viral probe set was able to rescue sample and sequence genomes that could not be sequenced without hybrid selection.

Figure 22:
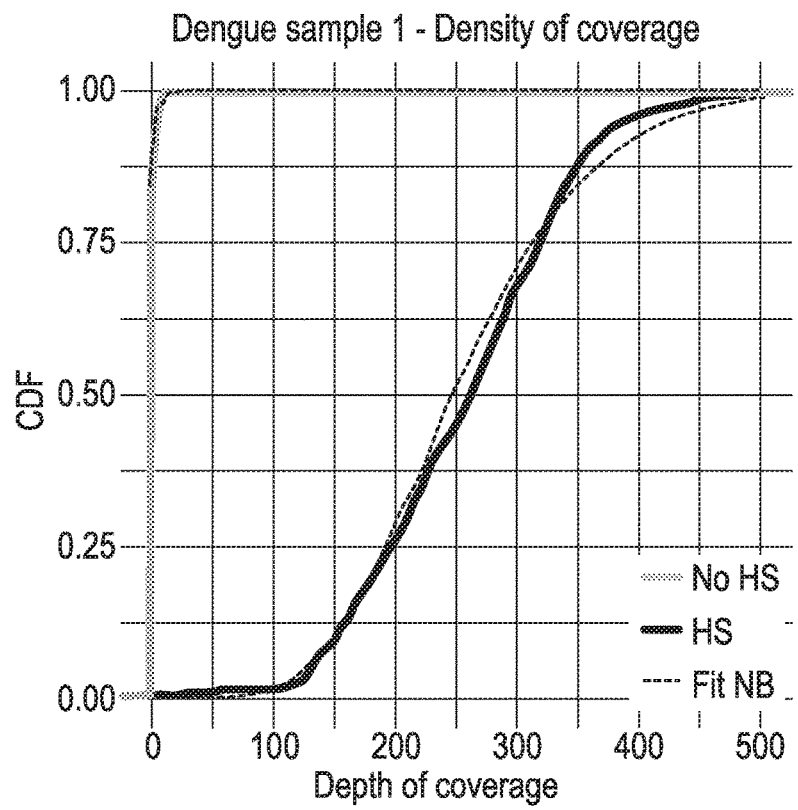
FIGS. 22 and 23 shows cumulative distribution functions (CDF) of coverage across the assembled genome for one of the Dengue samples and one of the Ebola samples. Red line is without hybrid selection, blue line is with hybrid selection and black line is a best-fit negative binomial to the CDFs.
Figure 23:
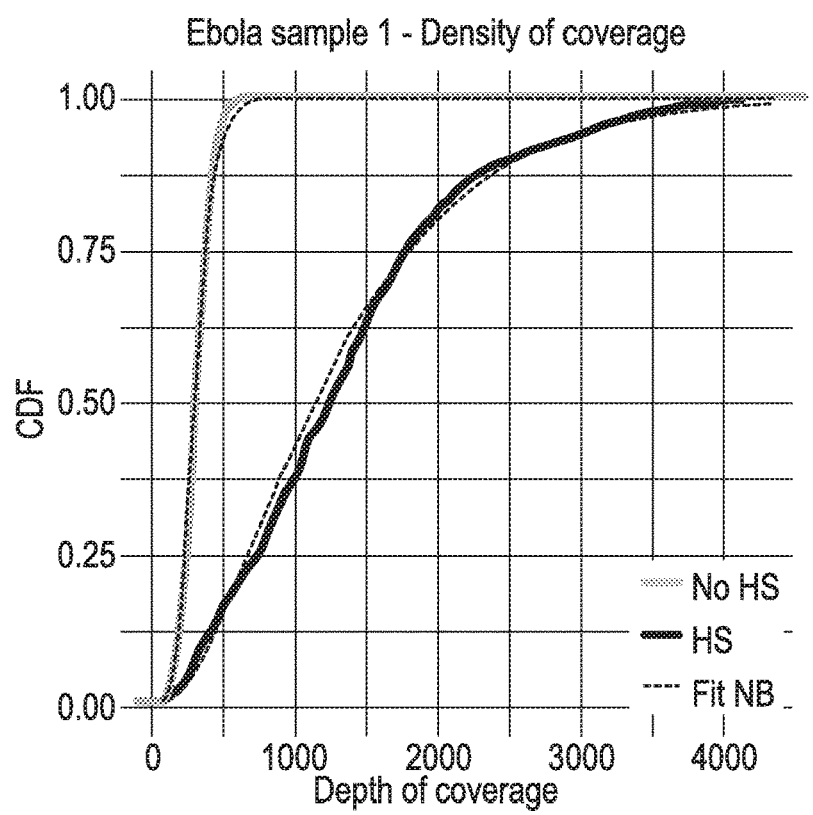

FIGS. 22 and 23 show cumulative distribution functions of coverage across the assembled genome for one of the Dengue samples and one of the Ebola samples. Since coverage is 0 in the samples without hybrid selection, the red lines hug the y-axis most of the way up. A negative binomial is often used to model read coverage in a genome. The comparison of the blue lines with the black ones shows that the hybrid selection does not introduce huge spikes in coverage in certain regions of the genome.

Figure 24:
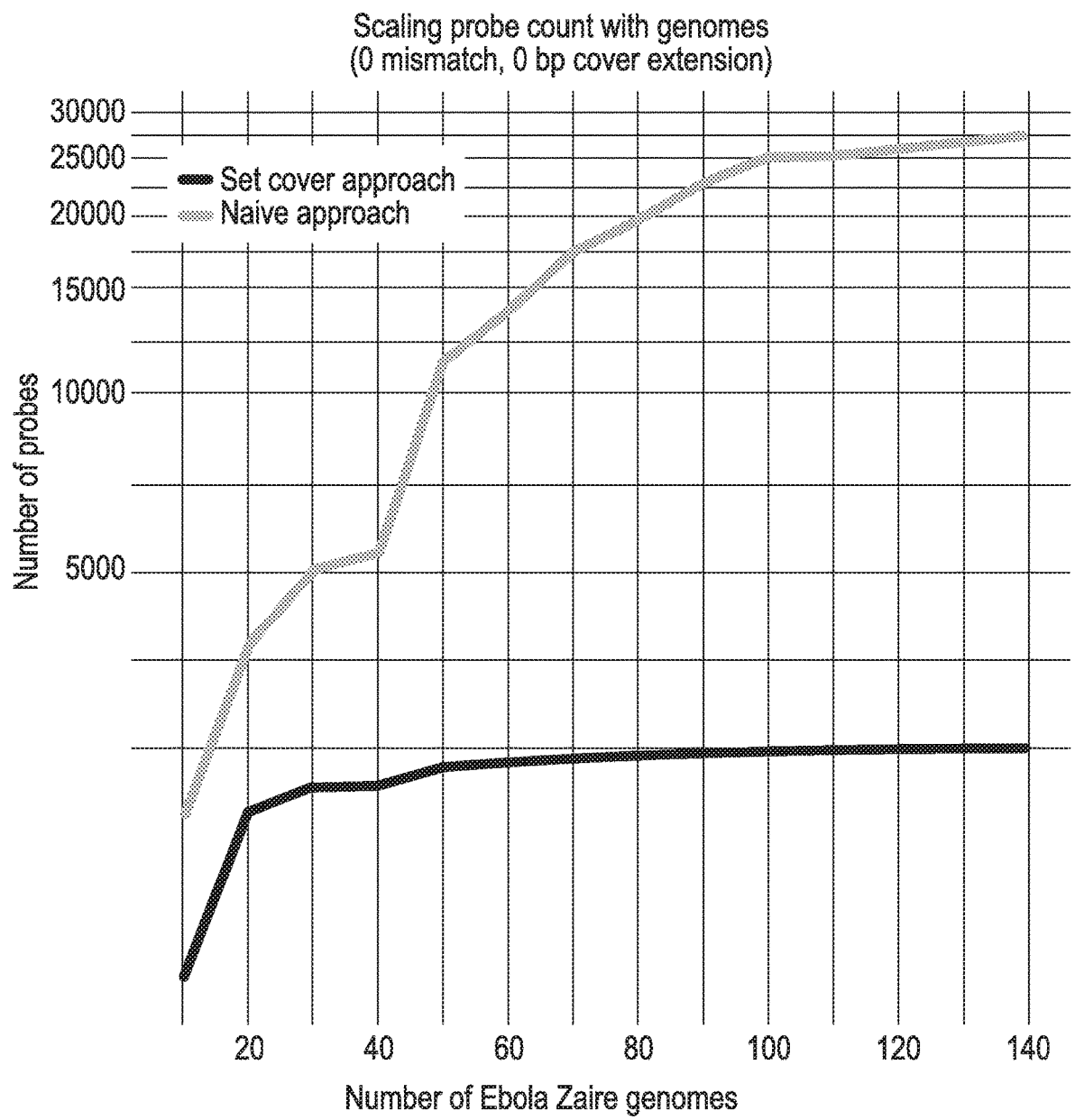
FIG. 24 shows the number of probes necessary to target Ebola Zaire genomes in a semi-naïve approach (Naïve approach) and using the method of the invention (Set cover approach) as a function of the number of Ebola Zaire genomes that are targeted.

FIG. 24 shows that the number of probes required by the method of the invention to target Ebola Zaire genomes is much lower versus the number of probes required using a semi-naïve approach as the number of targeted genomes increases in comparison. The ratio is about 11 fold more probes with the semi-naïve approach than with the methods disclosed herein.

Figure 25:
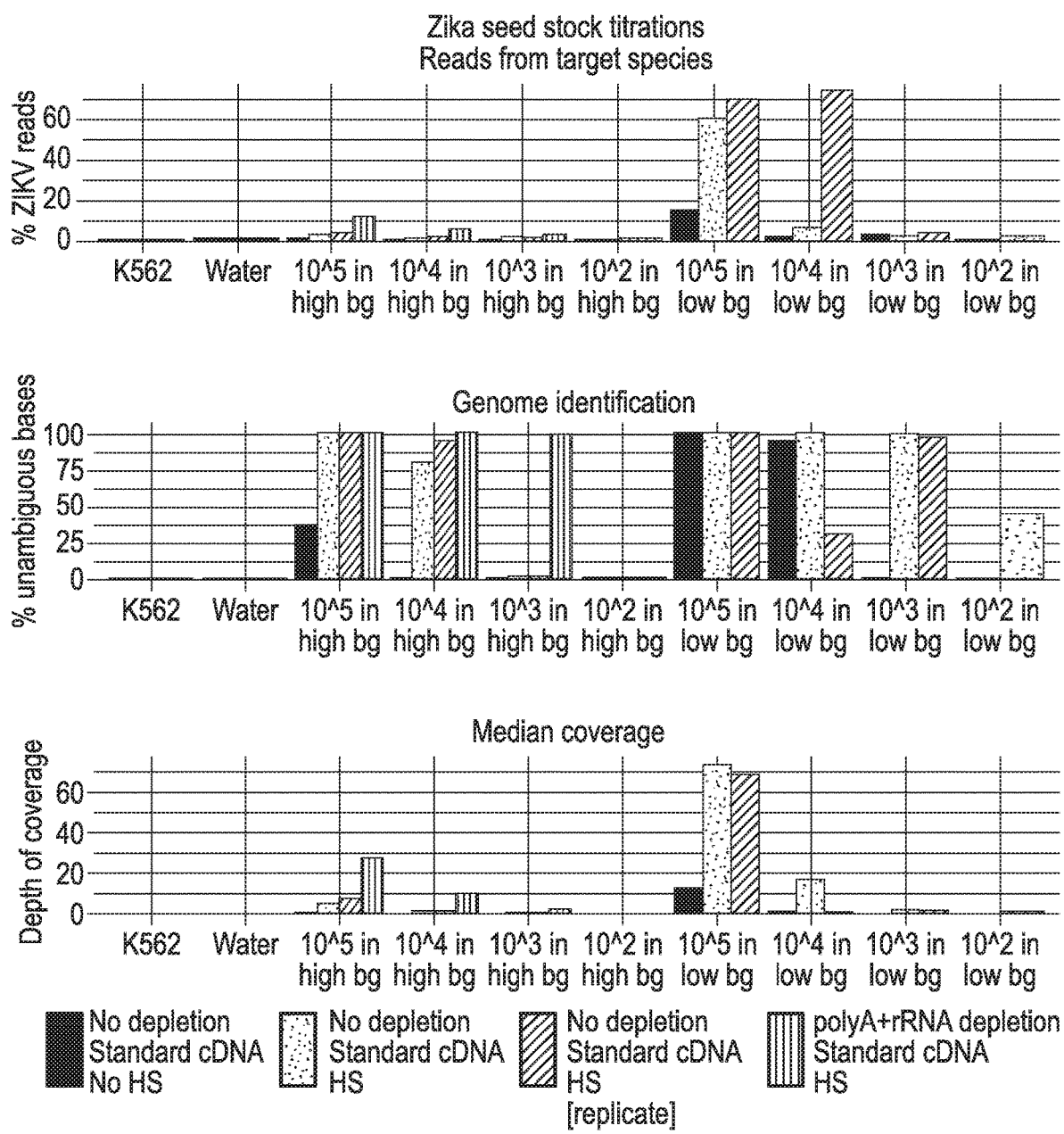
FIG. 25 shows results for further testing on Zika virus. The top bar plot shows the fraction of reads that are Zika. The middle one shows the fraction of the Zika genome which could be de novo assembled. The bottom shows the median coverage over the assembled genome. The x-axis labels are the number of copies of Zika per and "low/high bg" means a low/high amount of background material.

Mock libraries were generated from Zika seedstock to test sequencing methods. Probes were generated to the reference Zika genomes as described above. Referring to FIG. 25, the top bar plot shows the fraction of reads that are Zika. The middle bar graph show the fraction of the Zika genome that could be de novo assembled. The bottom bar graph shows the median coverage over the assembled genome. The x-axis labels are the copies of Zika per μL, and "low/high bg" means a low/high amount of background material. As shown by this figure, hybrid selection is necessary for sequencing samples in high background at all concentrations, and in low background at 103 cp/μL of Zika and below.

Figure 26:
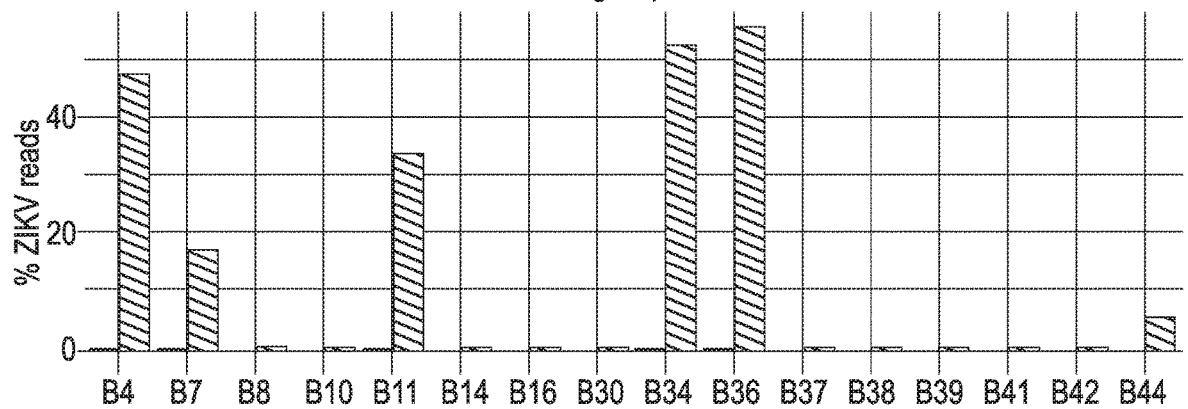
FIG. 26 shows the same type of information as FIG. 25 but using a reference-based process rather than de novo assembly. The shown results are assembly results on clinical Zika samples from a Zika infested area in South America.
Figure 26:
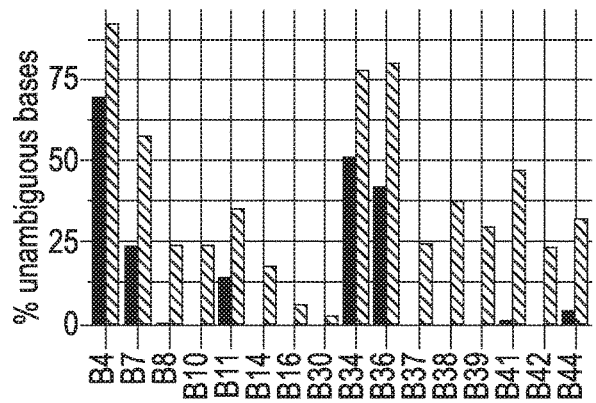
Figure 26:
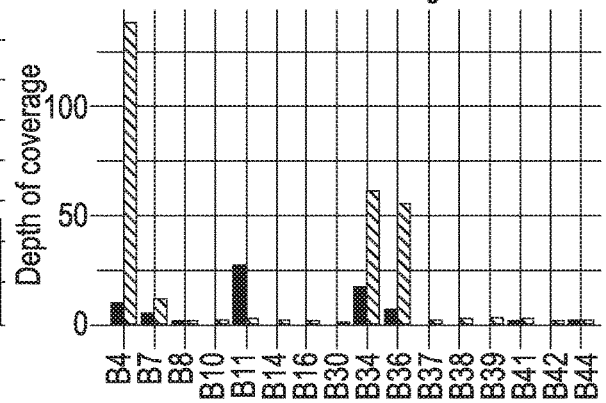

FIG. 26 shows the same types of information as FIG. 25. According to these results, only partial genomes could be obtained without hybrid selection and only in a few samples. In some samples (B4, B7, B34, B36, B11, B41, B44), hybrid selection helps to increase the fraction of the genome that can be assembled.

Figure 27:
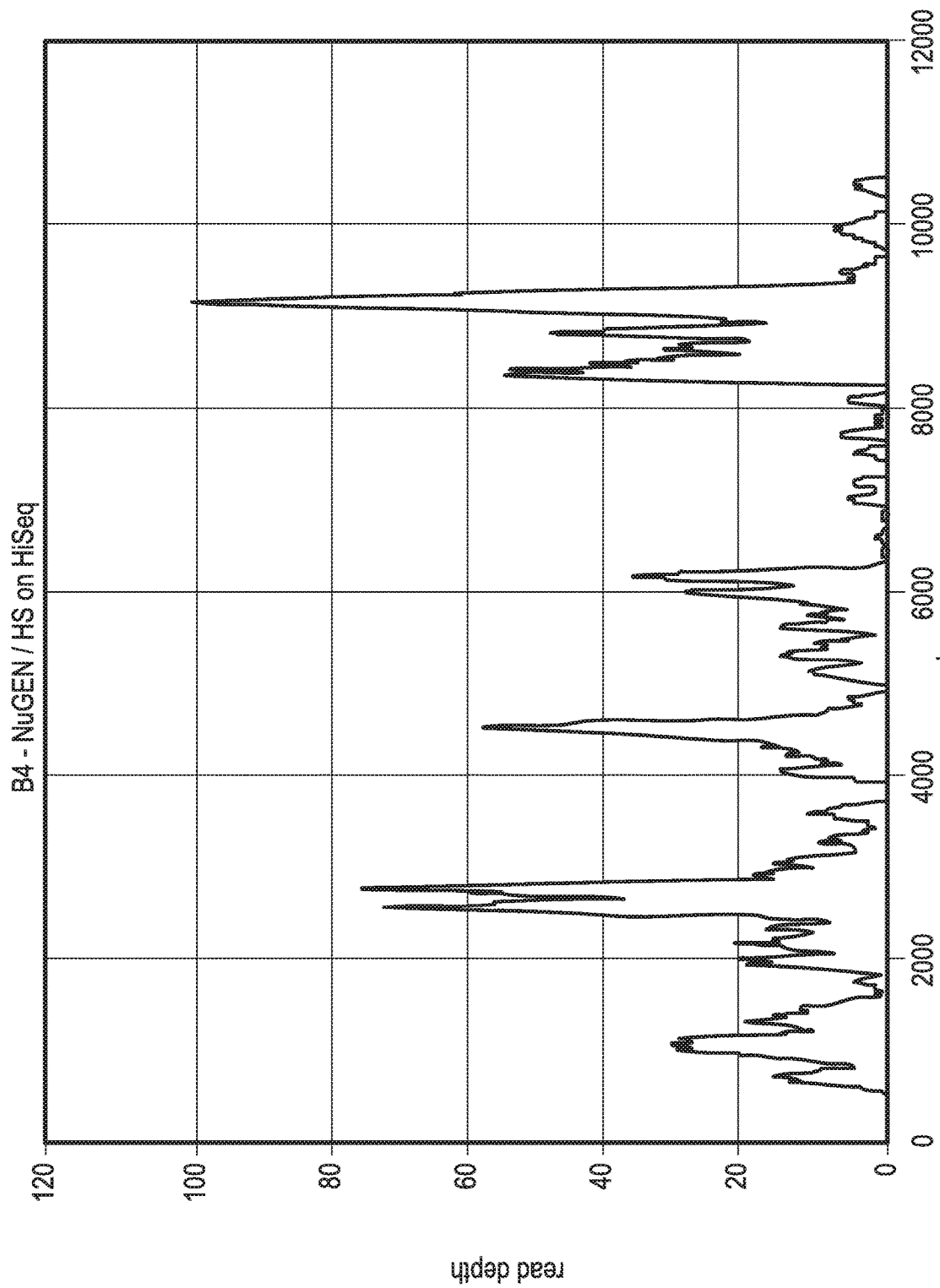
FIGS. 27 and 28 show coverage plots of reads mapped to the Zika genome in a clinical sample from the Zika infested area in South America.
Figure 28:
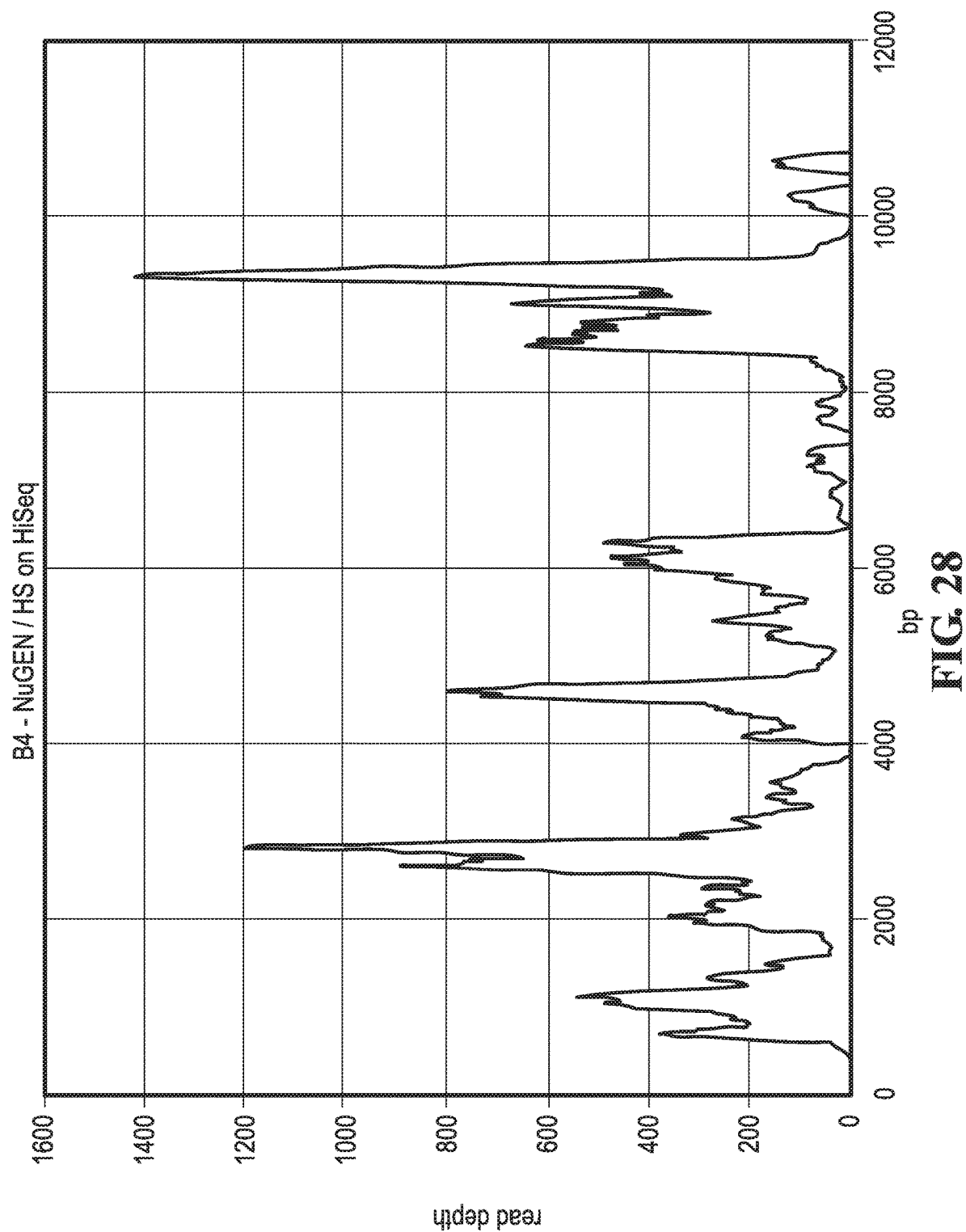

FIGS. 27 and 28 show coverage plots of reads mapped to the Zika genome in 16 clinical samples from the Zika infested area in South America. As can be seen from both figures, the benefit of hybrid selection is clearly observable, notably through the higher coverage in FIG. 28.

Example 6

A list of targeted viruses used to design the probe set to target all human-infecting viruses is given below. The list was developed based on NCBI's viral accession list. The first column is a regex string matching viral taxa in that list. The second column is a pair of numbers (m, c) where m is the number of mismatches used for that virus in designing probes, and c is the "cover extension" used.

(Human)?(R|r)espiratory syncytial virus (2, 20)
(Sudan ebolavirus|Bundibugyo virus|Tai Forest ebolavirus-|Reston ebolavirus) (2, 0)
Achimota virus([0-9]+)? (0, 0)
*Aedes* flavivirus (1, 0)
Aguacate virus (0, 0)
Akabane virus (1, 0)
Alethinophid [0-9]+reptarenavirus (0, 0)
Allpahuayo mammarenavirus (0, 0)
Amapari mammarenavirus (0, 0)
Andes virus (0, 0)
Apoi virus (0, 0)
Aravan virus (0, 0)
Aroa virus (0, 0)
Arumowot virus (0, 0)
Atlantic salmon paramyxovirus (0, 0)
Australian bat lyssavirus (1, 0)
Avian bornavirus (0, 0)
Avian metapneumovirus (1, 0)
Avian paramyxovirus(es)?([0-9]+| penguin/Falkland Islands/324/2007)? (1, 30)
BK polyomavirus (1, 10)
Bagaza virus (1, 0)
Banna virus (1, 0)
Bat hepevirus (0, 0)
Bat sapovirus TLC58/HK (0, 0)
Bear Canyon mammarenavirus (0, 0)
Beilong virus (0, 0)
Betacoronavirus 1 (2, 20)
Betapapillomavirus 1 (1, 0)
Betapapillomavirus 2 (1, 0)
Betapapillomavirus 3 (0, 0)
Betapapillomavirus 4 (0, 0)
Betapapillomavirus 5 (0, 0)
Betapapillomavirus 6 (0, 0)
Bhanja virus (0, 0)
Bokeloh bat lyssavirus (0, 0)
Borna disease virus (1, 0)
Bourbon virus (0, 0)
Bovine hepacivirus (1, 0)
Bovine parainfluenza virus 3 (1, 0)
Bovine respiratory syncytial virus (0, 0)
Brazoran virus (0, 0)
Bunyamwera virus (1, 20)
California encephalitis virus (2, 20)
Candiru virus (1, 0)
Canine distemper virus (2, 10)
Canine pneumovirus (0, 0)
Cedar virus (0, 0)
Cell fusing agent virus (1, 0)
Cetacean morbillivirus (0, 0)
Chandipura virus (1, 0)
Chaoyang virus (1, 0)
Chapare mammarenavirus (0, 0)
Chikungunya virus (2, 10)
Colobus monkey papillomavirus (0, 0)
Colorado tick fever virus (0, 0)
Cowpox virus (2, 30)
Crimean-Congo hemorrhagic fever virus (2, 30)
*Culex* flavivirus (1, 0)
Cupixi mammarenavirus (0, 0)
Dengue virus (3, 30)
Dobrava-Belgrade virus (1, 0)
Donggang virus (0, 0)
Dugbe virus (1, 0)
Duvenhage virus (1, 0)
Eastern equine encephalitis virus (1, 0)
Entebbe bat virus (0, 0)
Enterovirus A (3, 40)
Enterovirus B (2, 40)
Enterovirus C (2, 40)
Enterovirus D (2, 20)
European bat lyssavirus 1 (1, 10)
European bat lyssavirus 2 (1, 0)
Eyach virus (0, 0)
Feline morbillivirus (1, 0)
Fer-de-Lance paramyxovirus (0, 0)
Fitzroy River virus (0, 0)
Flexal mammarenavirus (0, 0)
GB virus C (3, 30)
Gairo virus (0, 0)
Gemycircularvirus SL1 (1, 0)
Goose paramyxovirus SF02 (0, 0)
Great Island virus (1, 0)
Guanarito mammarenavirus (1, 0)
Hantaan virus (1, 0)
Hantavirus Z10 (1, 0)
Heartland virus (1, 0)
Hendra virus (1, 0)
Hepatitis A virus (2, 20)
Hepatitis B virus (4, 40)
Hepatitis C virus (4, 50)
Hepatitis E virus (3, 40)
Hepatitis delta virus (3, 10)
Human bocavirus (1, 10)
Human coronavirus 229E (1, 0)
Human coronavirus HKU1 (1, 10)
Human coronavirus NL63 (1, 10)
Human endogenous retrovirus K (1, 0)
Human enteric coronavirus strain 4408 (0, 0)
Human genital-associated circular DNA virus-1 (0, 0)
Human herpesvirus 1 (1, 20)
Human herpesvirus 2 (1, 30)
Human herpesvirus 3 (1, 20)
Human herpesvirus 4 (2, 30)
Human herpesvirus 5 (3, 40)
Human herpesvirus 6[AB] (1, 0)
Human herpesvirus 7 (0, 20)
Human herpesvirus 8 (0, 30)
Human immunodeficiency virus 1 (4, 50)
Human immunodeficiency virus 2 (3, 0)
Human mastadenovirus A (1, 20)
Human mastadenovirus B (2, 20)
Human mastadenovirus C (2, 20)
Human mastadenovirus D (2, 20)
Human mastadenovirus E (2, 20)
Human mastadenovirus F (1, 0)
Human mastadenovirus G (1, 0)
Human metapneumovirus (2, 20)
Human papillomavirus(type [0-9]+)? (1, 0)
Human parainfluenza virus 1 (1, 10)
Human parainfluenza virus 2 (1, 10)

Human parainfluenza virus 3 (2, 10)
Human parainfluenza virus 4 (1, 0)
Human parechovirus (2, 0)
Human picobirnavirus (0, 0)
Human smacovirus 1 (1, 0)
Ikoma lyssavirus (0, 0)
Ilheus virus (0, 0)
Influenza A virus (3, 30)
Influenza B virus (1, 0)
Influenza C virus (0, 0)
Ippy mammarenavirus (0, 0)
Irkut virus (0, 0)
J-virus (0, 0)
JC polyomavirus (1, 10)
Japanese encephalitis virus (2, 20)
Junin mammarenavirus (1, 0)
KI polyomavirus (1, 0)
Kadipiro virus (0, 0)
Kamiti River virus (1, 0)
Kedougou virus (0, 0)
Khuj and virus (0, 0)
Kokobera virus (1, 0)
Kyasanur forest disease virus (1, 0)
Lagos bat virus (1, 0)
Langat virus (1, 0)
Lassa mammarenavirus (3, 30)
Latino mammarenavirus (1, 0)
Leopards Hill virus (1, 0)
Liao ning virus (0, 0)
Ljungan virus (1, 0)
Lloviu cuevavirus (0, 0)
Louping ill virus (1, 0)
Lujo mammarenavirus (0, 0)
Luna mammarenavirus (0, 0)
Lunk virus NKS-1 (0, 0)
Lymphocytic choriomeningitis mammarenavirus (1, 0)
Lyssavirus Ozernoe (0, 0)
MSSI2\0.225 virus (0, 0)
Machupo mammarenavirus (0, 0)
Mamastrovirus 1 (2, 20)
Manzanilla virus (1, 0)
Mapuera virus (0, 0)
Marburg marburgvirus (2, 20)
Mayaro virus (1, 0)
Measles virus (2, 0)
Menangle virus (1, 0)
Mercadeo virus (1, 0)
Merkel cell polyomavirus (1, 10)
Middle East respiratory syndrome coronavirus (1, 20)
Mobala mammarenavirus (0, 0)
Modoc virus (0, 0)
Mojiang virus (0, 0)
Mokola virus (1, 0)
Monkeypox virus (1, 20)
Montana *myotis* leukoencephalitis virus (0, 0)
Mopeia Lassa virus reassortant 29 (1, 0)
Mopeia mammarenavirus (1, 0)
Morogoro virus (0, 0)
Mossman virus (0, 0)
Mumps virus (2, 20)
Murine pneumonia virus (1, 0)
Murray Valley encephalitis virus (1, 0)
Nariva virus (0, 0)
Newcastle disease virus (3, 40)
Nipah virus (1, 0)
Norwalk virus (2, 40)
Norway rat hepacivirus([0-9]+)? (0, 0)
Ntaya virus (1, 0)
O'nyong-nyong virus (1, 0)
Oliveros mammarenavirus (0, 0)
Omsk hemorrhagic fever virus (1, 0)
Oropouche virus (1, 0)
Parainfluenza virus 5 (1, 0)
Parana mammarenavirus (1, 0)
Parramatta River virus (0, 0)
Peste-des-petits-ruminants virus (2, 20)
Pichinde mammarenavirus (1, 0)
Pirital mammarenavirus (1, 0)
Piscihepevirus A (0, 0)
Porcine parainfluenza virus 1 (1, 0)
Porcine rubulavirus (0, 0)
Powassan virus (1, 0)
Primate T-lymphotropic virus 1 (1, 0)
Primate T-lymphotropic virus 2 (1, 0)
Primate erythroparvovirus 1 (1, 10)
Punta Toro virus (1, 0)
Puumala virus (1, 20)
Quang Binh virus (0, 0)
Rabies virus (3, 30)
Razdan virus (0, 0)
Reptile bornavirus 1 (0, 0)
Rhinovirus A (1, 50)
Rhinovirus B (1, 30)
Rift Valley fever virus (2, 0)
Rinderpest virus (1, 0)
Rio Bravo virus (1, 0)
Rodent Torque teno virus([0-9]+)? (1, 0)
Rodent hepacivirus (0, 0)
Ross River virus (1, 10)
Rotavirus A (5, 50)
Rotavirus B (1, 20)
Rotavirus C (2, 30)
Rotavirus F (0, 0)
Rotavirus G (1, 0)
Rotavirus H (1, 0)
Rotavirus I (1, 0)
Royal Farm virus (1, 0)
Rubella virus (2, 0)
Sabia mammarenavirus (0, 0)
Salem virus (0, 0)
Sandfly fever Naples virus (1, 20)
Sandfly fever Sicilian virus (1, 0)
Sapporo virus (1, 0)
Sathuperi virus (1, 0)
Seal anellovirus(TFFN/USA/2006|[0-9]+)? (0, 0)
Semliki Forest virus (1, 10)
Sendai virus (1, 0)
Seoul virus (2, 10)
Sepik virus (0, 0)
Severe acute respiratory syndrome-related coronavirus (2, 20)
Severe fever with thrombocytopenia syndrome virus (2, 10)
Shamonda virus (1, 0)
Shimoni bat virus (0, 0)
Shuni virus (1, 0)
Simbu virus (0, 0)
Simian torque teno virus([0-9]+)? (0, 0)
Simian virus 40 (1, 0)
Simian virus 41 (0, 0)
Sin Nombre virus (1, 0)
Sindbis virus (1, 0)
Small anellovirus (0, 0)
Sosuga virus (0, 0)
Spanish goat encephalitis virus (0, 0)

Spondweni virus (0, 0)
St\. Louis encephalitis virus (1, 0)
Sunshine virus (0, 0)
TTV-like mini virus (0, 0)
Tacaribe mammarenavirus (1, 0)
Tailam virus (0, 0)
Tamana bat virus (0, 0)
Tamiami mammarenavirus (1, 0)
Tembusu virus (1, 20)
Thogoto virus (1, 0)
Thottapalayam virus (1, 0)
Tick-borne encephalitis virus (2, 20)
Tioman virus (0, 0)
Torque teno *canis* virus (1, 0)
Torque teno douroucouli virus (0, 0)
Torque teno *felis* virus (1, 0)
Torque teno midi virus([0-9]+) (0, 0)
Torque teno mini virus(ALA22|ALH8|[0-9]+)? (1, 0)
Torque teno sus virus([a-z0-9]+)? (1, 20)
Torque teno tamarin virus (0, 0)
Torque teno virus([0-9]+)? (1, 20)
Torque teno *zalophus* virus([0-9]+)? (0, 0)
Tuhoko virus([0-9]+)? (0, 0)
Tula virus (1, 0)
Tupaia paramyxovirus (0, 0)
Usutu virus (1, 0)
Uukuniemi virus (1, 20)
Vaccinia virus (1, 30)
Variola virus (1, 0)
Venezuelan equine encephalitis virus (2, 0)
Vesicular stomatitis Indiana virus (1, 10)
WU Polyomavirus (1, 0)
Wesselsbron virus (1, 0)
West Caucasian bat virus (0, 0)
West Nile virus (2, 20)
Western equine encephalitis virus (1, 10)
Whitewater Arroyo mammarenavirus (1, 0)
Yellow fever virus (2, 20)
Yokose virus (0, 0)
Yug Bogdanovac virus (0, 0)
Zaire ebolavirus (2, 10)
Zika virus (2, 10)
*Zygosaccharomyces bailii* virus Z (0, 0)

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11332783B2). An electronic copy of the "Sequence Listing" will also be available from the USPTO upon request and payment of the fee set forth in 37 CFR 1.19(b)(3).

What is claimed is:

1. A method for generating probes for analyzing a sample comprising a target sequence, the method comprising:
   a. constructing candidate probes capable of hybridizing the target sequence and one or more variations of the target sequence, said candidate probes collectively having a hybridization pattern along the length of the target sequence;
   b. determining an individual hybridization pattern for each candidate probe to provide a collection of individual hybridization patterns;
   c. solving a set cover problem for the individual hybridization patterns, wherein the set cover problem comprises a set of elements {1, 2 . . . i . . . m} comprising the entire target sequence and the one or more variations of the target sequence, and a collection of candidate probes covering the set of elements, and wherein the set cover problem identifies the smallest set of probes from the candidate probes that covers the set of elements, thereby reducing the number of candidate probes needed to cover the entire target sequence and the one or more variations of the target sequence, and providing a final probe set; and
   d. synthesizing the probes of the final probe set.

2. The method of claim 1, wherein the set cover solving process is a weighted set cover solving process, a partial set cover solving process, or a partial weighted set cover solving process.

3. The method of claim 2 wherein subjecting the individual hybridization patterns to a set cover solving process comprises:
   a. allocating a lower weight to those individual hybridization patterns that correspond to candidate probes that are specific to the target sequence; and
   b. allocating a higher weight to those individual hybridization patterns that correspond to candidate probes that are not specific to the target sequence.

4. The method of claim 1, wherein the set cover solving process is a greedy method.

5. The method of claim 1, further comprising:
   minimizing a loss function depending on overhang parameters and mismatch parameters such that the total number of selected probes is no higher than a threshold number to provide input parameters to the set cover solving process.

6. A method of analyzing a sample comprising a target sequence, the method comprising:
   a. contacting the selected probes of claim 1 to the target sequence or a fragment thereof; and
   b. sequencing the target sequence or fragment thereof that hybridizes to one or more selected probes of the set.

7. The method of claim 6, further comprising analyzing the target sequence or a fragment thereof that is hybridized to one or more selected probes, wherein analysis of the target sequence or a fragment thereof hybridized to a selected probe is by solution hybrid selection.

8. The method of claim 7, wherein each of the selected probes further comprises an adapter.

9. The method of claim 8, wherein each of the selected probes comprises two adapters, and wherein a first adapter is alternated with a second adapter.

10. The method of claim 8, wherein two of the selected probes overlap.

11. The method of claim 6, wherein the candidate probe or the selected probe is a nucleic acid sequence, and wherein the nucleic acid is DNA, RNA, PNA or other non-naturally occurring nucleic acid.

12. The method of claim 6, wherein the sample is a biological sample.

13. The method of claim 12, wherein the biological sample is a blood, buccal, cell, cerebrospinal fluid, mucus, saliva, semen, tissue, tumor, feces, urine or vaginal sample.

14. The method of claim 12, wherein the biological sample is obtained from a human.

15. The method of claim 6, wherein the target sequence is a nucleotide sequence.

16. The method of claim 15, wherein the nucleotide sequence is a DNA sequence or an RNA sequence.

17. The method of claim 15, wherein the nucleotide sequence is a pathogenic or viral sequence.

18. The method of claim 17, wherein the viral sequence is a human respiratory syncytial virus, Sudan ebola virus, Bundibugyo virus, Tai Forest ebola virus, Reston ebola virus, Achimota, *Aedes* flavivirus, Aguacate virus, Akabane virus, Alethinophid reptarenavirus, Allpahuayo mammarenavirus, Amapari mammarenavirus, Andes virus, Apoi virus, Aravan virus, Aroa virus, Arumwot virus, Atlantic salmon paramyxovirus, Australian bat lyssavirus, Avian bornavirus, Avian metapneumovirus, Avian paramyxoviruses, penguin or Falkland Islandsvirus, BK polyomavirus, Bagaza virus, Banna virus, Bat hepevirus, Bat sapovirus, Bear Canon mammarenavirus, Beilong virus, Betacoronoavirus, Betapapillomavirus 1-6, Bhanja virus, Bokeloh bat lyssavirus, Borna disease virus, Bourbon virus, Bovine hepacivirus, Bovine parainfluenza virus 3, Bovine respiratory syncytial virus, Brazoran virus, Bunyamwere virus, California encephalitis virus, Candiru virus, Canine distemper virus, Canaine pneumovirus, Cedar virus, Cell fusing agent virus, Cetacean morbillivirus, Chandipura virus, Chaoyang virus, Chapare mammarenavirus, Chikungunya virus, Colobus monkey papillomavirus, Colorado tick fever virus, Cowpox virus, Crimean-Congo hemorrhagic fever virus, *Culex* flavivirus, Cupixi mammarenavirus, Dengue virus, Dobrava-Belgrade virus, Donggang virus, Dugbe virus, Duvenhage virus, Eastern equine encephalitis virus, Entebbe bat virus, Enterovirus A-D, European bat lyssavirus 1-2, Eyach virus, Feline morbillivirus, Fer-de-Lance paramyxovirus, Fitzroy River virus, Flexal mammarenavirus, GB virus C, Gairo virus, Gemycircularvirus, Goose paramyxovirus SF02, Great Island virus, Guanarito mammarenavirus, Hantaan virus, Hantavirus Z10, Heartland virus, Hendra virus, Hepatitis A/B/C/E, Hepatitis delta virus, Human bocavirus, Human coronavirus, Human endogenous retrovirus K, Human enteric coronavirus, Human genital-associated circular DNA virus-1, Human herpesvirus 1-8, Human immunodeficiency virus 1/2, Human mastadenovirus A-G, Human papillomavirus, Human parainfluenza virus 1-4, Human paraechovirus, Human picobirnavirus, Human smacovirus, Ikoma lyssavirus, Irkut virus, J-virus, JC polyomavirus, Japanese encephalitis virus, Junin mammarenavirus, KI polyomavirus, Kadipiro virus, Kamiti River virus, Kedougou virus, Khuj and virus, Kokobera virus, Kyasanur forest disease virus, Lagos bat virus, Langat virus, Lassa virus, Lassa mammarenavirus, Latino mammarenavirus, Leopards Hill virus, Liao ning virus, Ljungan virus, Lloviu virus, Louping ill virus, Lujo mammarenavirus, Luna mammarenavirus, Lunk virus, Lymphocytic choriomeningitis mammarenavirus, Lyssavirus Ozernoe, MSSI2\ 0.225 virus, Machupo mammarenavirus, Mamastrovirus 1, Manzanilla virus, Mapuera virus, Marburg virus, Mayaro virus, Measles virus, Menangle virus, Mercadeo virus, Merkel cell polyomavirus, Middle East respiratory syndrome coronavirus, Mobala mammarenavirus, Modoc virus, Moijang virus, Mokolo virus, Monkeypox virus, Montana *myotis* leukoenchalitis virus, Mopeia lassa virus reassortant 29, Mopeia mammarenavirus, Morogoro virus, Mossman virus, Mumps virus, Murine pneumonia virus, Murray Valley encephalitis virus, Nariva virus, Newcastle disease virus, Nipah virus, Norwalk virus, Norway rat hepacivirus, Ntaya virus, O'nyong-nyong virus, Oliveros mammarenavirus, Omsk hemorrhagic fever virus, Oropouche virus, Parainfluenza virus 5, Parana mammarenavirus, Parramatta River virus, Peste-des-petits-ruminants virus, Pichande mammarenavirus, Pirital mammarenavirus, Pi scihepevirus A, Porcine parainfluenza virus 1, porcine rubulavirus, Powassan virus, Primate T-lymphotropic virus 1-2, Primate erythroparvovirus 1, Punta Toro virus, Puumala virus, Quang Binh virus, Rabies virus, Razdan virus, Reptile bornavirus 1, Rhabdovirus, Rhinovirus A-B, Rift Valley fever virus, Rinderpest virus, Rio Bravo virus, Rodent Torque Teno virus, Rodent hepacivirus, Ross River virus, Rotavirus A-I, Royal Farm virus, Rubella virus, Sabia mammarenavirus, Salem virus, Sandfly fever Naples virus, Sandfly fever Sicilian virus, Sapporo virus, Sathuperi virus, Seal anellovirus, Semliki Forest virus, Sendai virus, Seoul virus, Sepik virus, Severe acute respiratory syndrome-related coronavirus, Severe fever with thrombocytopenia syndrome virus, Shamonda virus, Shimoni bat virus, Shuni virus, Simbu virus, Simian torque teno virus, Simian virus 40-41, Sin Nombre virus, Sindbis virus, Small anellovirus, Sosuga virus, Spanish goat encephalitis virus, Spondweni virus, St. Louis encephalitis virus, Sunshine virus, TTV-like mini virus, Tacaribe mammarenavirus, Taila virus, Tamana bat virus, Tamiami mammarenavirus, Tembusu virus, Thogoto virus, Thottapalayam virus, Tick-borne encephalitis virus, Tioman virus, Torque teno *canis* virus, Torque teno douroucouli virus, Torque teno *felis* virus, Torque teno midi virus, Torque teno sus virus, Torque teno tamarin virus, Torque teno virus, Torque teno *zalophus* virus, Tuhoko virus, Tula virus, Tupaia paramyxovirus, Usutu virus, Uukuniemi virus, Vaccinia virus, Variola virus, Venezuelan equine encephalitis virus, Vesicular stomatitis Indiana virus, WU Polyomavirus, Wesselsbron virus, West Caucasian bat virus, West Nile virus, Western equine encephalitis virus, Whitewater Arroyo mammarenavirus, Yellow fever virus, Yokose virus, Yug Bogdanovac virus, Zaire ebolavirus, Zika virus, or *Zygosaccharomyces bailii* virus Z viral sequence.

19. The method of claim 18, wherein the hepatitis viral sequence is a hepatitis A, hepatitis B or hepatitis C viral sequence.

20. The method of claim 18, wherein the influenza viral sequence is an influenza A or influenza B viral sequence.

21. The method of claim 1, wherein each probe in a probe set is between 15 to 150 base pairs.

22. The method of claim 1, wherein each probe in a probe set is between 20 to 175 base pairs.

23. The method of claim 1, wherein each probe in a probe set is between 70 to 130 base pairs.

* * * * *

UNITED STATES PATENT AND TRADEMARK OFFICE
CERTIFICATE OF CORRECTION

PATENT NO. : 11,332,783 B2
APPLICATION NO. : 15/756546
DATED : May 17, 2022
INVENTOR(S) : Metsky et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 780 days.

Signed and Sealed this
Eighteenth Day of February, 2025

Coke Morgan Stewart
*Acting Director of the United States Patent and Trademark Office*